(12) United States Patent
Nakanotani et al.

(10) Patent No.: US 11,937,495 B2
(45) Date of Patent: Mar. 19, 2024

(54) ORGANIC LIGHT EMITTING ELEMENT, COMPOSITION AND MEMBRANE

(71) Applicants: KYUSHU UNIVERSITY, NATIONAL UNIVERSITY CORPORATION, Fukuoka (JP); KWANSEI GAKUIN EDUCATIONAL FOUNDATION, Nishinomiya (JP); KYULUX, INC., Fukuoka (JP)

(72) Inventors: Hajime Nakanotani, Fukuoka (JP); Takuji Hatakeyama, Sanda (JP); Yasuhiro Kondo, Ichihara (JP); Yasuyuki Sasada, Ichihara (JP); Motoki Yanai, Ichihara (JP); Chin-Yiu Chan, Fukuoka (JP); Masaki Tanaka, Fukuoka (JP); Hiroki Noda, Fukuoka (JP); Chihaya Adachi, Fukuoka (JP); Yoshitake Suzuki, Fukuoka (JP); Naoto Notsuka, Fukuoka (JP)

(73) Assignees: KYUSHU UNIVERSITY, NATIONAL UNIVERSITY CORPORATION, Fukuoka (JP); KWANSEI GAKUIN EDUCATIONAL FOUNDATION, Hyogo (JP); KYULUX, INC., Fukuoka (JP)

( * ) Notice: Subject to any disclaimer, the term of this patent is extended or adjusted under 35 U.S.C. 154(b) by 392 days.

(21) Appl. No.: 17/270,158

(22) PCT Filed: Aug. 7, 2019

(86) PCT No.: PCT/JP2019/031127
§ 371 (c)(1),
(2) Date: Feb. 22, 2021

(87) PCT Pub. No.: WO2020/039930
PCT Pub. Date: Feb. 27, 2020

(65) Prior Publication Data
US 2021/0202851 A1    Jul. 1, 2021

(30) Foreign Application Priority Data
Aug. 23, 2018 (JP) .................................. 2018-156709
Apr. 9, 2019 (JP) .................................. 2019-073933

(51) Int. Cl.
H10K 85/30 (2023.01)
C07D 209/86 (2006.01)
(Continued)

(52) U.S. Cl.
CPC ......... H10K 85/322 (2023.02); C07D 209/86 (2013.01); C07F 5/027 (2013.01);
(Continued)

(58) Field of Classification Search
CPC ....... H10K 85/322; C07F 5/027; C09K 11/06; C09K 2211/1029
See application file for complete search history.

(56) References Cited

U.S. PATENT DOCUMENTS

2016/0190478 A1    6/2016  Nakanotani et al.
2018/0301629 A1*  10/2018  Hatakeyama .......... C09K 11/06

FOREIGN PATENT DOCUMENTS

CN    105431439 A    3/2016
EP    3109253 A1    12/2016
(Continued)

OTHER PUBLICATIONS

Japanese and English version of International Preliminary Report on Patentability of Chapter I, i.e., International Search Opinion which we received from the WIPO as the International Bureau of the PCT.
(Continued)

*Primary Examiner* — Khanh T Nguyen
(74) *Attorney, Agent, or Firm* — BROWDY AND NEIMARK, PLLC

(57) ABSTRACT

An organic light-emitting device containing both a compound represented by the following general formula (1) and
(Continued)

a compound represented by the following general formula (2) has a high light emission efficiency. The rings a to c each are a benzene ring that can be optionally condensed, $R^1$ and $R^2$ each represent a substituted or unsubstituted aryl group, etc., four of $R^{31}$ to $R^{35}$ each are a substituted or unsubstituted carbazol-9-yl group, but all of these four are not the same, and the remaining one is a hydrogen atom, a cyano group, etc.

8 Claims, 2 Drawing Sheets

(51) Int. Cl.
*C07F 5/02* (2006.01)
*C09K 11/06* (2006.01)
*H10K 85/60* (2023.01)
*H10K 50/11* (2023.01)
*H10K 101/10* (2023.01)

(52) U.S. Cl.
CPC .......... *C09K 11/06* (2013.01); *H10K 85/6572* (2023.02); *C09K 2211/1011* (2013.01); *C09K 2211/1014* (2013.01); *C09K 2211/1022* (2013.01); *H10K 50/11* (2023.02); *H10K 2101/10* (2023.02)

(56) References Cited

FOREIGN PATENT DOCUMENTS

| | | |
|---|---|---|
| JP | 5669163 B | 12/2014 |
| JP | 5935199 B2 | 5/2016 |
| JP | 2018-061028 A | 4/2018 |
| JP | 2018-061030 A | 4/2018 |
| WO | 2015/102118 A1 | 7/2015 |
| WO | 2017/188111 A1 | 11/2017 |
| WO | 2018/030446 A1 | 2/2018 |
| WO | 2018/062278 A1 | 4/2018 |

OTHER PUBLICATIONS

International Search Report and Search Opinion dated Oct. 29, 2019, in International Application No. PCT/JP2019/031127.
Extended European Search Report dated Sep. 16, 2021 issued in the corresponding European patent application No. 19852474.6.
Office Action dated Jan. 1, 2024 issued in the corresponding Chinese patent application No. 201980055066.1 with its English Machine Translation.

\* cited by examiner

[FIG. 1]
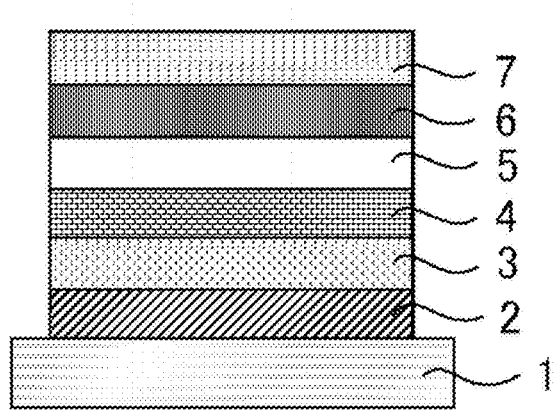
[FIG. 2]
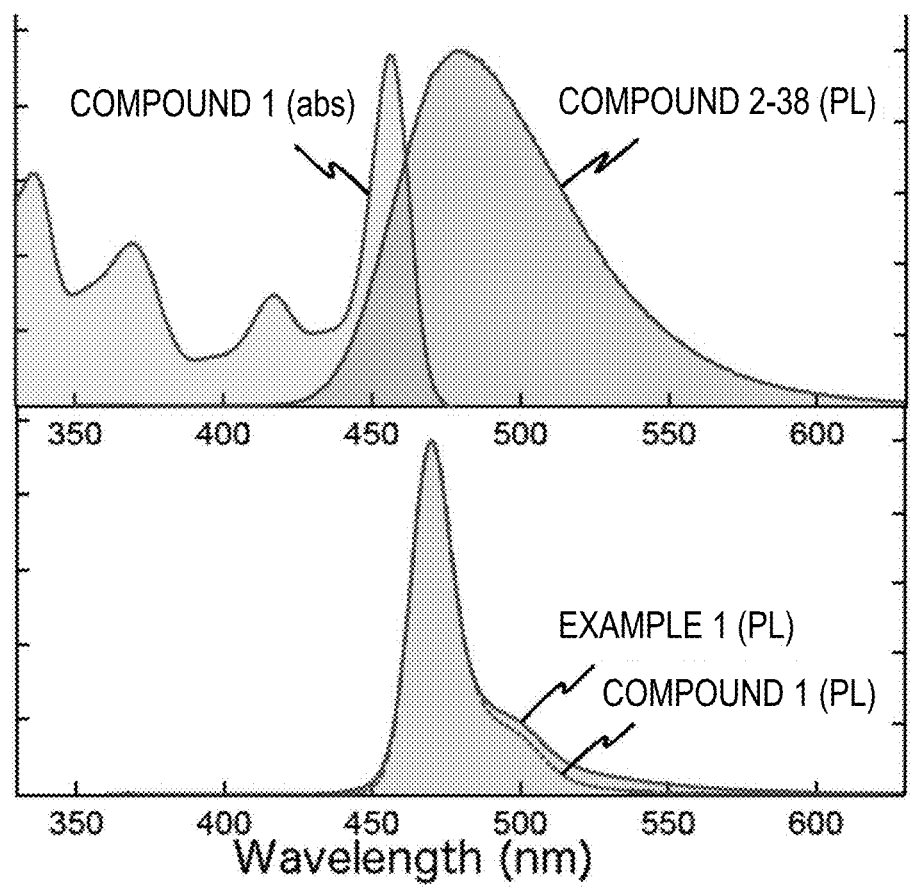

[FIG. 3]
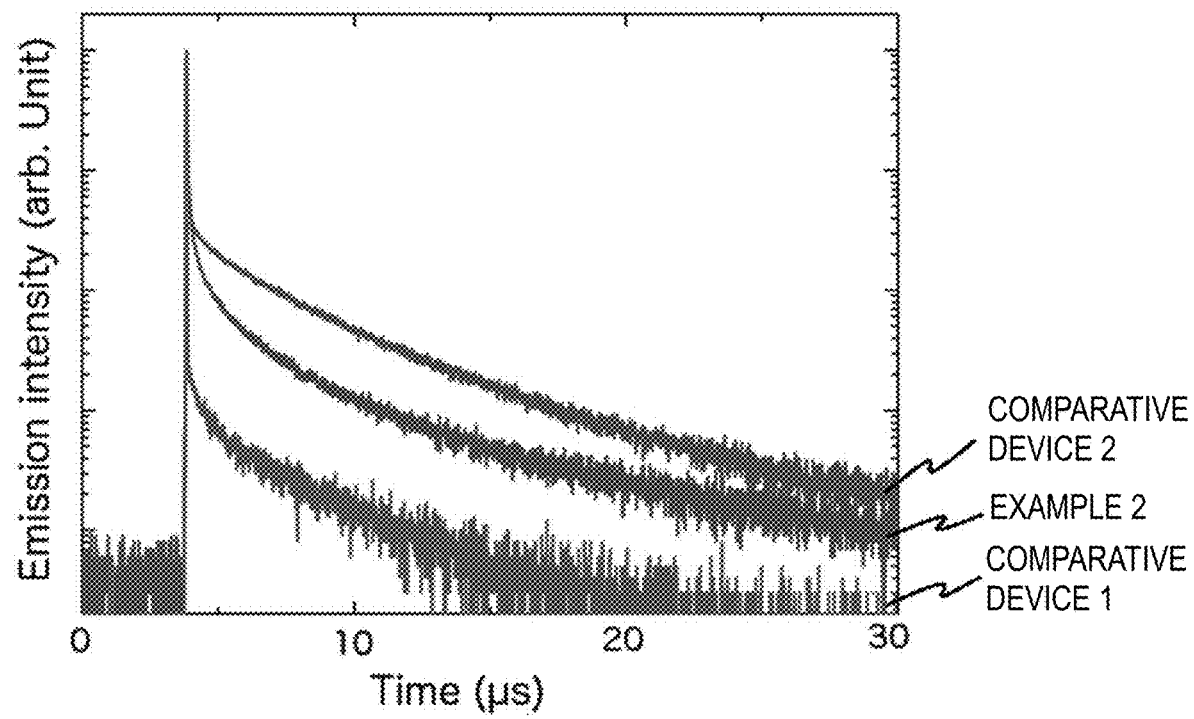

ORGANIC LIGHT EMITTING ELEMENT, COMPOSITION AND MEMBRANE

TECHNICAL FIELD

The present invention relates to an organic light-emitting device, a composition and a film.

BACKGROUND ART

Studies for enhancing the light emission efficiency of light-emitting devices such as organic electroluminescent devices (organic EL devices) are being made actively. In particular, various kinds of efforts have been made for increasing light emission efficiency by newly developing an electron transport material, a hole transport material and a light-emitting material to constitute an organic electroluminescent device. For example, PTL 1 describes that a polycyclic aromatic compound formed of plural aromatic rings linked via a boron atom and a nitrogen atom are useful as a light-emitting material for organic electroluminescent devices.

On the other hand, studies for increasing light emission efficiency have also been made by combining materials for use in a light-emitting layer of an organic electroluminescent device. For example, PTL 2 describes adding a delayed fluorescent material to a light-emitting layer containing a light-emitting material and a host material, in which the lowest excited singlet energy level of the delayed fluorescent material is in an intermediate state between a light-emitting material and a host material. In an excited state, a delayed fluorescent material may readily undergo reverse intersystem crossing from an excited triplet state to an excited singlet state, and therefore such a delayed fluorescent material can utilize not only the excited singlet state but also the excited triplet state for light emission through a route via reverse intersystem crossing. Consequently, the light emission efficiency of an organic electroluminescent device can be increased by adding a delayed fluorescent material thereto, the patent publication says so.

CITATION LIST

Patent Literature

PTL 1: JP 5935199
PTL 2: JP 5669163

SUMMARY OF INVENTION

Technical Problem

By adding a delayed fluorescent material to a light-emitting layer containing a light-emitting material and a host material in an organic electroluminescent device, in which the lowest excited singlet energy level of the delayed fluorescent material added is in an intermediate state between the light-emitting material and the host material, the light emission efficiency of the organic electroluminescent device surely increases. However, even the light emission efficiency thus increased by adding such a delayed fluorescent material is not still on a satisfactory level in many cases, and in particular, few blue light-emitting devices could have realized a sufficiently highly increased external quantum yield. Consequently, a new technique capable of attaining a high light emission efficiency and simultaneously capable of reaching a breakthrough in realizing a high-efficiency blue light-emitting device is desired.

Solution to Problem

Given the situation, the present inventors have made various investigations for the purpose of finding out a combination of materials capable of providing an organic light-emitting device having a high light emission efficiency. In particular, the inventors have promoted the investigations bearing in mind discovery of a combination of materials capable of reaching a breakthrough in realizing a high-efficiency blue light-emitting device.

As a result of assiduous studies, the present inventors have found that combined use of a polycyclic aromatic compound having a specific structure and a delayed fluorescent material having a specific structure can provide an organic light-emitting device having a high light emission efficiency, and have reached the present invention described hereinunder.

[1] An organic light-emitting device containing both a compound having one or more structures represented by the following general formula (1), and a compound represented by the following general formula (2).

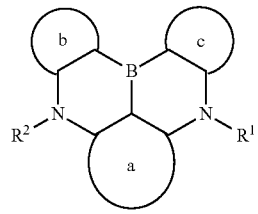

General Formula (1)

In the general formula (1), the ring a, the ring b and the ring c each independently represent a benzene ring that may be condensed with any other ring to form an aryl ring or a heteroaryl ring, and at least one hydrogen atom in these rings may be substituted; $R^1$ and $R^2$ each independently represent a substituted or unsubstituted aryl group, or a substituted or unsubstituted heteroaryl group bonding via the benzene ring; $R^1$ may bond to the carbon atom neighboring to the bonding position (atom) to N in the ring a and/or the ring c via —O—, —S—, —C(—$R^{c1}$)$_2$— or a single bond; $R^2$ may bond to the carbon atom neighboring to the bonding position (atom) to N in the ring a and/or the ring b via —O—, —S—, —C(—$R^{c2}$)$_2$— or a single bond; $R^{c1}$ and $R^{c2}$ each independently represent a hydrogen atom or an alkyl group.

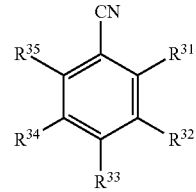

General Formula (2)

In the general formula (2), four of $R^{31}$ to $R^{35}$ each independently represent a substituted or unsubstituted carbazol-9-yl group, but all of these four are not the same, and the remaining one represents a hydrogen atom, a substituted or unsubstituted aryl group, a substituted or unsubstituted carbazol-9-yl group, or a cyano group.

[2] The organic light-emitting device according to [1], wherein the compound having one or more structures represented by the general formula (1) is a compound having two structures represented by the general formula (1).

[3] The organic light-emitting device according to [2], wherein the compound represented by the general formula (1) is a compound represented by the following general formula (1a).

General Formula (1a)

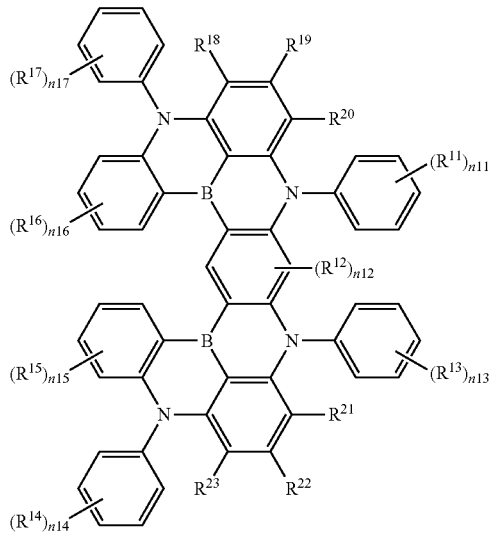

In the general formula (1a), $R^{11}$ to $R^{17}$ each independently represent a substituent, $R^{18}$ to $R^{23}$ each independently represent a hydrogen atom or a substituent, n11, n13, n14 and n17 each independently represent an integer of any of 0 to 5, n12 represents an integer of any of 0 to 2, n15 and n16 each independently represent an integer of any of 0 to 4.

[4] The organic light-emitting device according to [3], wherein $R^{19}$ and $R^{22}$ each independently represent a substituent.

[5] The organic light-emitting device according to any one of [1] to [4], wherein at least one of $R^{31}$ to $R^{35}$ in the general formula (2) is a carbazol-9-yl group substituted at least at any one of the 3-position or 6-position.

[6] The organic light-emitting device according to any one of [1] to [5], wherein the carbazol-9-yl group in the general formula (2) is unsubstituted, or substituted with a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group.

[7] The organic light-emitting device according to [6], wherein the compound represented by the general formula (2) is a compound represented by the following general formula (2a).

General Formula (2a)

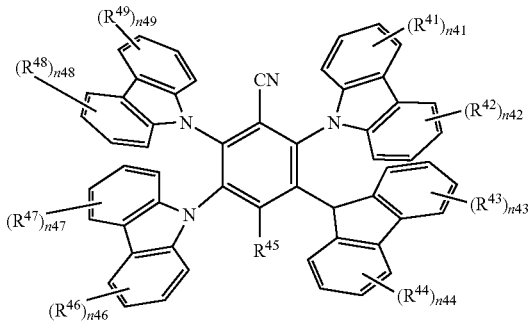

In the general formula (2a), $R^{41}$ to $R^{44}$, and $R^{46}$ to $R^{49}$ each independently represent a substituent, but all the four substituted or unsubstituted carbazol-9-yl groups bonding to benzonitrile in the general formula (2a) are not the same; n41 to n44, and n46 to n49 each independently represent an integer of any of 0 to 4, $R^{45}$ represents a hydrogen atom, a substituted or unsubstituted aryl group, a substituted or unsubstituted carbazol-9-yl group, or a cyano group.

[8] The organic light-emitting device according to any one of [1] to [7], containing the compound represented by the general formula (1) in the light-emitting layer.

[9] The organic light-emitting device according to any one of [1] to [8], containing the compound represented by the general formula (1) and the compound represented by the general formula (2) in the same layer.

[10] A composition containing both a compound represented by the general formula (1) and a compound represented by the general formula (2).

[11] A film containing both a compound represented by the general formula (1) and a compound represented by the general formula (2).

Advantageous Effects of Invention

The organic light-emitting device of the present invention contains both a compound represented by the general formula (1) and a compound represented by the general formula (2), and therefore has a high light emission efficiency. According to the present invention, a blue light-emitting device having a high light emission efficiency can be realized.

BRIEF DESCRIPTION OF DRAWINGS

FIG. 1 This is a schematic cross-sectional view showing a layer configuration example of an organic electroluminescent device.

FIG. 2 This shows an absorption spectrum of a compound 1, and emission spectra of the compound 1, compounds 2 to 38, and Example 1.

FIG. 3 This shows transient decay curves of a device of Example 2, a comparative device 1 and a comparative device 2.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the numerical values described before and after "to" as the upper limit and the lower limit. The hydrogen atom that is present in the molecule of the compound used in the invention is not particularly limited in isotope species, and for example, all the hydrogen atoms in the molecule may be $^1$H, and all or a part of them may be $^2$H (deuterium (D)).

<Compound Represented by General Formula (1)>

The present invention uses a compound having one or more structures represented by the following general formula (1).

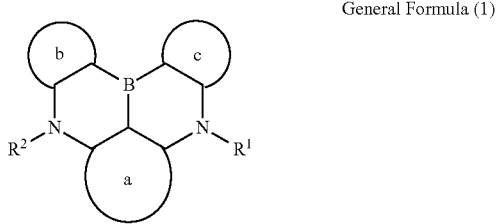

General Formula (1)

In the general formula (1), the ring a, the ring b and the ring c each independently represent a benzene ring that may be condensed with any other ring to form an aryl ring or a heteroaryl ring, and at least one hydrogen atom in these rings may be substituted; $R^1$ and $R^2$ each independently represent a substituted or unsubstituted aryl group, or a substituted or unsubstituted heteroaryl group bonding via the benzene ring; $R^1$ may bond to the carbon atom neighboring to the bonding position (atom) to N in the ring a and/or the ring c via —O—, —S—, —C(—R$^{c1}$)$_2$— or a single bond; $R^2$ may bond to the carbon atom neighboring to the bonding position (atom) to N in the ring a and/or the ring b via —O—, —S—, —C(—R$^{c2}$)$_2$— or a single bond; $R^{11}$ and $R^{c2}$ each independently represent a hydrogen atom or an alkyl group.

The ring a, the ring b and the ring c each may be a monocyclic ring or a polycyclic ring, but the ring directly bonding to B and N shown in the general formula (1) is a benzene ring. When the benzene ring directly bonding to B and N is condensed with any other ring to form a polycyclic ring, the polycyclic ring to be formed is an aryl ring or a heteroaryl ring. The aryl ring as referred to herein has a carbon number of preferably 6 to 30, more preferably 6 to 16, even more preferably 6 to 12, further more preferably 6 to 10. The heteroaryl ring as referred to herein has a carbon number of preferably 6 to 30, more preferably 6 to 25, even more preferably 6 to 20, further more preferably 6 to 15, especially more preferably 6 to 10. Preferably, the hetero ring to constitute the heteroaryl ring is a 5- to 7-membered ring, more preferably a 5- or 6-membered ring. The ring-forming atom of the hetero ring includes, in addition to a carbon atom, 1 to 5 hetero atoms selected from the group consisting of an oxygen atom, a sulfur atom and a nitrogen atom. The aryl ring or the heteroaryl ring to be formed by condensation includes a naphthalene ring, an acenaphthylene ring, a fluorene ring, a phenalene ring, a phenanthrene ring, a triphenylene ring, a pyrene ring, a naphthacene ring, a perylene ring, a pentacene ring, an indole ring, an isoindole ring, a 1H-indazole ring, a benzimidazole ring, a benzoxazole ring, a benzothiazole ring, a 1H-benzotriazole ring, a quinoline ring, an isoquinoline ring, a cinnoline ring, a quinazoline ring, a quinoxaline ring, a phthalazine ring, a naphthyridine ring, a carbazole ring, an acridine ring, a phenoxathiin ring, a phenoxazine ring, a phenothiazine ring, a phenazine ring, a benzofuran ring, an isobenzofuran ring, a dibenzofuran ring, a benzothiophene ring, a dibenzothiophene ring, and a thianthrene ring.

The aryl group that $R^1$ and $R^2$ can represent is, for example, an aryl group having 6 to 30 carbon atoms, and is preferably an aryl group having 6 to 16 carbon atoms, more preferably an aryl group having 6 to 12 carbon atoms, even more preferably an aryl group having 6 to 10 carbon atoms. The aryl ring to constitute the aryl group includes a benzene ring, a naphthalene ring, an acenaphthylene ring, a fluorene ring, a phenalene ring, a phenanthrene ring, a triphenylene ring, a pyrene ring, a naphthacene ring, a perylene ring, and a pentacene ring.

The heteroaryl group that $R^1$ and $R^2$ can represent has a polycyclic structure condensed at least with a benzene ring, and each are a group bonding via the benzene ring that constitutes the polycyclic structure. Regarding the description and the preferred range of the heteroaryl ring to constitute the heteroaryl group that $R^1$ and $R^2$ can represent, reference may be made to the description and the preferred range of the heteroaryl ring that the ring a, the ring b and the ring c can represent.

$R^1$ can bond to the carbon atom neighboring to the bonding position (atom) to N in the ring a and/or the ring c via —O—, —S—, —C(—R$^{c1}$)$_2$— or a single bond. $R^2$ can bond to the carbon atom neighboring to the bonding position (atom) to N in the ring a and/or the ring b via —O—, —S—, —C(—R$^{c2}$)$_2$— or a single bond. As referred to herein, the carbon atom neighboring to the bonding position (atom) to N is the carbon atom not bonding to B. R and $R^2$ each independently represent a hydrogen atom or an alkyl group. Here, the alkyl group is preferably one having 1 to 4 carbon atoms, and examples thereof include a methyl group and an ethyl group. Examples of the cyclic structure to be formed by $R^1$ or $R^2$ bonding to the ring a, the ring b and/or the ring c via —O—, —S—, —C(—R$^{c1}$)$_2$—, —C(—R$^{c2}$)$_2$— or a single bond include a phenoxazine ring, a phenothiazine ring, an acridine ring, and a carbazole ring.

The substituent of the substituted aryl group or the substituted heteroaryl group that may be represented by $R^1$ and $R^2$, and the substituent of the substituted ring a, the substituted ring b and the substituted ring c each are preferably a halogen atom, a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group (amino group having an aryl group and a heteroaryl group), a substituted or unsubstituted alkyl group, a substituted or unsubstituted alkoxy group, or a substituted or unsubstituted aryloxy group. In the case where these groups have a substituent, the substituent includes an aryl group, a heteroaryl group and an alkyl group. The total number of the substituents that $R^1$, $R^2$, the ring a, the ring b and the ring c can have is preferably 0 to 10, and can be selected from 1 to 10, or from 2 to 10, or from 0 to 6, or from 0 to 2.

The halogen atom that can be taken as a substituent is a fluorine atom, a chlorine atom, a bromine atom or an iodine atom, preferably a fluorine atom, a chlorine atom or a bromine atom, more preferably a chlorine atom.

The aryl group that can be taken as a substituent, or the aryl group contained in the diarylamino group, the arylheteroarylamino group or the aryloxy group that can be taken as a substituent is, for example, an aryl group having 6 to 30 carbon atoms, preferably an aryl group having 6 to 16 carbon atoms, more preferably an aryl group having 6 to 12 carbon atoms, even more preferably an aryl group having 6 to 10 carbon atoms. The aryl ring to constitute the aryl group includes a monocyclic benzene ring, a condensed bicyclic naphthalene ring, a condensed tricyclic acenaphthylene ring, fluorene ring, phenalene ring or phenanthrene ring, a condensed tetracyclic triphenylene ring, pyrene ring or naphthacene ring, and a condensed pentacyclic perylene ring or pentacene ring. As will be described below, the aryl group may be further substituted with an aryl group, and for example, the substituted aryl group can also be a tricyclic terphenyl ring (m-terphenyl, p-terphenyl, p-terphenyl).

The heteroaryl group that can be taken as a substituent, or the heteroaryl group contained in the diheteroarylamino group and the arylheteroarylamino group that can be taken as a substituent is, for example, a heteroaryl group having 2 to 30 carbon atoms, preferably a heteroaryl group having 2 to 25 carbon atoms, more preferably a heteroaryl group having 2 to 20 carbon atoms, even more preferably a heteroaryl group having 2 to 15 carbon atoms, further more preferably a heteroaryl group having 2 to 10 carbon atoms. The heteroaryl ring to constitute the heteroaryl group is, for example, a hetero ring that contains 1 to 5 hetero atoms selected from an oxygen atom, a sulfur atom and a nitrogen atom in addition to a carbon atom as the ring-forming atoms. Examples of the heteroaryl ring to constitute the heteroaryl group include a pyrrole ring, an oxazole ring, an isoxazole ring, a thiazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzoxazole ring, a benzothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazan ring, an oxadiazole ring, and a thianthrene ring.

The alkyl group that can be taken as a substituent may be linear, branched or cyclic, and examples thereof include a linear alkyl group having 1 to 24 carbon atoms, a branched alkyl group having 3 to 24 carbon atoms, and a cyclic alkyl group having 3 to 8 carbon atoms. A linear alkyl group having 1 to 18 carbon atoms, a branched alkyl group having 3 to 18 carbon atoms or a cyclic alkyl group having 4 to 8 carbon atoms is preferred; a linear alkyl group having 1 to 12 carbon atoms, a branched alkyl group having 3 to 12 carbon atoms or a cyclic alkyl group having 5 to 7 carbon atoms is more preferred; a linear alkyl group having 1 to 6 carbon atoms, a branched alkyl group having 3 to 6 carbon atoms or a cyclic alkyl group having 5 to 6 carbon atoms is even preferred; and a linear alkyl group having 1 to 4 carbon atoms, or a branched alkyl group having 3 or 4 carbon atoms is especially more preferred. Specific examples of the alkyl group include a methyl group, an ethyl group, an n-propyl group, an isopropyl group, an n-butyl group, an isobutyl group, a s-butyl group, a t-butyl group, an n-pentyl group, an isopentyl group, a neopentyl group, a t-pentyl group, an n-hexyl group, a 1-methylpentyl group, a 4-methyl-2-pentyl group, a 3,3-dimethylbutyl group, a 3-ethylbutyl group, an n-heptyl group, a 1-methylhexyl group, an n-octyl group, a t-octyl group, a 1-methylheptyl group, a 2-ethylhexyl group, a 2-propylpentyl group, an n-nonyl group, a 2,2-dimethylheptyl group, a 2,6-dimethyl-4-heptyl group, a 3,5,5-trimethylhexyl group, an n-decyl group, an n-undecyl group, a 1-methyldecyl group, an n-dodecyl group, an n-tridecyl group, a 1-hexylheptyl group, an n-tetradecyl group, an n-pentadecyl group, an n-hexadecyl group, an n-heptadecyl group, an n-octadecyl group, an n-eicosyl group, a cyclopropyl group, a cyclobutyl group, a cyclopentyl group, a cyclohexyl group, a cycloheptyl group, a cyclooctyl group, a bicyclo[2.2.1]heptyl group, a bicyclo[2.2.2]octyl group, a decahydronaphthyl group, and an adamantyl group. In this description, "n" is an abbreviation of normal, "s" is secondary, and "t" is tertiary.

The alkoxy group that can be taken as a substituent is, for example, a linear alkoxy group having 1 to 24 carbon atoms, a branched alkoxy group having 3 to 24 carbon atoms, or a cyclic alkoxy group having 3 to 8 carbon atoms. A linear alkoxy group having 1 to 18 carbon atoms, a branched alkoxy group having 3 to 18 carbon atoms, and a cyclic alkoxy group having 4 to 8 carbon atoms are preferred; a linear alkoxy group having 1 to 12 carbon atoms, a branched alkoxy group having 3 to 12 carbon atoms, and a cyclic alkoxy group having 5 to 7 carbon atoms are more preferred; a linear alkoxy group having 1 to 6 carbon atoms, a branched alkoxy group having 3 to 6 carbon atoms, and a cyclic alkoxy group having 5 to 6 carbon atoms are even more preferred; a linear alkoxy group having 1 to 4 carbon atoms, and a branched alkoxy group having 3 to 4 carbon atoms are especially more preferred. Specific examples of the alkoxy group include a methoxy group, an ethoxy group, a propoxy group, an isopropoxy group, a butoxy group, an isobutoxy group, a s-butoxy group, a t-butoxy group, a pentyloxy group, a hexyloxy group, a heptyloxy group, an octyloxy group, a cyclohexyloxy group, a bicyclo[2.2.1]heptyloxy group, a bicyclo[2.2.2]octyloxy group, a decahydronaphthyloxy group, and an adamantyloxy group.

The two aryl groups constituting the diarylamino group, the two heteroaryl groups constituting the diheteroarylamino group, and the aryl group and the heteroaryl group constituting the arylheteroarylamino group, which can be taken as a substituent, each may bond to each other via a single bond or a linking group, or may not bond. The number of the linking chain-forming atoms of the linking group is preferably 1 to 3, more preferably 1 or 2, even more preferably 1. The linking group includes —O—, —S—, —C(=O)—, —C(=S)—, —N($R^{51}$)—, —B($R^{52}$)—, —C($R^{53}$)($R^{54}$)—, —Si($R^{55}$)($R^{56}$)—, and a linking group formed by linking two or more of these. Here, $R^{51}$ to $R^{56}$ each independently represent a hydrogen atom or a substituent; and preferred examples of the substituent include a substituted or unsubstituted alkyl group (preferably having 1 to 20 carbon atoms, more preferably 1 to 10 carbon atoms, even more preferably 1 to 6 carbon atoms), a substituted or unsubstituted aryl group (preferably having 6 to 20 carbon atoms, more preferably 6 to 14 carbon atoms, even more preferably 6 to 10 carbon atoms), and a substituted or unsubstituted heteroaryl group (in which the number of the ring skeleton-forming atoms is preferably 5 to 20, more preferably 5 to 14, even more preferably 5 to 10).

The compound having plural structures represented by the general formula (1) is a multimer of the structure represented by the general formula (1). The multimer is preferably a di- to hexamer, more preferably a di- to trimer, and even more preferably a dimer. The multimer may have any form having plural structures represented by the general formula (1) in one compound, and includes, for example, a form having the above-mentioned structures bonding via a single bond or a linking group such as an alkylene group having 1 to 3 carbon, or a phenylene group or a naphthylene group, and also a form of plural structures of the general formula (1) bonding to each other in such a manner that any ring (the ring a, the ring b or the ring c) contained in the structure is shared by those plural structures, and a form of plural structures of the general formula (1) bonding to each other in such a manner that any rings (the ring a, the ring b or the ring c) contained in the structure are condensed with each other.

A preferred compound group represented by the general formula (1) is, for example, a compound group represented by the following general formula (1a).

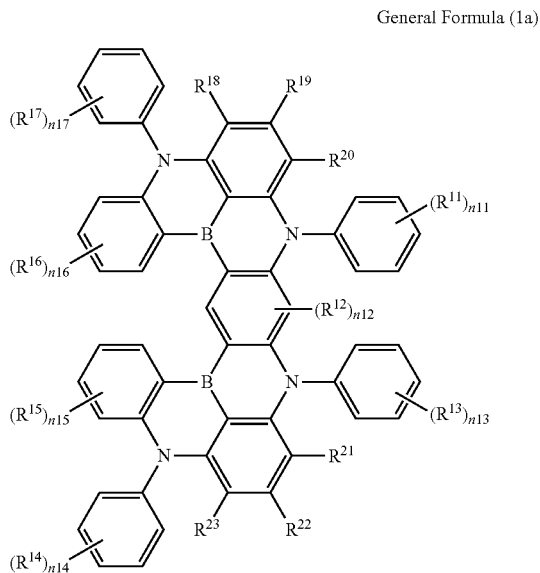

General Formula (1a)

In the general formula (1a), $R^{11}$ to $R^{17}$ each independently represent a substituent, $R^{18}$ to $R^{23}$ each independently represent a hydrogen atom or a substituent, n11, n13, n14 and n17 each independently represent an integer of any of 0 to 5, n12 represents an integer of any of 0 to 2, n15 and n16 each independently represent an integer of any of 0 to 4.

Preferably, the substituent that $R^{11}$ to $R^{23}$ in the general formula (1a) can represent is a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group (amino group having an aryl group and a heteroaryl group), a substituted or unsubstituted alkyl group, a substituted or unsubstituted alkoxy group, or a substituted or unsubstituted aryloxy group. In the case where these groups have a substituent, the substituent includes an aryl group, a heteroaryl group and an alkyl group. Here, regarding the aryl group, the heteroaryl group, the diarylamino group, the diheteroarylamino group, the arylheteroarylamino group, the alkyl group, the alkoxy group and the aryloxy group, reference may be made to the description relating to these groups in the general formula (1).

$R^{14}$ bonding to a 2-position of the benzene ring and $R^{11}$ bonding to a 2-position of the benzene ring may bond to each other to form a single bond or a linking group (here, the 1-position of the benzene ring is a position bonding to the nitrogen atom N expressed in the general formula (1a)). Also, $R^{16}$ bonding to a 2-position of the benzene ring and $R^{11}$ bonding to a 2-position of the benzene ring may bond to each other to form a single bond or a linking group (here, the 1-position of the benzene ring is a position bonding to the nitrogen atom N expressed in the general formula (1a)). Regarding the linking group as referred to herein, reference may be made to the description relating to the linking group in the general formula (1).

n11, and n13 to n17 in the general formula (1a) each are preferably an integer of any of 0 to 3, more preferably an integer of any of 0 to 2.

In the compound represented by the general formula (1a), the number of the substituents existing as $R^{11}$ to $R^{23}$ is preferably 0 to 26, more preferably 0 to 16, and may be selected from 1 to 8, or from 2 to 8, or from 0 to 4, or from 0 to 2.

A preferred compound group represented by the general formula (1a) is a compound group where $R^{11}$, $R^{20}$, $R^{21}$ and $R^{23}$ are hydrogen atoms; and a more preferred compound group is a compound group where $R^{11}$, $R^{20}$, $R^{21}$ and $R^{23}$ are hydrogen atoms, and n11 to n17 each are independently an integer of any of 0 to 2.

Another preferred compound group represented by the general formula (1a) is a compound group where $R^{11}$ to $R^{23}$ each are a hydrogen atom, a substituted or unsubstituted aryl group, a substituted or unsubstituted diarylamino group, a substituted or unsubstituted alkyl group, a substituted or unsubstituted alkoxy group, or a substituted or unsubstituted aryloxy group.

Still another preferred compound group represented by the general formula (1a) is a compound group where $R^{19}$ and $R^{22}$ each are a substituent; and a more preferred compound group is a compound group where $R^{19}$ and $R^{22}$ each are a substituted or unsubstituted aryl group, a substituted or unsubstituted heteroaryl group, a substituted or unsubstituted diarylamino group, a substituted or unsubstituted alkyl group, a substituted or unsubstituted alkoxy group, or a substituted or unsubstituted aryloxy group. In the case where these groups have a substituent, the substituent includes an aryl group, a heteroaryl group and an alkyl group.

A preferred compound group represented by the general formula (1) is, for example, a compound group represented by the following general formula (1b).

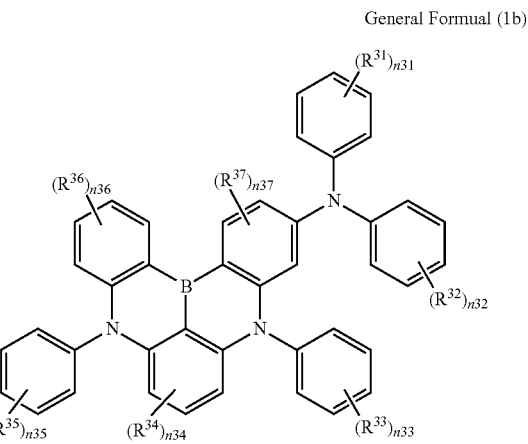

General Formual (1b)

In the general formula (1b), $R^{31}$ to $R^{37}$ each independently represent a substituent, n31 to n33, and n35 each independently represent an integer of any of 0 to 5, n34 and n37 each independently represent an integer of any of 0 to 3, n36 represents an integer of any of 0 o 4.

The substituent that $R^{31}$ to $R^{37}$ in the general formula (1b) can represent is preferably a substituted or unsubstituted aryl group or a substituted or unsubstituted alkyl group. In the case where these aryl group and alkyl group have a substituent, the substituent includes an aryl group and an alkyl group. Here, regarding the aryl group and the alkyl group, reference may be made to the description relating to these groups in the general formula (1). In particular, the carbon number of the alkyl group that $R^{31}$ to $R^{37}$ in the general formula (1b) can represent is preferably 1 to 12, more preferably 1 to 4. Also in particular, the aryl group that $R^{31}$ to $R^{37}$ in the general formula (1b) can represent is preferably an aryl group having 6 to 10 carbon atoms, more preferably a phenyl group.

n31 to n37 in the general formula (1b) is preferably an integer of any of 0 to 2, more preferably an integer of any of 0 to 1.

The total of n31 to n37 in the general formula (1b) is preferably 0 to 14, more preferably 0 to 8, and, for example, can be selected from 1 to 8, or from 2 to 8, or from 0 to 4, or from 0 to 2.

A preferred compound group represented by the general formula (1b) is a compound group where $R^{31}$ to $R^{37}$ each are a substituted or unsubstituted phenyl group, and a more preferred compound group is a compound group where $R^{31}$ to $R^{37}$ each are an unsubstituted phenyl group.

Another preferred compound group represented by the general formula (1b) includes a compound group where n35 is an integer of any of 1 to 5, a compound group where n35 is an integer of any of 1 to 3, and a compound group where n35 is 1 and $R^{35}$ is a substituted or unsubstituted phenyl group. Also a compound group where n36 is an integer of any of 1 to 4, a compound group where n36 is an integer of any of 1 to 3, and a compound group where n36 is 1 and $R^{36}$ is a substituted or unsubstituted phenyl group are also preferred. Further, a compound group where n35 and n36 each are independently an integer of any of 1 to 3, a compound group where n35 and n36 are 1, a compound group where n35 and n36 are 1 and $R^{35}$ and $R^{36}$ each are independently a substituted or unsubstituted phenyl group are also preferred.

The compounds represented by the general formula (1) and the general formula (1a) can be synthesized with reference to the description of paragraphs [0281] to [0316] and Synthesis Examples in JP 5935199. The compounds can also be synthesized by combination of known synthesis methods. Regarding a specific synthesis route of those compounds, reference may be made to Synthesis Example 1 given hereinunder.

Examples of the compounds represented by the general formula (1) are shown below, but the compounds employable in the present invention should not be limitatively interpreted by the following examples.

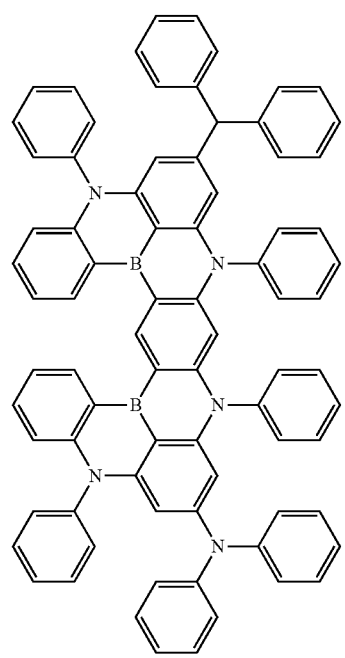

Compound 1

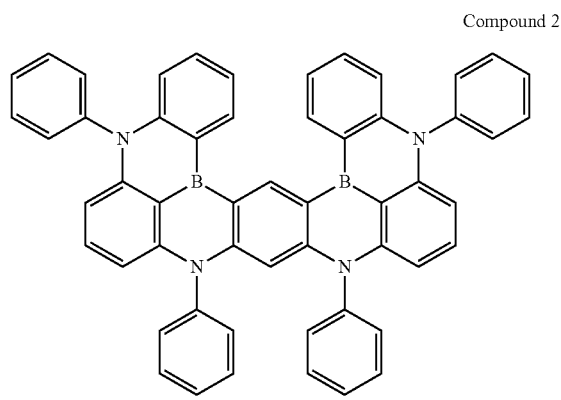

Compound 2

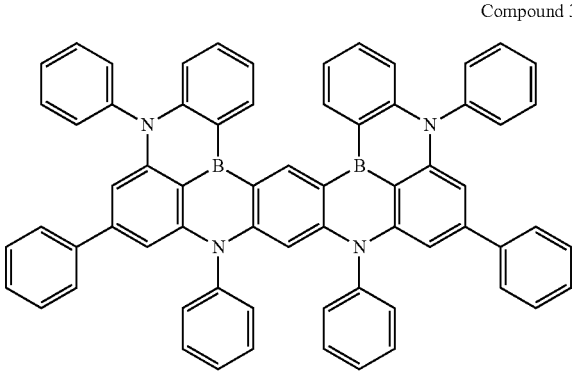

Compound 3

Compound 4

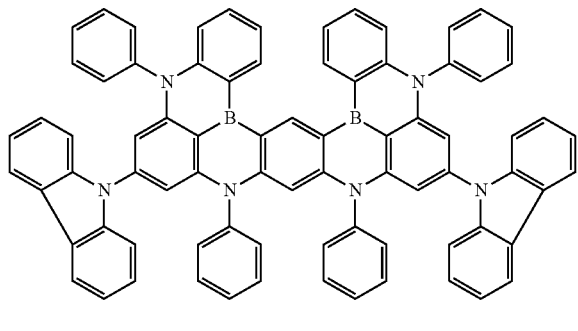

Compound 8

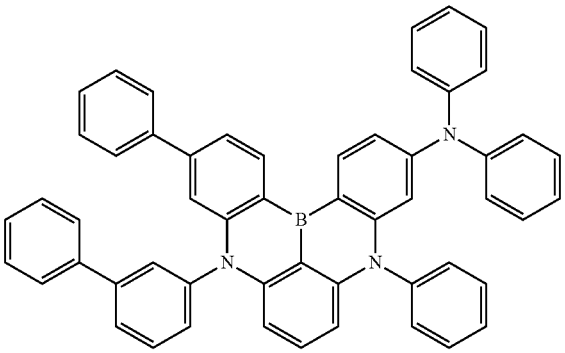

Compound 5

Compound 6

Compound 7

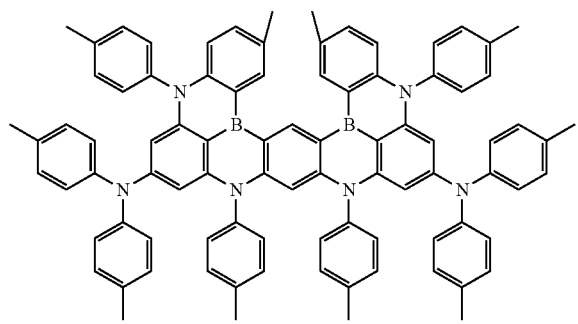

<Compound Represented by General Formula (2)>

The present invention uses a compound represented by the following general formula (2).

General Formula (2)

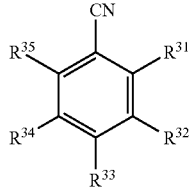

In the general formula (2), four of $R^{31}$ to $R^{35}$ each independently represent a substituted or unsubstituted carbazol-9-yl group, but all of these four are not the same, and the remaining one represents a hydrogen atom, a substituted or unsubstituted aryl group, a substituted or unsubstituted carbazol-9-yl group, or a cyano group.

The substituent of the carbazol-9-yl group that $R^{31}$ to $R^{35}$ can represent is preferably a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group. These groups can be substituted with these substituents.

Here, regarding the aryl group, the heteroaryl group, the diarylamino group, the diheteroarylamino group, the arylheteroarylamino group, the alkyl group, the alkoxy group and the aryloxy group, reference may be made to the description relating to these groups in the general formula (1).

In the case where the carbazol-9-yl group that $R^{31}$ to $R^{35}$ can represent is substituted, the bonding position of the substituent is preferably a 3-position, or both a 3-position and a 6-position of the carbazole ring.

Specific examples of the carbazol-9-yl group that $R^{31}$ to $R^{35}$ can represent include a 3-methylcarbazol-9-yl group, a 3,6-dimethylcarbazol-9-yl group, a 3-ethylcarbazol-9-yl group, a 3,6-diethylcarbazol-9-yl group, a 3-t-butylcarbazol-9-yl group, a 3,6-di-t-butylcarbazol-9-yl group, a 3-phenylcarbazol-9-yl group, a 3,6-diphenylcarbazol-9-yl group, a 3-(carbazol-9-yl)carbazol-9-yl group, and a 3,6-bis(carbazol-9-yl)carbazol-9-yl group.

Four of $R^{31}$ to $R^{35}$ each independently represent a substituted or unsubstituted carbazol-9-yl group, but all of these four are not the same. All four may differ, but preferably, three are the same and one differs, or two are the same and the other two are the same. For example, a case where $R^{31}$ and $R^{35}$ are the same and $R^{32}$ and $R^{34}$ are the same, a case where $R^{31}$ and $R^{32}$ are the same and $R^{34}$ and $R^{35}$ are the same, a case where $R^{31}$ and $R^{34}$ are the same and $R^{32}$ and $R^{35}$ are the same, a case where $R^{32}$ and $R^{34}$ and $R^{35}$ are the same and $R^{31}$ alone differs, and a case where $R^{31}$ and $R^{34}$ and $R^{35}$ are the same and $R^{32}$ alone differs are exemplified.

The difference in the substituted or unsubstituted carbazol-9-yl group in the general formula (2) may be a difference whether the carbazol-9-yl group has a substituent or does not have a substituent, or a difference in the kind of the substituent bonding to the carbazol-9-yl group, or a difference in the bonding position of the substituent bonding to the carbazol-9-yl group. Preferred is a difference whether the carbazol-9-yl group has a substituent or does not have a substituent, or a difference in the kind of the substituent bonding to the carbazol-9-yl group. An example of the difference in the kind of the substituent bonding to the carbazol-9-yl group is a carbazol-9-yl group substituted with an alkyl group and a carbazol-9-yl group substituted with an aryl group. An example of the difference in the bonding position of the substituent bonding to the carbazol-9-yl group is a carbazol-9-yl group substituted with an alkyl group at the 3-position and the 6-position, and a carbazol-9-yl group substituted with an alkyl group at the 3-position alone.

The remaining one of $R^{31}$ to $R^{35}$ represents a hydrogen atom, a substituted or unsubstituted aryl group, a substituted or unsubstituted carbazol-9-yl group, or a cyano group. When the remaining one represents a substituted or unsubstituted carbazol-9-yl group, the substituted or unsubstituted carbazol-9-yl group may be the same as at least one of the other four, or may differ from the other four. Regarding the aryl group that the remaining one of $R^{31}$ to $R^{35}$ can represent, reference may be made to the description of the aryl group in the general formula (1). The aryl group that the remaining one of $R^{31}$ to $R^{35}$ can represent may be substituted, and the substituent is preferably an alkyl group or an aryl group. The aryl group that the remaining one of $R^{31}$ to $R^{35}$ can represent is, for example, a phenyl group substituted with an alkyl group or an aryl group at the 4-position, or a phenyl group substituted with an alkyl group or an aryl group at the 3-position and the 5-position. When the remaining one is a hydrogen atom, a substituted or unsubstituted aryl group, or a cyano group, it may be any of $R^{31}$ to $R^{35}$, but is preferably $R^{33}$.

A preferred compound group represented by the general formula (2) is, for example, a compound group represented by the following general formula (2a).

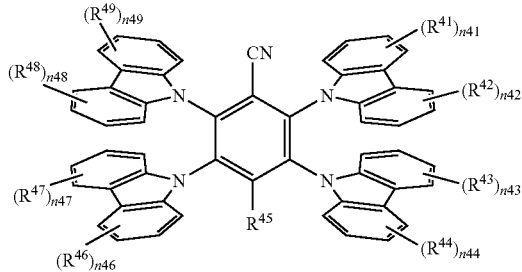

General Formula (2a)

In the general formula (2a), $R^{41}$ to $R^{44}$, and $R^{46}$ to $R^{49}$ each independently represent a substituent, but all the four substituted or unsubstituted carbazol-9-yl groups bonding to benzonitrile in the general formula (2a) are not the same; n41 to n44, and n46 to n49 each independently represent an integer of any of 0 to 4, $R^{45}$ represents a hydrogen atom, a substituted or unsubstituted aryl group, a substituted or unsubstituted carbazol-9-yl group, or a cyano group.

Regarding the substituent that $R^{41}$ to $R^{44}$, and $R^{46}$ to $R^{49}$ can represent, reference may be made to the description of the substituent of the carbazol-9-yl group that $R^{31}$ to $R^{35}$ in the general formula (2) can represent. Regarding the group that $R^{45}$ can represent, reference may be made to the description of the group that the remaining one of $R^{31}$ to $R^{35}$ in the general formula (2) can represent.

When n41 is 2 or more, plural $R^{41}$'s may be the same as or different from each other, and neighboring two $R^{41}$'s may or may not bond to form a cyclic structure. When n42 is 2 or more, plural $R^{42}$'s may be the same as or different from each other, and neighboring two $R^{42}$'s may or may not bond to form a cyclic structure. When n43 is 2 or more, plural $R^{43}$'s may be the same as or different from each other, and neighboring two $R^{43}$'s may or may not bond to form a cyclic structure. When n44 is 2 or more, plural $R^{44}$'s may be the same as or different from each other, and neighboring two $R^{44}$'s may or may not bond to form a cyclic structure. When n46 is 2 or more, plural $R^{46}$'s may be the same as or different from each other, and neighboring two $R^{46}$'s may or may not bond to form a cyclic structure. When n47 is 2 or more, plural $R^{47}$'s may be the same as or different from each other, and neighboring two $R^{47}$'s may or may not bond to form a cyclic structure. When n48 is 2 or more, plural $R^{48}$'s may be the same as or different from each other, and neighboring two $R^{48}$'s may or may not bond to form a cyclic structure. When n49 is 2 or more, plural $R^{49}$'s may be the same as or different from each other, and neighboring two $R^{49}$'s may or may not bond to form a cyclic structure. Regarding the cyclic structure as referred to herein, reference may be made to the description of the cyclic structure in the general formula (1).

Preferably, n41 to n49 each are an integer of any of 0 to 3, more preferably an integer of any of 0 to 2. The total of n41 to n49 is preferably 1 to 24, more preferably 1 to 16, even more preferably 1 to 8.

Examples of the combination of n41 to n44, and n46 to n49 include a case where n41 alone is 1, and the others are 0; a case where n43 alone is 1, and the others are 0; a case where n41 and n42 are 1, and the others are 0; a case where n43 and n44 are 1, and the others are 0; a case where n41 and n43 are 1, and the others are 0; a case where n41 and n46 are 1, and the others are 0, a case where n41 and n48 are 1, and the others are 0; a case where n41 to n44 are 1, and the others are 0; a case where n41, n42, n46 and n47 are 1, and the others are 0; a case where n43, n44, n46 and n47 are 1, and the others are 0; a case where n41 and n42 are 0, and the others are 1; a case where n43 and n44 are 0, and the others are 1.

The compounds represented by the general formula (2) and the general formula (2a) can be synthesized with reference to Synthesis Example 2 to be mentioned hereinunder. Specifically, the compounds can be synthesized by reacting a 4-phenyl-2,3,5,6-tetrafluorobenzonitrile with a substituted or unsubstituted carbazol to introduce a substituted or unsubstituted carbazol-9-yl group into the 2-position and the 6-position of the benzonitrile, followed by further reacting it with a substituted or unsubstituted diarylcarbazole to introduce a substituted or unsubstituted diarylcarbazol-9-yl group into the 3-position and the 5-position thereof. Also the compounds can be synthesized by combining known synthesis methods.

Specific examples of the compounds represented by the general formula (2) are shown in the following Table 1 and Table 2, but the compounds employable in the present invention should not be limitatively interpreted by the following examples. A general formula (3a) and a general formula (3b) representing the substituent in the general formula (2) are also shown below.

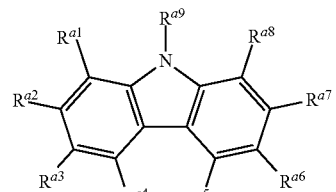

General Formula (3a)

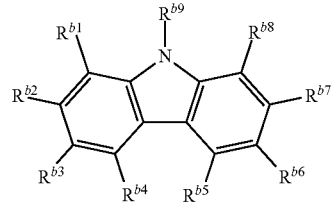

General Formula (3b)

TABLE 1

| Compound No. | General formula (2) | | | | | General formula (3a) | | | | | | |
|---|---|---|---|---|---|---|---|---|---|---|---|---|
| | $R^{31}$ | $R^{32}$ | $R^{33}$ | $R^{34}$ | $R^{35}$ | $R^{a1}$ | $R^{a2}$ | $R^{a3}$ | $R^{a4}$ | $R^{a5}$ | $R^{a6}$ | $R^{a7}$ |
| 2-1 | General formula (3a) | General formula (3b) | General formula (3a) | General formula (3b) | General formula (3a) | H | H | H | H | H | H | H |
| 2-2 | General formula (3a) | General formula (3b) | General formula (3a) | General formula (3b) | General formula (3a) | H | H | H | H | H | H | H |
| 2-3 | General formula (3a) | General formula (3b) | General formula (3a) | General formula (3b) | General formula (3a) | H | H | H | H | H | H | H |
| 2-4 | General formula (3a) | General formula (3b) | General formula (3a) | General formula (3b) | General formula (3a) | H | H | H | H | H | H | H |
| 2-5 | General formula (3a) | General formula (3a) | General formula (3a) | General formula (3b) | General formula (3a) | H | H | H | H | H | H | H |
| 2-6 | General formula (3a) | General formula (3a) | General formula (3a) | General formula (3b) | General formula (3a) | H | H | H | H | H | H | H |
| 2-7 | General formula (3a) | General formula (3b) | General formula (3a) | General formula (3b) | General formula (3a) | H | H | H | H | H | H | H |
| 2-8 | General formula (3a) | General formula (3b) | General formula (3a) | General formula (3b) | General formula (3a) | H | H | H | H | H | H | H |
| 2-9 | General formula (3a) | General formula (3b) | General formula (3a) | General formula (3b) | General formula (3a) | H | H | H | H | H | H | H |
| 2-10 | General formula (3a) | General formula (3b) | General formula (3a) | General formula (3b) | General formula (3a) | H | H | H | H | H | H | H |
| 2-11 | General formula (3a) | General formula (3b) | General formula (3a) | General formula (3b) | General formula (3a) | H | H | H | H | H | H | H |
| 2-12 | General formula (3a) | General formula (3b) | General formula (3a) | General formula (3b) | General formula (3a) | H | H | H | H | H | H | H |
| 2-13 | General formula (3a) | General formula (3b) | General formula (3a) | General formula (3b) | General formula (3a) | H | H | H | H | H | H | H |
| 2-14 | General formula (3a) | General formula (3b) | General formula (3a) | General formula (3b) | General formula (3a) | H | H | H | H | H | H | H |
| 2-15 | General formula (3a) | General formula (3b) | General formula (3a) | General formula (3b) | General formula (3a) | H | H | H | H | H | H | H |
| 2-16 | General formula (3a) | General formula (3b) | General formula (3a) | General formula (3b) | General formula (3a) | H | H | H | H | H | H | H |
| 2-17 | General formula (3a) | General formula (3b) | General formula (3a) | General formula (3b) | General formula (3a) | H | H | $CH_3$ | H | H | $CH_3$ | H |
| 2-18 | General formula (3a) | General formula (3b) | General formula (3a) | General formula (3b) | General formula (3a) | H | H | $CH_3$ | H | H | $CH_3$ | H |
| 2-19 | General formula (3a) | General formula (3b) | General formula (3a) | General formula (3b) | General formula (3a) | H | H | $CH_3$ | H | H | $CH_3$ | H |
| 2-20 | General formula (3a) | General formula (3b) | General formula (3a) | General formula (3b) | General formula (3a) | H | H | tert-$C_4H_9$ | H | H | tert-$C_4H_9$ | H |
| 2-21 | General formula (3a) | General formula (3b) | General formula (3a) | General formula (3b) | General formula (3a) | H | H | Phenyl | H | H | Phenyl | H |
| 2-22 | General formula (3a) | General formula (3b) | General formula (3a) | General formula (3b) | General formula (3a) | H | H | H | H | H | H | H |
| 2-23 | General formula (3a) | General formula (3b) | General formula (3a) | General formula (3b) | General formula (3a) | H | H | Phenyl | H | H | Phenyl | H |

TABLE 1-continued

| | | | | | | | | | | | | |
|---|---|---|---|---|---|---|---|---|---|---|---|---|
| 2-24 | General formula (3a) | General formula (3b) | General formula (3a) | General formula (3b) | General formula (3a) | H | H | H | H | H | H | H |
| 2-25 | General formula (3a) | General formula (3b) | General formula (3a) | General formula (3b) | General formula (3a) | H | H | H | H | H | H | H |
| 2-26 | General formula (3a) | General formula (3b) | General formula (3a) | General formula (3b) | General formula (3a) | H | H | H | H | H | H | H |
| 2-27 | General formula (3a) | General formula (3b) | General formula (3a) | General formula (3b) | General formula (3a) | H | H | H | H | H | H | H |
| 2-28 | General formula (3a) | General formula (3b) | General formula (3a) | General formula (3b) | General formula (3a) | H | H | H | H | H | H | H |
| 2-29 | General formula (3a) | General formula (3b) | General formula (3a) | General formula (3b) | General formula (3a) | H | H | H | H | H | H | H |
| 2-30 | General formula (3a) | General formula (3b) | General formula (3a) | General formula (3b) | General formula (3a) | H | H | H | H | H | H | H |
| 2-31 | General formula (3a) | General formula (3b) | General formula (3a) | General formula (3b) | General formula (3a) | H | H | H | H | H | H | H |
| 2-32 | General formula (3a) | General formula (3b) | General formula (3a) | General formula (3b) | General formula (3a) | H | H | H | H | H | H | H |
| 2-33 | General formula (3a) | General formula (3b) | General formula (3a) | General formula (3b) | General formula (3a) | H | H | H | H | H | H | H |
| 2-34 | General formula (3a) | General formula (3b) | General formula (3a) | General formula (3b) | General formula (3a) | H | H | H | H | H | H | H |
| 2-35 | General formula (3a) | General formula (3b) | Phenyl | General formula (3b) | General formula (3a) | H | H | H | H | H | H | H |
| 2-36 | General formula (3a) | General formula (3b) | Phenyl | General formula (3b) | General formula (3a) | H | H | H | H | H | H | H |
| 2-37 | General formula (3a) | General formula (3b) | Phenyl | General formula (3b) | General formula (3a) | H | H | H | H | H | H | H |
| 2-38 | General formula (3a) | General formula (3b) | Phenyl | General formula (3b) | General formula (3a) | H | H | H | H | H | H | H |
| 2-39 | General formula (3a) | General formula (3b) | Phenyl | General formula (3b) | General formula (3a) | H | H | H | H | H | H | H |
| 2-40 | General formula (3a) | General formula (3b) | Phenyl | General formula (3b) | General formula (3a) | H | H | H | H | H | H | H |
| 2-41 | General formula (3a) | General formula (3b) | Phenyl | General formula (3b) | General formula (3a) | H | H | H | H | H | H | H |
| 2-42 | General formula (3a) | General formula (3b) | Phenyl | General formula (3b) | General formula (3a) | H | H | H | H | H | H | H |
| 2-43 | General formula (3a) | General formula (3b) | Phenyl | General formula (3b) | General formula (3a) | H | H | H | H | H | H | H |
| 2-44 | General formula (3a) | General formula (3b) | Phenyl | General formula (3b) | General formula (3a) | H | H | H | H | H | H | H |
| 2-45 | General formula (3a) | General formula (3b) | Phenyl | General formula (3b) | General formula (3a) | H | H | $CH_3$ | H | H | $CH_3$ | H |
| 2-47 | General formula (3a) | General formula (3b) | Phenyl | General formula (3b) | General formula (3a) | H | H | $CH_3$ | H | H | $CH_3$ | H |
| 2-48 | General formula (3a) | General formula (3b) | Phenyl | General formula (3b) | General formula (3a) | H | H | Phenyl | H | H | Phenyl | H |
| 2-49 | General formula (3a) | General formula (3b) | Phenyl | General formula (3b) | General formula (3a) | H | H | Phenyl | H | H | Phenyl | H |
| 2-50 | General formula (3a) | General formula (3b) | Phenyl | General formula (3a) | General formula (3a) | H | H | H | H | H | H | H |
| 2-51 | General formula (3a) | General formula (3b) | Phenyl | General formula (3a) | General formula (3a) | H | H | H | H | H | H | H |
| 2-52 | General formula (3a) | General formula (3b) | Phenyl | General formula (3a) | General formula (3a) | H | H | H | H | H | H | H |
| 2-53 | General formula (3a) | General formula (3b) | H | General formula (3b) | General formula (3a) | H | H | H | H | H | H | H |
| 2-54 | General formula (3a) | General formula (3b) | H | General formula (3b) | General formula (3a) | H | H | H | H | H | H | H |
| 2-55 | General formula (3a) | General formula (3b) | H | General formula (3b) | General formula (3a) | H | H | H | H | H | H | H |
| 2-56 | General formula (3a) | General formula (3b) | H | General formula (3b) | General formula (3a) | H | H | H | H | H | H | H |
| 2-57 | General formula (3a) | General formula (3b) | H | General formula (3b) | General formula (3a) | H | H | H | H | H | H | H |
| 2-58 | General formula (3a) | General formula (3b) | H | General formula (3b) | General formula (3a) | H | H | H | H | H | H | H |
| 2-59 | CN | General formula (3a) | General formula (3a) | General formula (3b) | General formula (3b) | H | H | H | H | H | H | H |
| 2-60 | CN | General formula (3a) | General formula (3a) | General formula (3b) | General formula (3b) | H | H | H | H | H | H | H |
| 2-61 | CN | General formula (3a) | General formula (3a) | General formula (3b) | General formula (3b) | H | H | H | H | H | H | H |
| 2-62 | CN | General formula (3a) | General formula (3a) | General formula (3b) | General formula (3b) | H | H | $CH_3$ | H | H | $CH_3$ | H |
| 2-63 | CN | General formula (3a) | General formula (3b) | General formula (3a) | General formula (3b) | H | H | H | H | H | H | H |
| 2-64 | CN | General formula (3a) | General formula (3b) | General formula (3a) | General formula (3b) | H | H | H | H | H | H | H |

TABLE 1-continued

| | | | | | | | | | | | |
|---|---|---|---|---|---|---|---|---|---|---|---|
| 2-65 | CN | General formula (3a) | General formula (3b) | General formula (3a) | General formula (3b) | H | H | H | H | H | H | H |
| 2-66 | CN | General formula (3a) | General formula (3b) | General formula (3a) | General formula (3b) | H | H | CH$_3$ | H | H | CH$_3$ | H |
| 2-67 | CN | General formula (3a) | General formula (3b) | General formula (3b) | General formula (3a) | H | H | H | H | H | H | H |
| 2-68 | CN | General formula (3a) | General formula (3b) | General formula (3b) | General formula (3a) | H | H | H | H | H | H | H |
| 2-69 | CN | General formula (3a) | General formula (3b) | General formula (3b) | General formula (3a) | H | H | H | H | H | H | H |
| 2-70 | CN | General formula (3a) | General formula (3b) | General formula (3b) | General formula (3a) | H | H | CH$_3$ | H | H | CH$_3$ | H |
| 2-71 | CN | General formula (3a) | General formula (3b) | General formula (3b) | General formula (3a) | H | H | CH$_3$ | H | H | CH$_3$ | H |
| 2-72 | CN | General formula (3a) | General formula (3b) | General formula (3b) | General formula (3a) | H | H | CH$_3$ | H | H | CH$_3$ | H |
| 2-73 | CN | General formula (3a) | General formula (3b) | General formula (3b) | General formula (3a) | H | H | tert-C$_4$H$_9$ | H | H | tert-C$_4$H$_9$ | H |
| 2-74 | CN | General formula (3a) | General formula (3b) | General formula (3b) | General formula (3a) | H | H | tert-C$_4$H$_9$ | H | H | tert-C$_4$H$_9$ | H |
| 2-75 | CN | General formula (3a) | General formula (3b) | General formula (3b) | General formula (3a) | H | H | Phenyl | H | H | Phenyl | H |
| 2-76 | General formula (3a) | CN | General formula (3a) | General formula (3b) | General formula (3b) | H | H | H | H | H | H | H |
| 2-77 | General formula (3a) | CN | General formula (3a) | General formula (3b) | General formula (3b) | H | H | H | H | H | H | H |
| 2-78 | General formula (3a) | CN | General formula (3a) | General formula (3b) | General formula (3b) | H | H | H | H | H | H | H |
| 2-79 | General formula (3a) | CN | General formula (3a) | General formula (3b) | General formula (3b) | H | H | CH$_3$ | H | H | CH$_3$ | H |
| 2-80 | General formula (3a) | CN | General formula (3b) | General formula (3a) | General formula (3b) | H | H | H | H | H | H | H |
| 2-81 | General formula (3a) | CN | General formula (3b) | General formula (3a) | General formula (3b) | H | H | H | H | H | H | H |
| 2-82 | General formula (3a) | CN | General formula (3b) | General formula (3a) | General formula (3b) | H | H | H | H | H | H | H |
| 2-83 | General formula (3a) | CN | General formula (3b) | General formula (3a) | General formula (3b) | H | H | CH$_3$ | H | H | CH$_3$ | H |
| 2-84 | General formula (3a) | CN | General formula (3b) | General formula (3a) | General formula (3b) | H | H | CH$_3$ | H | H | CH$_3$ | H |
| 2-85 | General formula (3a) | CN | General formula (3b) | General formula (3a) | General formula (3b) | H | H | CH$_3$ | H | H | CH$_3$ | H |
| 2-86 | General formula (3a) | CN | General formula (3b) | General formula (3a) | General formula (3b) | H | H | tert-C$_4$H$_9$ | H | H | tert-C$_4$H$_9$ | H |
| 2-87 | General formula (3a) | CN | General formula (3b) | General formula (3a) | General formula (3b) | H | H | tert-C$_4$H$_9$ | H | H | tert-C$_4$H$_9$ | H |
| 2-88 | General formula (3a) | CN | General formula (3b) | General formula (3a) | General formula (3b) | H | H | Phenyl | H | H | Phenyl | H |
| 2-89 | General formula (3a) | CN | General formula (3b) | General formula (3a) | General formula (3b) | H | H | Phenyl | H | H | Phenyl | H |
| 2-90 | General formula (3a) | CN | General formula (3b) | General formula (3b) | General formula (3a) | H | H | H | H | H | H | H |
| 2-91 | General formula (3a) | CN | General formula (3b) | General formula (3b) | General formula (3a) | H | H | H | H | H | H | H |
| 2-92 | General formula (3a) | CN | General formula (3b) | General formula (3b) | General formula (3a) | H | H | H | H | H | H | H |
| 2-93 | General formula (3a) | CN | General formula (3b) | General formula (3b) | General formula (3a) | H | H | CH$_3$ | H | H | CH$_3$ | H |
| 2-94 | General formula (3a) | General formula (3a) | CN | General formula (3b) | General formula (3b) | H | H | H | H | H | H | H |
| 2-95 | General formula (3a) | General formula (3a) | CN | General formula (3b) | General formula (3b) | H | H | H | H | H | H | H |
| 2-96 | General formula (3a) | General formula (3a) | CN | General formula (3b) | General formula (3b) | H | H | H | H | H | H | H |
| 2-97 | General formula (3a) | General formula (3a) | CN | General formula (3b) | General formula (3b) | H | H | CH$_3$ | H | H | CH$_3$ | H |
| 2-98 | General formula (3a) | General formula (3b) | CN | General formula (3a) | General formula (3b) | H | H | H | H | H | H | H |
| 2-99 | General formula (3a) | General formula (3b) | CN | General formula (3a) | General formula (3b) | H | H | H | H | H | H | H |
| 2-100 | General formula (3a) | General formula (3b) | CN | General formula (3a) | General formula (3b) | H | H | H | H | H | H | H |
| 2-101 | General formula (3a) | General formula (3b) | CN | General formula (3a) | General formula (3b) | H | H | CH | H | H | CH$_3$ | H |
| 2-102 | General formula (3a) | General formula (3b) | CN | General formula (3a) | General formula (3b) | H | H | CH$_3$ | H | H | CH$_3$ | H |
| 2-103 | General formula (3a) | General formula (3b) | CN | General formula (3b) | General formula (3a) | H | H | H | H | H | H | H |
| 2-104 | General formula (3a) | General formula (3b) | CN | General formula (3b) | General formula (3a) | H | H | H | H | H | H | H |

TABLE 1-continued

| | | | | | | | | | | | | |
|---|---|---|---|---|---|---|---|---|---|---|---|---|
| 2-105 | General formula (3a) | General formula (3b) | CN | General formula (3b) | General formula (3a) | H | H | H | H | H | H | H |
| 2-106 | General formula (3a) | General formula (3b) | CN | General formula (3b) | General formula (3a) | H | H | $CH_3$ | H | H | $CH_3$ | H |
| 2-107 | General formula (3a) | General formula (3b) | General formula (3b) | General formula (3b) | General formula (3a) | H | H | H | H | H | H | H |
| 2-108 | General formula (3a) | General formula (3b) | General formula (3b) | General formula (3b) | General formula (3a) | H | H | $CH_3$ | H | H | $CH_3$ | H |
| 2-109 | General formula (3a) | General formula (3b) | General formula (3b) | General formula (3b) | General formula (3a) | H | H | tert-$C_4H_9$ | H | H | tert-$C_4H_9$ | H |
| 2-110 | General formula (3a) | General formula (3b) | General formula (3b) | General formula (3b) | General formula (3a) | H | H | Phenyl | H | H | Phenyl | H |
| 2-111 | General formula (3a) | General formula (3a) | Phenyl | General formula (3b) | General formula (3a) | H | H | Phenyl | H | H | Phenyl | H |
| 2-112 | General formula (3a) | General formula (3b) | H | General formula (3b) | General formula (3a) | H | H | H | H | H | H | H |
| 2-113 | General formula (3a) | General formula (3b) | m,m-DPP*2 | General formula (3b) | General formula (3a) | H | H | H | H | H | H | H |
| 2-114 | General formula (3a) | General formula (3b) | Phenyl | General formula (3a) | General formula (3a) | H | H | H | H | H | H | H |
| 2-115 | General formula (3a) | General formula (3b) | H | General formula (3b) | General formula (3b) | H | H | H | H | H | H | H |
| 2-116 | General formula (3a) | General formula (3b) | H | General formula (3b) | General formula (3b) | H | H | H | H | H | H | H |
| 2-117 | General formula (3a) | General formula (3b) | H | General formula (3b) | General formula (3b) | H | H | H | H | H | H | H |
| 2-118 | General formula (3a) | General formula (3b) | H | General formula (3b) | General formula (3b) | H | H | H | H | H | H | H |
| 2-119 | General formula (3a) | General formula (3b) | H | General formula (3b) | General formula (3b) | H | H | H | H | H | H | H |
| 2-120 | General formula (3a) | General formula (3b) | H | General formula (3b) | General formula (3b) | H | H | H | H | H | H | H |
| 2-121 | General formula (3a) | General formula (3b) | H | General formula (3b) | General formula (3b) | H | H | H | H | H | H | H |
| 2-122 | General formula (3a) | General formula (3b) | H | General formula (3b) | General formula (3b) | H | H | H | H | H | H | H |
| 2-123 | General formula (3a) | General formula (3b) | H | General formula (3b) | General formula (3b) | H | H | H | H | H | H | H |
| 2-124 | General formula (3a) | General formula (3b) | H | General formula (3b) | General formula (3b) | H | H | H | H | H | H | H |
| 2-125 | General formula (3a) | General formula (3b) | H | General formula (3b) | General formula (3b) | H | H | H | H | H | H | H |
| 2-126 | General formula (3a) | General formula (3b) | H | General formula (3b) | General formula (3b) | H | H | H | H | H | H | H |
| 2-127 | General formula (3a) | General formula (3b) | H | General formula (3b) | General formula (3b) | H | H | H | H | H | H | H |
| 2-128 | General formula (3a) | General formula (3b) | H | General formula (3b) | General formula (3b) | H | H | H | H | H | H | H |
| 2-129 | General formula (3a) | General formula (3b) | H | General formula (3b) | General formula (3b) | H | H | H | H | H | H | H |
| 2-130 | General formula (3a) | General formula (3b) | H | General formula (3b) | General formula (3b) | H | H | H | H | H | H | H |

| Compound No. | General formula (3a) | | General formula (3b) | | | | | | | | |
|---|---|---|---|---|---|---|---|---|---|---|---|
| | $R^{a8}$ | $R^{a9}$ | $R^{b1}$ | $R^{b2}$ | $R^{b3}$ | $R^{b4}$ | $R^{b5}$ | $R^{b6}$ | $R^{b7}$ | $R^{b8}$ | $R^{b9}$ |
| 2-1 | H | *1 | H | H | $CH_3$ | H | H | $CH_3$ | H | H | *1 |
| 2-2 | H | *1 | H | H | tert-$C_4H_9$ | H | H | tert-$C_4H_9$ | H | H | *1 |
| 2-3 | H | *1 | H | H | Phenyl | H | H | Phenyl | H | H | *1 |
| 2-4 | H | *1 | H | H | $CH_3$ | H | H | $CH_3$ | H | H | *1 |
| 2-5 | H | *1 | H | H | tert-$C_4H_9$ | H | H | tert-$C_4H_9$ | H | H | *1 |
| 2-6 | H | *1 | H | H | Phenyl | H | H | Phenyl | H | H | *1 |
| 2-7 | H | *1 | H | H | 9-Carbazolyl | H | H | 9-Carbazolyl | H | H | *1 |
| 2-8 | H | *1 | H | H | iso-Butyl | H | H | iso-Butyl | H | H | *1 |
| 2-9 | H | *1 | H | H | 2-Ethylhexyl | H | H | 2-Ethylhexyl | H | H | *1 |
| 2-10 | H | *1 | H | H | Trimethylsilyl | H | H | Trimethylsilyl | H | H | *1 |
| 2-11 | H | *1 | H | H | $CH_3$ | H | H | H | H | H | *1 |
| 2-12 | H | *1 | H | H | Phenyl | H | H | H | H | H | *1 |
| 2-13 | H | *1 | H | H | $CH_3$ | H | H | tert-$C_4H_9$ | H | H | *1 |
| 2-14 | H | *1 | H | H | $CH_3$ | H | H | Phenyl | H | H | *1 |
| 2-15 | H | *1 | H | H | Diphenylamino | H | H | Diphenylamino | H | H | *1 |
| 2-16 | H | *1 | H | H | Diphenylamino | H | H | H | H | H | *1 |
| 2-17 | H | *1 | H | H | H | H | H | H | H | H | *1 |

TABLE 1-continued

| | | | | | | | | | | |
|---|---|---|---|---|---|---|---|---|---|---|
| 2-18 | H | *1 | H | H | tert-C$_4$H$_9$ | H | H | tert-C$_4$H$_9$ | H | H | *1 |
| 2-19 | H | *1 | H | H | Phenyl | H | H | Phenyl | H | H | *1 |
| 2-20 | H | *1 | H | H | CH$_3$ | H | H | CH$_3$ | H | H | *1 |
| 2-21 | H | *1 | H | H | CH$_3$ | H | H | CH$_3$ | H | H | *1 |
| 2-22 | H | *1 | H | H | Phenyl | H | H | H | H | H | *1 |
| 2-23 | H | *1 | H | H | H | H | H | H | H | H | *1 |
| 2-24 | H | *1 | CH$_3$ | H | H | H | H | H | H | CH$_3$ | *1 |
| 2-25 | H | *1 | H | CH$_3$ | H | H | H | H | CH$_3$ | H | *1 |
| 2-26 | H | *1 | tert-C$_4$H$_9$ | H | H | H | H | H | H | tert-C$_4$H$_9$ | *1 |
| 2-27 | H | *1 | H | tert-C$_4$H$_9$ | H | H | H | H | tert-C$_4$H$_9$ | H | *1 |
| 2-28 | H | *1 | Phenyl | H | H | H | H | H | H | Phenyl | *1 |
| 2-29 | H | *1 | H | Phenyl | H | H | H | H | Phenyl | H | *1 |
| 2-30 | H | *1 | H | H | H | CH$_3$ | CH$_3$ | H | H | H | *1 |
| 2-31 | H | *1 | H | H | H | Phenyl | Phenyl | H | H | H | *1 |
| 2-32 | H | *1 | CH$_3$ | H | CH$_3$ | H | H | CH$_3$ | H | CH$_3$ | *1 |
| 2-33 | H | *1 | H | CH$_3$ | CH$_3$ | H | H | CH$_3$ | CH$_3$ | H | *1 |
| 2-34 | H | *1 | CH$_3$ | H | H | CH$_3$ | CH$_3$ | H | H | CH$_3$ | *1 |
| 2-35 | H | *1 | H | H | Phenyl | H | H | H | H | H | *1 |
| 2-36 | H | *1 | H | H | CH$_3$ | H | H | CH$_3$ | H | H | *1 |
| 2-37 | H | *1 | H | H | tert-C$_4$H$_9$ | H | H | tert-C$_4$H$_9$ | H | H | *1 |
| 2-38 | H | *1 | H | H | Phenyl | H | H | Phenyl | H | H | *1 |
| 2-39 | H | *1 | H | H | 2-Phenyl-phenyl | H | H | 2-Phenyl-phenyl | H | H | *1 |
| 2-40 | H | *1 | H | H | 3-Phenyl-phenyl | H | H | 3-Phenyl-phenyl | H | H | *1 |
| 2-41 | H | *1 | H | H | 4-Phenyl-phenyl | H | H | 4-Phenyl-phenyl | H | H | *1 |
| 2-42 | H | *1 | H | H | 2-Phenyl-phenyl | H | H | Phenyl | H | H | *1 |
| 2-43 | H | *1 | H | H | 3-Phenyl-phenyl | H | H | Phenyl | H | H | *1 |
| 2-44 | H | *1 | H | H | 4-Phenyl-phenyl | H | H | Phenyl | H | H | *1 |
| 2-45 | H | *1 | H | H | H | H | H | H | H | H | *1 |
| 2-47 | H | *1 | H | H | Phenyl | H | H | Phenyl | H | H | *1 |
| 2-48 | H | *1 | H | H | H | H | H | H | H | H | *1 |
| 2-49 | H | *1 | H | H | CH$_3$ | H | H | CH$_3$ | H | H | *1 |
| 2-50 | H | *1 | H | H | 2-Phenyl-phenyl | H | H | Phenyl | H | H | *1 |
| 2-51 | H | *1 | H | H | 3-Phenyl-phenyl | H | H | Phenyl | H | H | *1 |
| 2-52 | H | *1 | H | H | 4-Phenyl-phenyl | H | H | Phenyl | H | H | *1 |
| 2-53 | H | *1 | H | H | CH$_3$ | H | H | CH$_3$ | H | H | *1 |
| 2-54 | H | *1 | H | H | tert-C$_4$H$_9$ | H | H | tert-C$_4$H$_9$ | H | H | *1 |
| 2-55 | H | *1 | H | H | Phenyl | H | H | Phenyl | H | H | *1 |
| 2-56 | H | *1 | H | H | 2-Phenyl-phenyl | H | H | Phenyl | H | H | *1 |
| 2-57 | H | *1 | H | H | 3-Phenyl-phenyl | H | H | Phenyl | H | H | *1 |
| 2-58 | H | *1 | H | H | 4-Phenyl-phenyl | H | H | Phenyl | H | H | *1 |
| 2-59 | H | *1 | H | H | CH$_3$ | H | H | CH$_3$ | H | H | *1 |
| 2-60 | H | *1 | H | H | tert-C$_4$H$_9$ | H | H | tert-C$_4$H$_9$ | H | H | *1 |
| 2-61 | H | *1 | H | H | Phenyl | H | H | Phenyl | H | H | *1 |
| 2-62 | H | *1 | H | H | Phenyl | H | H | Phenyl | H | H | *1 |
| 2-63 | H | *1 | H | H | CH$_3$ | H | H | CH$_3$ | H | H | *1 |
| 2-64 | H | *1 | H | H | tert-C$_4$H$_9$ | H | H | tert-C$_4$H$_9$ | H | H | *1 |
| 2-65 | H | *1 | H | H | Phenyl | H | H | Phenyl | H | H | *1 |
| 2-66 | H | *1 | H | H | Phenyl | H | H | Phenyl | H | H | *1 |
| 2-67 | H | *1 | H | H | CH$_3$ | H | H | CH$_3$ | H | H | *1 |
| 2-68 | H | *1 | H | H | tert-C$_4$H$_9$ | H | H | tert-C$_4$H$_9$ | H | H | *1 |
| 2-69 | H | *1 | H | H | Phenyl | H | H | Phenyl | H | H | *1 |
| 2-70 | H | *1 | H | H | H | H | H | H | H | H | *1 |
| 2-71 | H | *1 | H | H | tert-C$_4$H$_9$ | H | H | tert-C$_4$H$_9$ | H | H | *1 |
| 2-72 | H | *1 | H | H | Phenyl | H | H | Phenyl | H | H | *1 |
| 2-73 | H | *1 | H | H | H | H | H | H | H | H | *1 |
| 2-74 | H | *1 | H | H | CH$_3$ | H | H | CH$_3$ | H | H | *1 |
| 2-75 | H | *1 | H | H | H | H | H | H | H | H | *1 |
| 2-76 | H | *1 | H | H | CH$_3$ | H | H | CH$_3$ | H | H | *1 |
| 2-77 | H | *1 | H | H | tert-C$_4$H$_9$ | H | H | tert-C$_4$H$_9$ | H | H | *1 |
| 2-78 | H | *1 | H | H | Phenyl | H | H | Phenyl | H | H | *1 |
| 2-79 | H | *1 | H | H | Phenyl | H | H | Phenyl | H | H | *1 |
| 2-80 | H | *1 | H | H | CH$_3$ | H | H | CH$_3$ | H | H | *1 |
| 2-81 | H | *1 | H | H | tert-C$_4$H$_9$ | H | H | tert-C$_4$H$_9$ | H | H | *1 |
| 2-82 | H | *1 | H | H | Phenyl | H | H | Phenyl | H | H | *1 |
| 2-83 | H | *1 | H | H | H | H | H | H | H | H | *1 |
| 2-84 | H | *1 | H | H | tert-C$_4$H$_9$ | H | H | tert-C$_4$H$_9$ | H | H | *1 |

TABLE 1-continued

| | | | | | | | | | | |
|---|---|---|---|---|---|---|---|---|---|---|
| 2-85 | H | *1 | H | H | Phenyl | H | H | Phenyl | H | H | *1 |
| 2-86 | H | *1 | H | H | H | H | H | H | H | H | *1 |
| 2-87 | H | *1 | H | H | CH$_3$ | H | H | CH$_3$ | H | H | *1 |
| 2-88 | H | *1 | H | H | H | H | H | H | H | H | *1 |
| 2-89 | H | *1 | H | H | CH$_3$ | H | H | CH$_3$ | H | H | *1 |
| 2-90 | H | *1 | H | H | CH$_3$ | H | H | CH$_3$ | H | H | *1 |
| 2-91 | H | *1 | H | H | tert-C$_4$H$_9$ | H | H | tert-C$_4$H$_9$ | H | H | *1 |
| 2-92 | H | *1 | H | H | Phenyl | H | H | Phenyl | H | H | *1 |
| 2-93 | H | *1 | H | H | Phenyl | H | H | Phenyl | H | H | *1 |
| 2-94 | H | *1 | H | H | CH$_3$ | H | H | CH$_3$ | H | H | *1 |
| 2-95 | H | *1 | H | H | tert-C$_4$H$_9$ | H | H | tert-C$_4$H$_9$ | H | H | *1 |
| 2-96 | H | *1 | H | H | Phenyl | H | H | Phenyl | H | H | *1 |
| 2-97 | H | *1 | H | H | Phenyl | H | H | Phenyl | H | H | *1 |
| 2-98 | H | *1 | H | H | CH$_3$ | H | H | CH$_3$ | H | H | *1 |
| 2-99 | H | *1 | H | H | tert-C$_4$H$_9$ | H | H | tert-C$_4$H$_9$ | H | H | *1 |
| 2-100 | H | *1 | H | H | Phenyl | H | H | Phenyl | H | H | *1 |
| 2-101 | H | *1 | H | H | tert-C$_4$H$_9$ | H | H | tert-C$_4$H$_9$ | H | H | *1 |
| 2-102 | H | *1 | H | H | Phenyl | H | H | Phenyl | H | H | *1 |
| 2-103 | H | *1 | H | H | CH$_3$ | H | H | CH$_3$ | H | H | *1 |
| 2-104 | H | *1 | H | H | tert-C$_4$H$_9$ | H | H | tert-C$_4$H$_9$ | H | H | *1 |
| 2-105 | H | *1 | H | H | Phenyl | H | H | Phenyl | H | H | *1 |
| 2-106 | H | *1 | H | H | Phenyl | H | H | Phenyl | H | H | *1 |
| 2-107 | H | *1 | H | H | CH$_3$ | H | H | CH$_3$ | H | H | *1 |
| 2-108 | H | *1 | H | H | H | H | H | H | H | H | *1 |
| 2-109 | H | *1 | H | H | H | H | H | H | H | H | *1 |
| 2-110 | H | *1 | H | H | H | H | H | H | H | H | *1 |
| 2-111 | H | *1 | H | H | H | H | H | H | H | H | *1 |
| 2-112 | H | *1 | H | H | CH$_3$ | H | H | H | H | H | *1 |
| 2-113 | H | *1 | H | H | Phenyl | H | H | Phenyl | H | H | *1 |
| 2-114 | H | *1 | H | H | Phenyl | H | H | Phenyl | H | H | *1 |
| 2-115 | H | *1 | H | H | CH$_3$ | H | H | CH$_3$ | H | H | *1 |
| 2-116 | H | *1 | H | H | tert-C$_4$H$_9$ | H | H | tert-C$_4$H$_9$ | H | H | *1 |
| 2-117 | H | *1 | H | H | Phenyl | H | H | Phenyl | H | H | *1 |
| 2-118 | H | *1 | H | H | CH$_3$ | H | H | CH$_3$ | H | H | *1 |
| 2-119 | H | *1 | H | H | tert-C$_4$H$_9$ | H | H | tert-C$_4$H$_9$ | H | H | *1 |
| 2-120 | H | *1 | H | H | Phenyl | H | H | Phenyl | H | H | *1 |
| 2-121 | H | *1 | H | H | 9-Carbazolyl | H | H | 9-Carbazolyl | H | H | *1 |
| 2-122 | H | *1 | H | H | iso-Butyl | H | H | iso-Butyl | H | H | *1 |
| 2-123 | H | *1 | H | H | 2-Ethyl-hexyl | H | H | 2-Ethyl-hexyl | H | H | *1 |
| 2-124 | H | *1 | H | H | Trimethyl-silyl | H | H | Trimethyl-silyl | H | H | *1 |
| 2-125 | H | *1 | H | H | CH$_3$ | H | H | H | H | H | *1 |
| 2-126 | H | *1 | H | H | Phenyl | H | H | H | H | H | *1 |
| 2-127 | H | *1 | H | H | CH$_3$ | H | H | tert-C$_4$H$_9$ | H | H | *1 |
| 2-128 | H | *1 | H | H | CH$_3$ | H | H | Phenyl | H | H | *1 |
| 2-129 | H | *1 | H | H | Diphenyl-amino | H | H | Diphenyl-amino | H | H | *1 |
| 2-130 | H | *1 | H | H | Diphenyl amino- | H | H | H | H | H | *1 |

*1: This shows a position bonding to the benzene ring in the general formula (1), The same applies to Table 2.
*2: This shows a m,m-diphenylphenyl group.

TABLE 2

| Compound No. | General formula (2) | | | | General formula (3a) | | | | | | | | | |
|---|---|---|---|---|---|---|---|---|---|---|---|---|---|---|
| | R$^{31}$ | R$^{32}$ | R$^{33}$ | R$^{34}$ | R$^{35}$ | R$^{a1}$ | R$^{a2}$ | R$^{a3}$ | R$^{a4}$ | R$^{a5}$ | R$^{a6}$ | R$^{a7}$ | R$^{a8}$ | R$^{a9}$ |
| 2-131 | General formula (3a) | D1 | CN | General formula (3a) | D1 | H | H | CH$_3$ | H | H | CH$_3$ | H | H | *1 |
| 2-132 | General formula (3a) | D2 | CN | General formula (3a) | D2 | H | H | CH$_3$ | H | H | CH$_3$ | H | H | *1 |
| 2-133 | General formula (3a) | D3 | CN | General formula (3a) | D3 | H | H | CH$_3$ | H | H | CH$_3$ | H | H | *1 |
| 2-134 | General formula (3a) | D4 | CN | General formula (3a) | D4 | H | H | CH$_3$ | H | H | CH$_3$ | H | H | *1 |
| 2-135 | General formula (3a) | D5 | CN | General formula (3a) | D5 | H | H | CH$_3$ | H | H | CH$_3$ | H | H | *1 |
| 2-136 | General formula (3a) | D6 | CN | General formula (3a) | D6 | H | H | CH$_3$ | H | H | CH$_3$ | H | H | *1 |
| 2-137 | General formula (3a) | D7 | CN | General formula (3a) | D7 | H | H | CH$_3$ | H | H | CH$_3$ | H | H | *1 |

TABLE 2-continued

| Compound No. | General formula (2) R$^{31}$ | R$^{32}$ | R$^{33}$ | R$^{34}$ | General formula (3a) R$^{35}$ | R$^{a1}$ | R$^{a2}$ | R$^{a3}$ | R$^{a4}$ | R$^{a5}$ | R$^{a6}$ | R$^{a7}$ | R$^{a8}$ | R$^{a9}$ |
|---|---|---|---|---|---|---|---|---|---|---|---|---|---|---|
| 2-138 | General formula (3a) | D8 | CN | General formula (3a) | D8 | H | H | CH$_3$ | H | H | CH$_3$ | H | H | *1 |

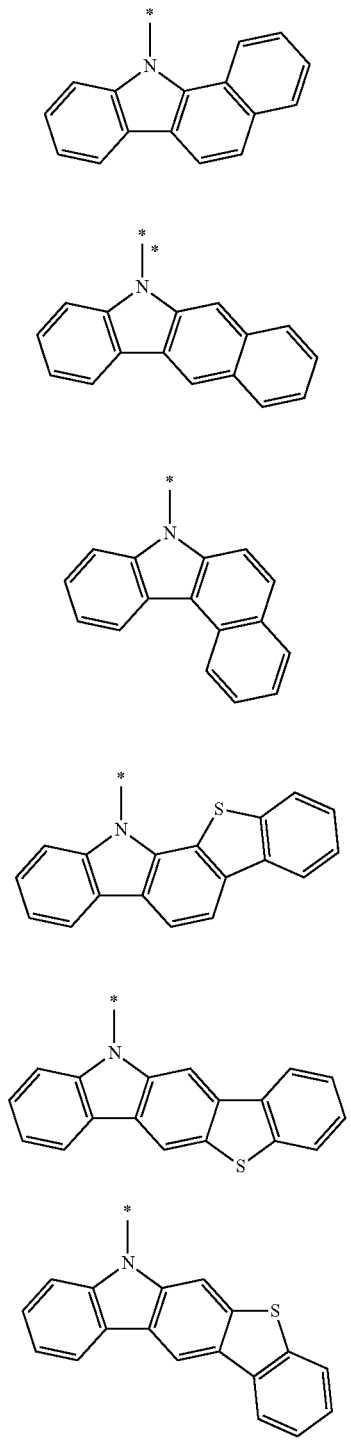

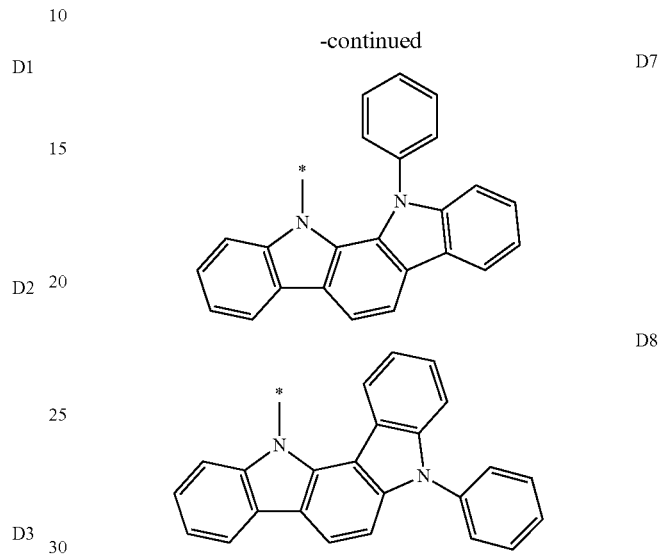

[Combination of Compound Represented by General Formula (1) and Compound Represented by General Formula (2)]

As combined, the compound represented by the general formula (1) and the compound represented by the general formula (2) can be used as materials for organic light-emitting devices. In an organic light-emitting device, energy transfer from the compound represented by the general formula (2) to the compound represented by the general formula (1) can efficiently undergo, and the energy is used for light emission. This mechanism is described below with reference to an example of an organic electroluminescent device containing a compound represented by the general formula (1) and a compound represented by the general formula (2).

In an organic electroluminescent device where excitation energy is generated by recombination of holes and electrons injected from the electrode, the organic compounds contained in an organic layer between electrodes transit from the ground state to an excited singlet state and an excited triplet state. The probability of formation of the organic compound in an excited singlet state (singlet exciton) and the organic compound in an excited triplet state (triplet exciton) is statistically such that the singlet exciton accounts for 25% and the triplet exciton accounts for 75%. With that, among the excitons, the energy of the compound of the general formula (2) in an excited singlet state transfers to the compound of the general formula (1), and the compound of the general formula (1) in the ground state transits to an excited singlet state. The compound of the general formula (1) thus having been in an excited singlet state emits fluorescence when thereafter returning back to the ground state. Or, energy of the compound of the general formula (1) having been in an excited singlet state transfers to a different light-emitting material, and the light-emitting material in a ground state transits to an excited singlet state, and when thereafter returning back to the ground state, the light-emitting material emits fluorescence.

At that time, in the organic electroluminescent device of the present invention, the compound of the general formula (2) is a compound that can readily undergo reverse intersystem crossing from an excited triplet state to an excited singlet state, and therefore the singlet excited energy by the reverse intersystem crossing also transfers to the compound of the general formula (1). Consequently, energy in an excited triplet state having a large abundance ratio can also indirectly contribute toward light emission, and as compared with that of a configuration not containing the compound of the general formula (2), the light emission efficiency of the organic electroluminescent device of the type can be exponentially enhanced.

The compound of the general formula (2) is preferably a compound that can readily undergo reverse intersystem crossing. Accordingly, the compound is preferably a thermal activation type delayed fluorescent material that undergoes reverse intersystem crossing from an excited triplet state to an excited singlet state through absorption of thermal energy. A thermal activation type delayed fluorescent material can relatively readily undergo reverse intersystem crossing from an excited triplet state to an excited singlet state by absorbing heat generated by a device, and the excited triplet energy can be made to efficiently contribute toward light emission. Preferably, the compound of the general formula (2) is such that the difference $\Delta E_{ST}$ between the energy level $E_{S1}$ in a lowest excited singlet state and the energy level $E_{T1}$ in a lowest excited triplet state at 77 K is 0.3 eV or less, more preferably 0.2 eV or less, even more preferably 0.15 eV or less, further more preferably 0.10 eV or less. A compound having a small energy difference $\Delta E_{ST}$ can relatively readily undergo reverse intersystem crossing from an excited triplet state to an excited singlet state, and therefore the excited triplet energy thereof can be made to efficiently contribute toward light emission. In addition, in the compound, accumulation of triplet excitons in the excitation process can be effectively suppressed, and therefore, using the compound represented by the general formula (2) is advantageous in that exciton annihilation owing to accumulation of triplet excitons and device degradation can be suppressed to secure excellent durability in addition to higher light emission efficiency. Further, since exciton annihilation can be suppressed, another advantage is that the compound of the type can greatly contribute toward realization of organic lasers.

Using a compound represented by the general formula (1) and a compound represented by the general formula (2) makes it possible to realize an organic light-emitting device that emits good blue light. For example, the combined use of the compounds makes it possible to realize an organic light-emitting device capable of emitting light such that, in the CIE-XYZ chromaticity coordinate system, the chromaticity coordinate x is 0.23 or less and y is 0.40 or less, preferably x is 0.20 or less and y is 0.30 or less, more preferably x is 0.16 or less and y is 0.26 or less. At present, few satisfactory organic light-emitting devices capable of emitting good blue light at a high emission efficiency are provided, and the usefulness of the present invention is extremely high. The emission color from the organic light-emitting device of the present invention is not always limited to blue, and even an organic light-emitting device capable of realizing light emission except blue light is also within the scope of the present invention so far as the device uses the compound represented by the general formula (1) and the compound represented by the general formula (2).

[Organic Light-Emitting Device]

The compound represented by the general formula (1) and the compound represented by the general formula (2) can be made to be contained in any layer together that constitute an organic light-emitting device, or may be made to be contained separately in different layers. In the case where the two compounds are contained separately in different layers, preferably, the compounds are contained in neighboring layers. For example, the compound represented by the general formula (1) and the compound represented by the general formula (2) can be made to be contained together in a light-emitting layer, or the compound represented by the general formula (1) and the compound represented by the general formula (2) can be made to be contained together in a layer neighboring to a light-emitting layer, or the compound represented by the general formula (1) can be made to be contained in a light-emitting layer and the compound represented by the general formula (2) can be made to be contained in a layer neighboring to the light-emitting layer.

Preferably, the organic light-emitting device uses a larger amount of the compound of the general formula (2) than the compound of the general formula (1). When the total of the compounds is referred to as 100 parts by weight, preferably, the amount of the compound of the general formula (1) to be used is 0.01 to 49.9 parts by weight, more preferably 1 to 35 parts by weight.

In the case where the compound of the general formula (1) and the compound of the general formula (2) are made to be contained together in a light-emitting layer, the layer may contain a host material in addition to these compounds. The host material is an organic compound having a larger lowest excited singlet energy than the compound of the general formula (1) and the compound of the general formula (2), and has a function as a host material for carrier transport or a function of trapping the energy of the compound of the general formula (1) inside the compound. With that, the organic compound of the general formula (1) can efficiently change the energy generated by recombination of holes and electrons in the molecule thereof and the energy received from the host material and the compound of the general formula (2) for light emission, therefore realizing an organic electroluminescent device having a high light emission efficiency.

The host material for use herein is preferably an organic compound having hole transport capability and electron transport capability, capable of preventing wavelength prolongation in light emission and having a high glass transition temperature. Also preferably, the amount of the host material to be contained in the light-emitting layer is larger than that of the compound of the general formula (1) and the compound of the general formula (2) therein. Specifically, the amount of the host material is preferably 40% by weight or more of the total weight of the light-emitting material, more preferably 50% by weight or more, and is preferably 99.9% by weight or less, more preferably 95% by weight or less. In the case where the light-emitting layer contains the compound of the general formula (1) and the compound of the general formula (2) alone, and in the case where the light-emitting layer contains the compound of the general formula (1), the compound of the general formula (2) and a host material, the compound of the general formula (1) mainly emits light via energy transfer from the compound of the general formula (2) to the compound of the general formula (1).

In the case where the compound of the general formula (1) and the compound of the general formula (2) are both contained in a light-emitting layer, the layer may contain a light-emitting material in addition to these compounds. The light-emitting material is a compound having a smaller lowest excited singlet energy than the compound of the general formula (1). In that case, the light-emitting layer may contain a host material. The light-emitting material receives energy transfer from the compound of the general formula (1) or the compound of the general formula (2) or from both the two to emit light. At that time, light emission from the compound of the general formula (1) may be observed. Preferably, the content of the light-emitting material in the light-emitting layer is 0.01% by weight to 30% by weight of the total weight of the light-emitting layer, more preferably 0.1% by weight to 15% by weight.

In the case where the compound of the general formula (1) and the compound of the general formula (2) are both contained in a layer neighboring to a light-emitting layer, the light-emitting layer contains a light-emitting material. The light-emitting layer may also contain the compound of the general formula (1). The light-emitting material in the light-emitting layer receives energy transfer from the compound of the general formula (1) or the compound of the general formula (2) in the neighboring layer, or from both the two for light emission.

Another configuration is also acceptable where the compound of the general formula (1) is contained in a light-emitting layer and the compound of the general formula (2) is contained in a layer neighboring to the light-emitting layer. Still another configuration is also acceptable where the compound of the general formula (1) having received energy transfer from the compound of the general formula (2) emits light, or the light-emitting layer further contains a light-emitting material to emit light.

The usage mode of the compound of the general formula (1) and the compound of the general formula (2) in an organic light-emitting device can be appropriately arranged depending on the production purpose and the function of the organic light-emitting device.

A configuration of an organic light-emitting device is described below.

An organic photoluminescent (PL) device has a structure where at least a light-emitting layer is formed on a substrate. An organic electroluminescent (EL) device has a structure including at least an anode, a cathode and an organic layer formed between the anode and the cathode. The organic layer contains at least a light-emitting layer, and may be formed of a light-emitting layer alone, or may has one or more other organic layers in addition to a light-emitting layer. The other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. In the case where the compound of the general formula (1) and the compound of the general formula (2) are contained in a layer neighboring to a light-emitting layer, these compounds may be contained in any of the above-mentioned layers neighboring to a light-emitting layer. A specific configuration example of an organic electroluminescent device is shown in FIG. 1. In FIG. 1, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the organic electroluminescent device are described. The description of the substrate and the light-emitting layer given below may be applied to the substrate and the light-emitting layer of an organic photoluminescent device.

(Substrate)

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

(Anode)

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ω/sq or less. The thickness of the anode may be generally selected from a range of from 10 to 1,000 nm, and preferably from 10 to 200 nm, while depending on the material used.

(Cathode)

The cathode is preferably formed of, as an electrode material, a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred Ω/sq or less, and the thickness thereof may be generally selected from a range of from 10 nm to 5 m, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer in which holes and electrons injected from an anode and a cathode are recombined to give excitons for light emission. The light-emitting layer may be a layer containing the compound of the general formula (1) and the compound of the general formula (2), a layer containing the compound of the general formula (1), the compound of the general formula (2) and a host material, a layer containing the compound of the general formula (1), the compound of the general formula (2) and a light-emitting material, a layer containing the compound of the general formula (1), the compound of the general formula (2), a light-emitting material and a host material, a layer containing a light-emitting material, a layer containing a light-emitting material and a host material, or a layer containing a light-emitting material and the compound of the general formula (1). In the case where the light-emitting layer does not contain the compound of the general formula (1), a layer neighboring to the light-emitting layer contains the compound of the general formula (1). In the case where the light-emitting layer does not contain the compound of the general formula (2), a layer neighboring to the light-emitting layer contains the compound of the general formula (2).

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be adjacent to the light-emitting layer and inserted on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. A porphyrin compound, an aromatic tertiary amine compound and a styrylamine compound are preferably used, and an aromatic tertiary amine compound is more preferably used.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function.

First, preferred compounds for use as a host material in a light-emitting layer are mentioned below.

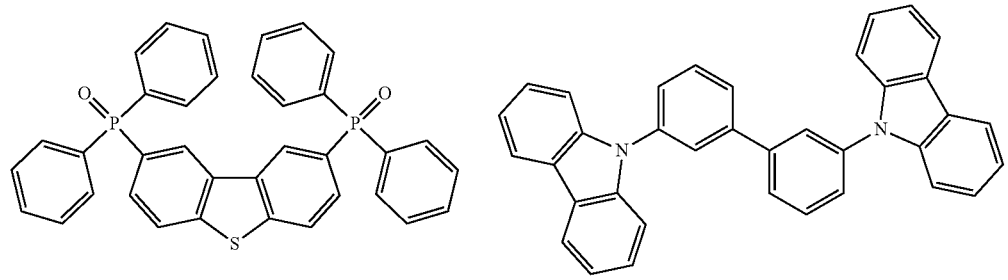

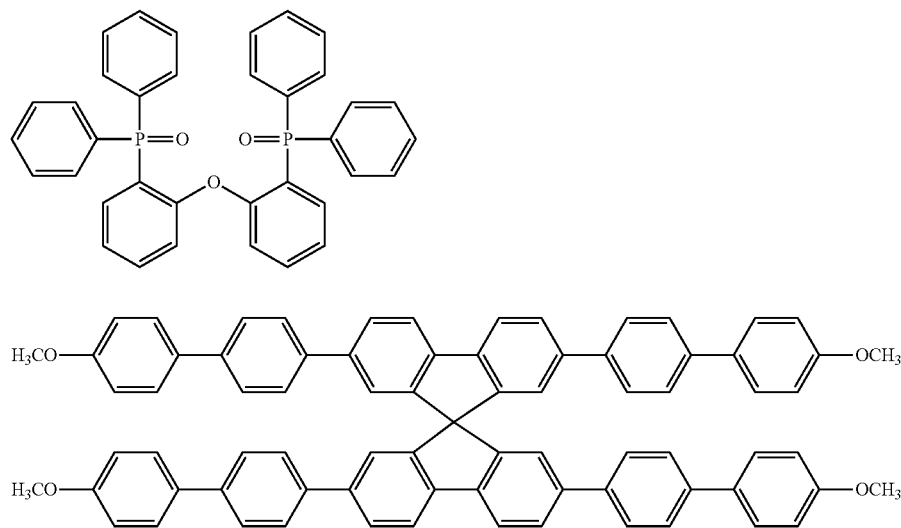

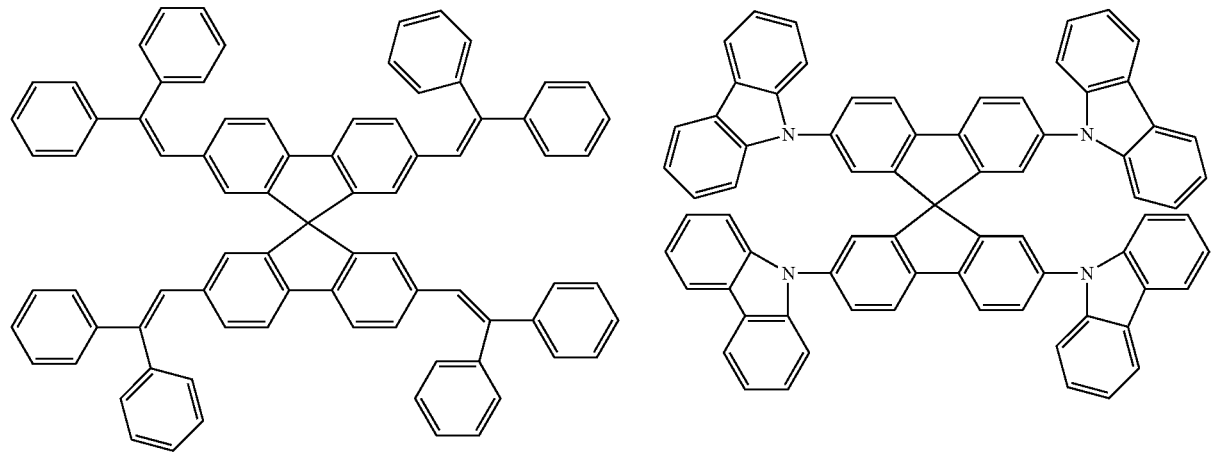

-continued
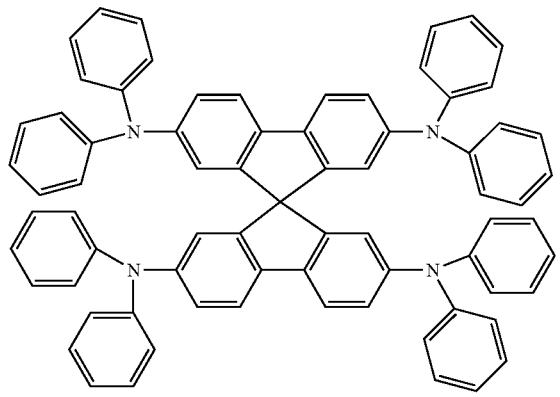
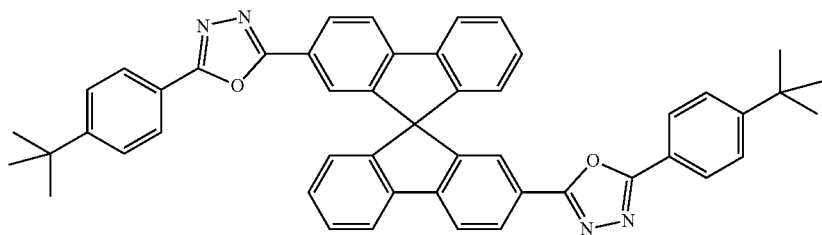
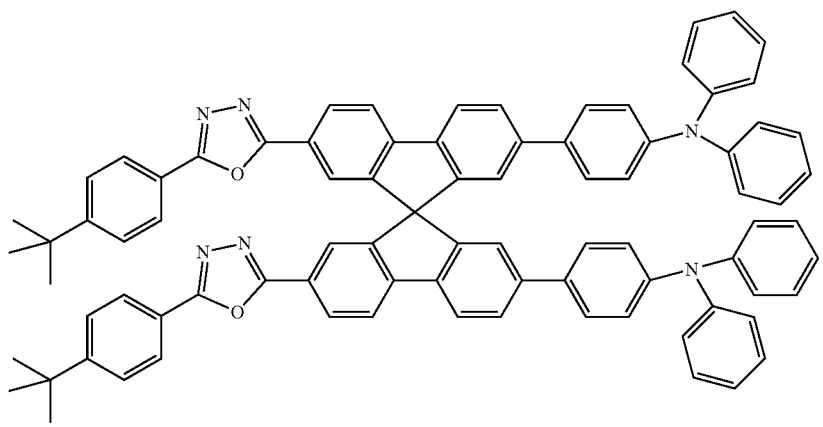
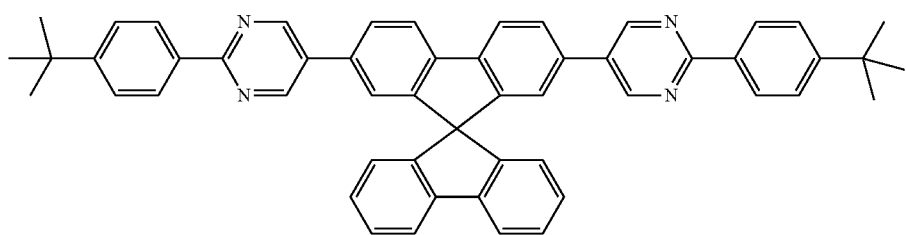
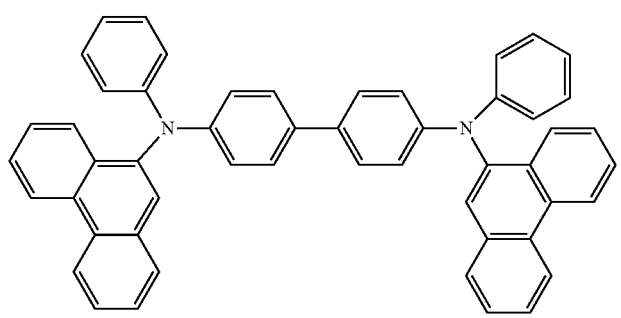
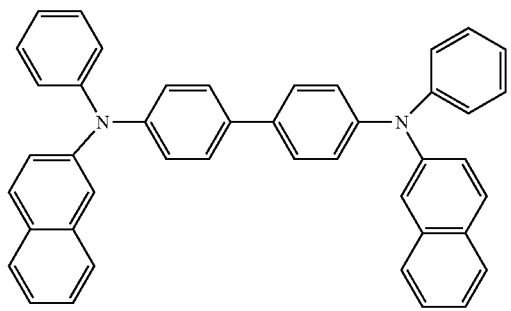

-continued
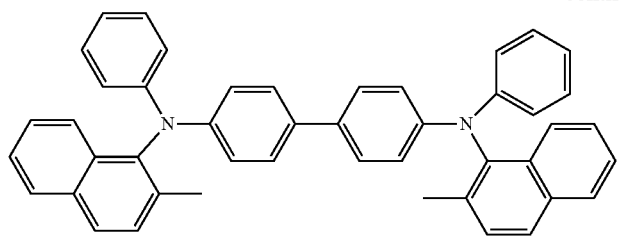
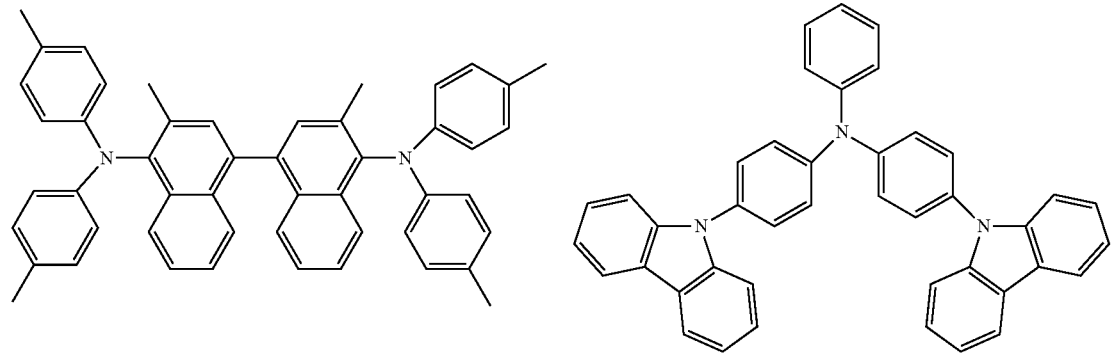
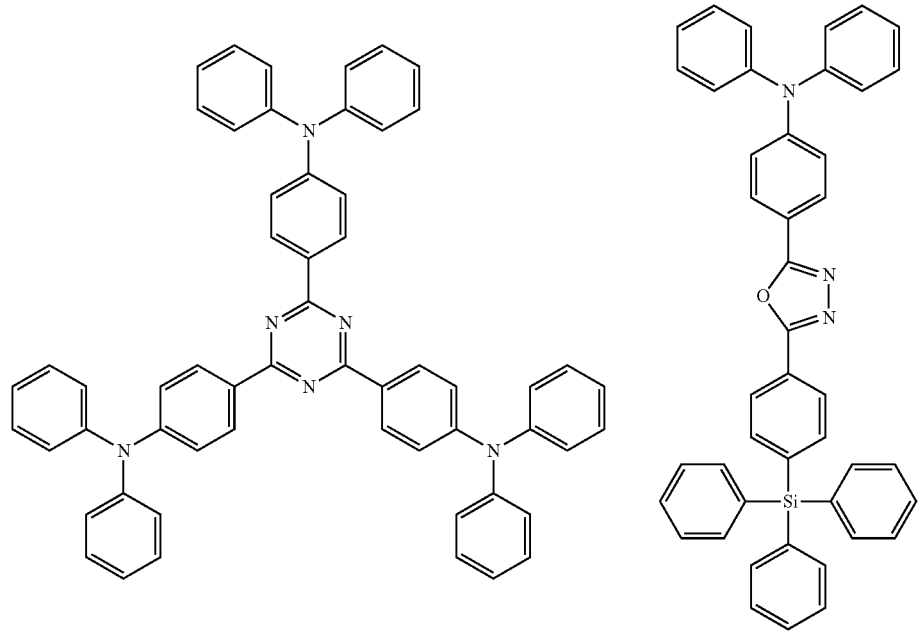
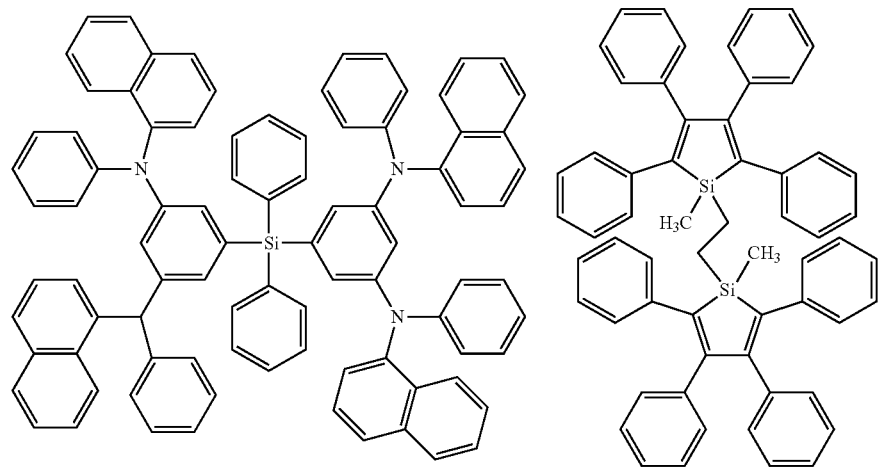

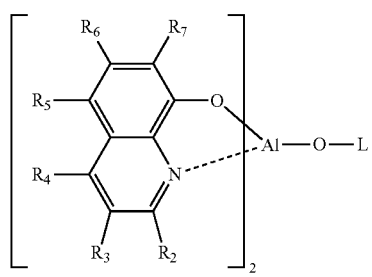
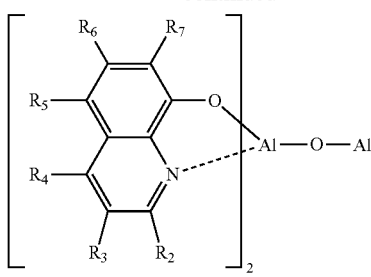
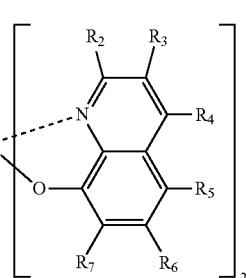
$R_2$–$R_7$ = H or substituent
L = ligand
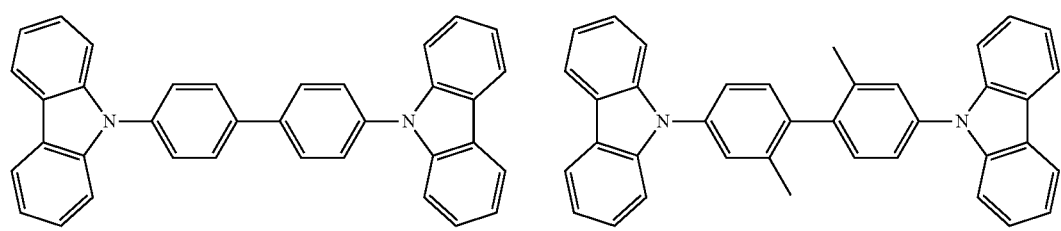
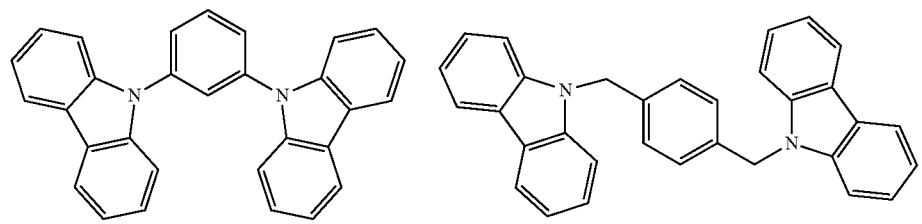
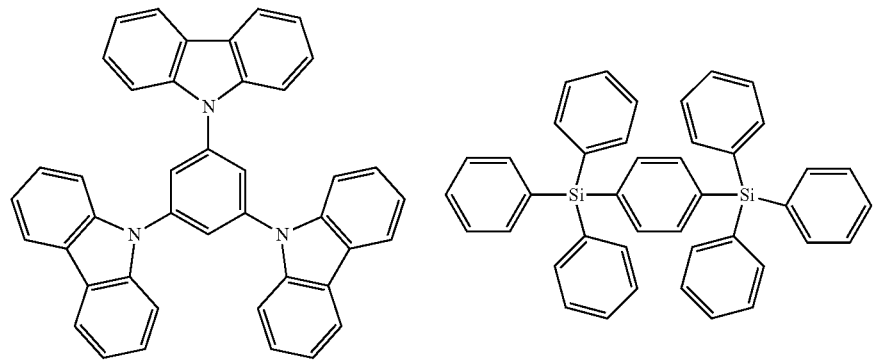
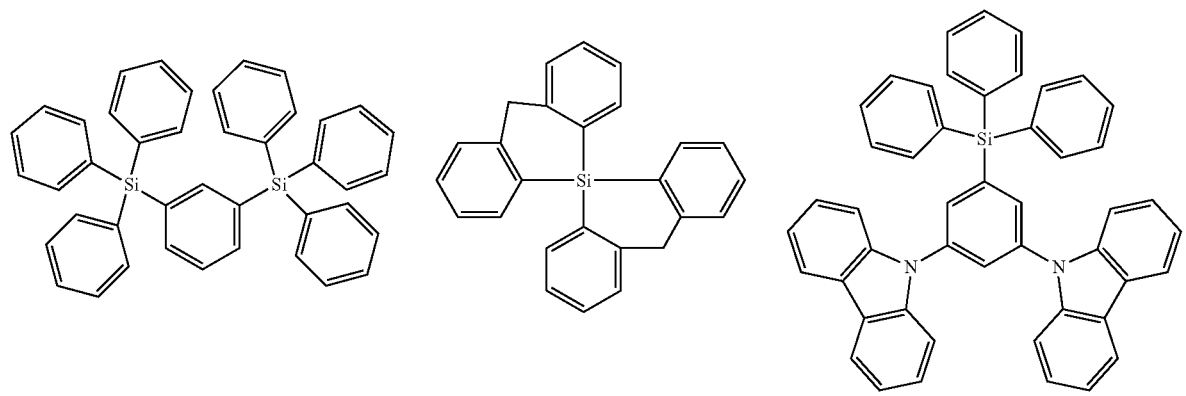

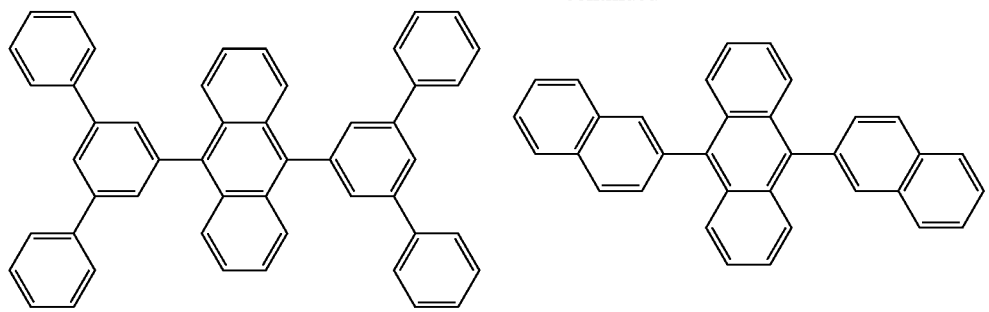
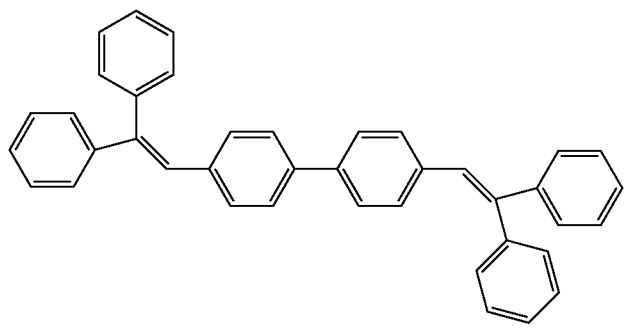
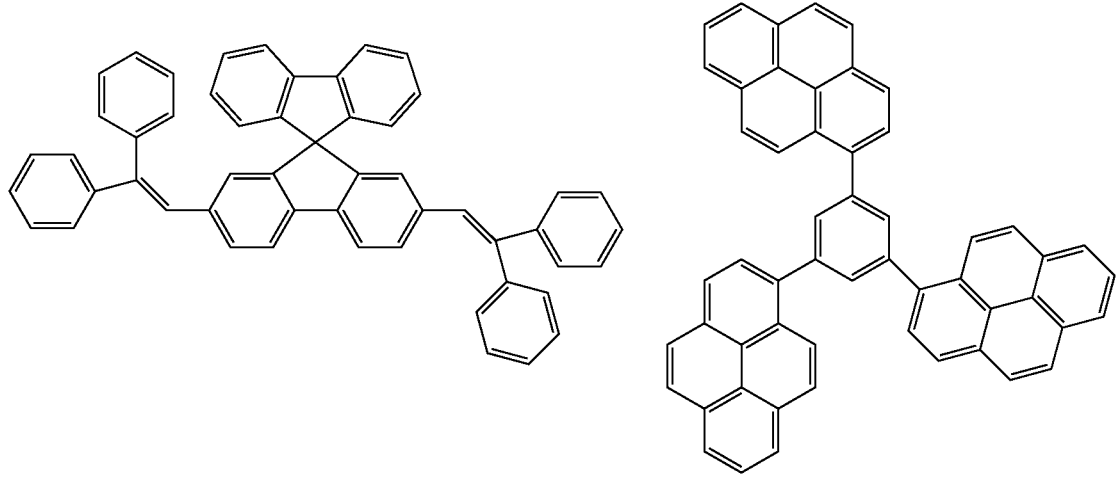

-continued
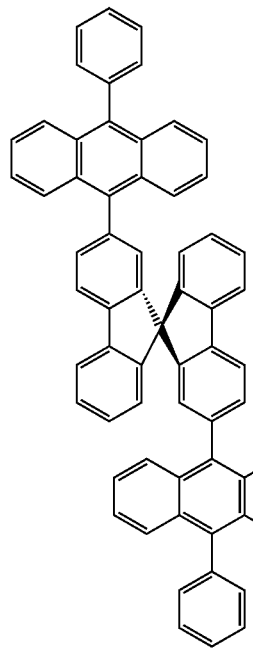
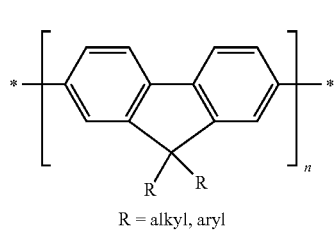
R = alkyl, aryl
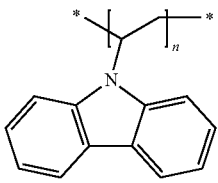
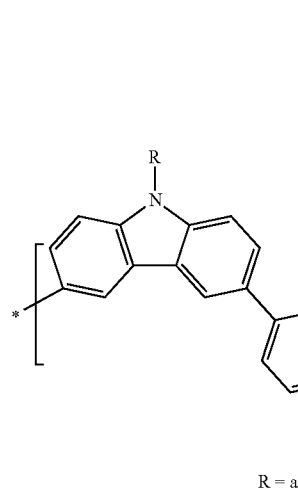
R = alkyl, aryl
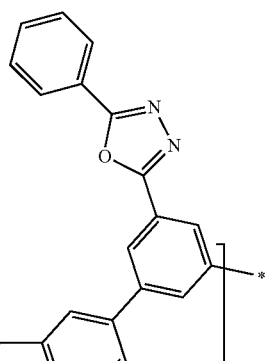
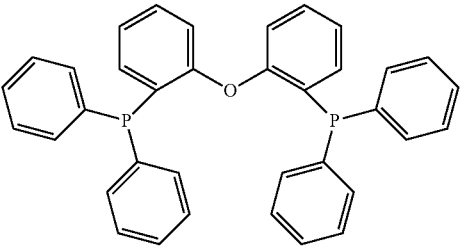
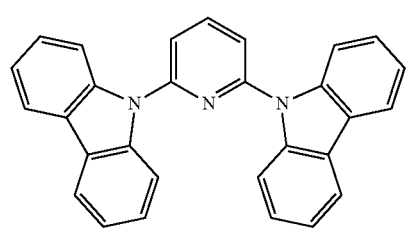
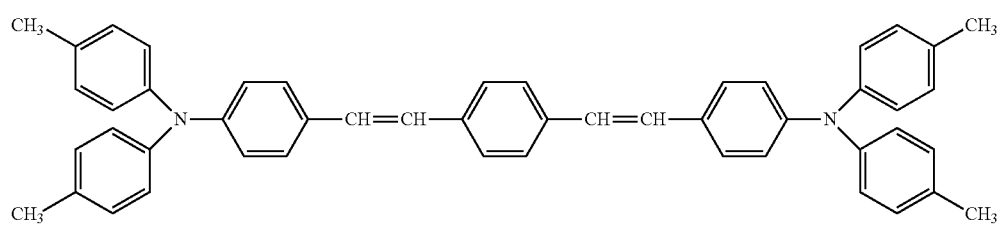

Next, examples of preferred compounds for use as a hole injection material are mentioned below.
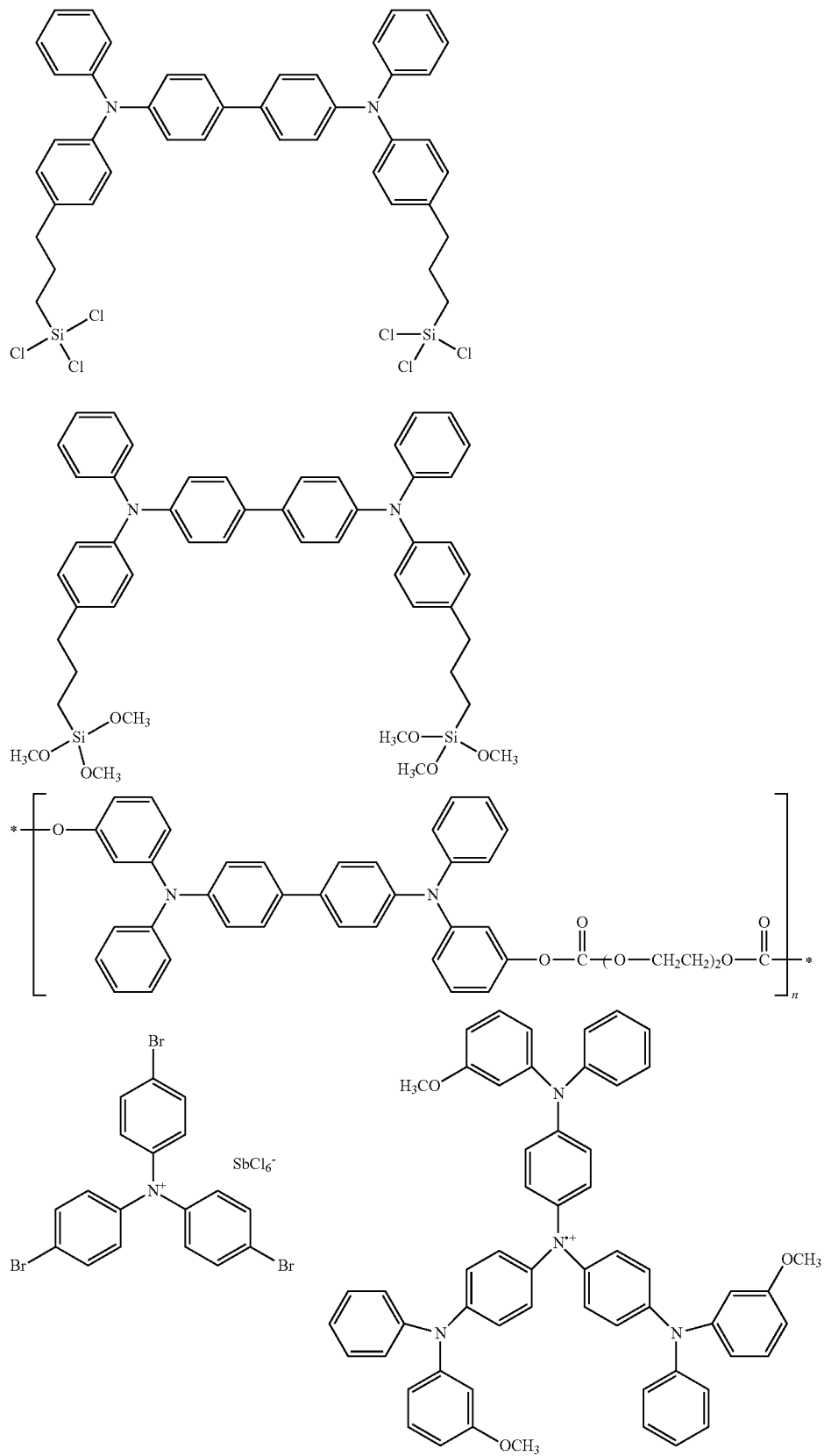

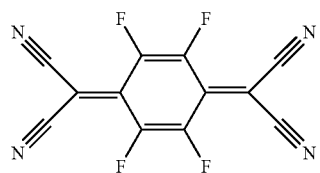
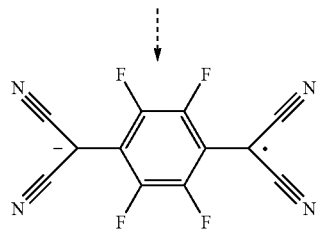
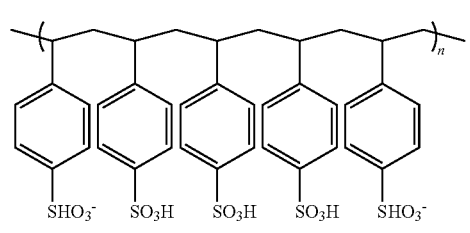 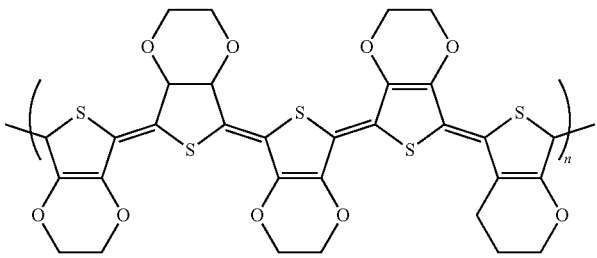
Next, examples of preferred compounds for use as a hole transport material are mentioned below.
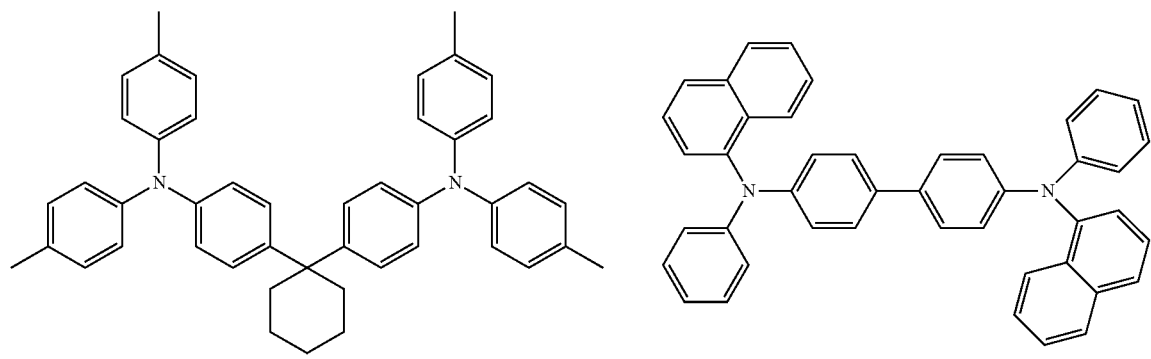
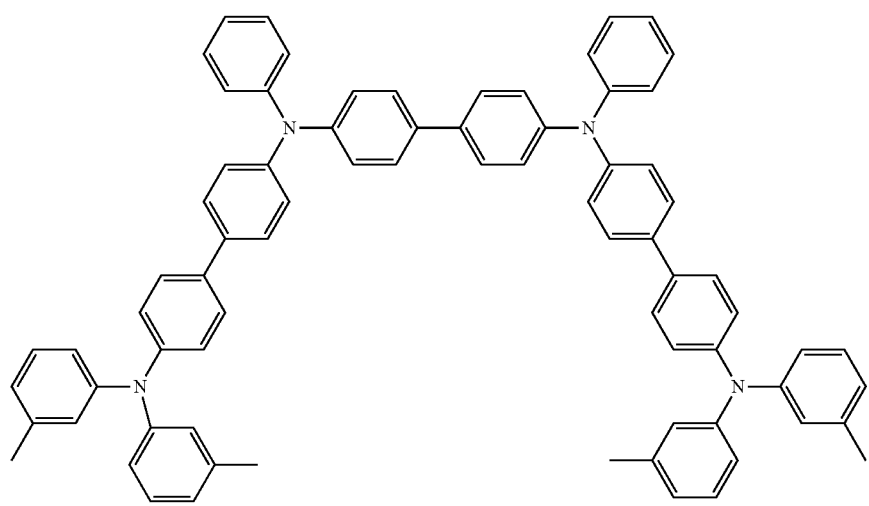

53 54
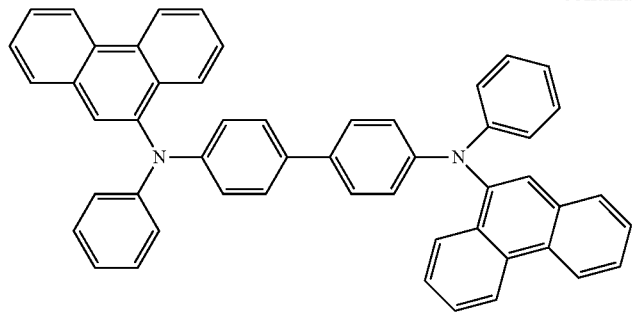 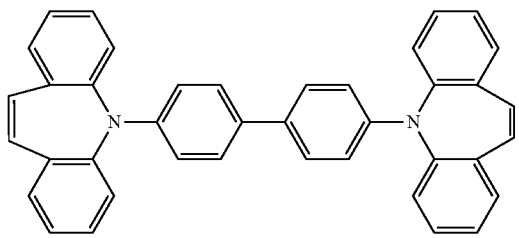
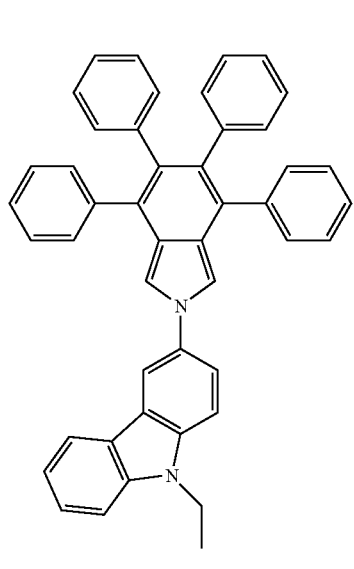 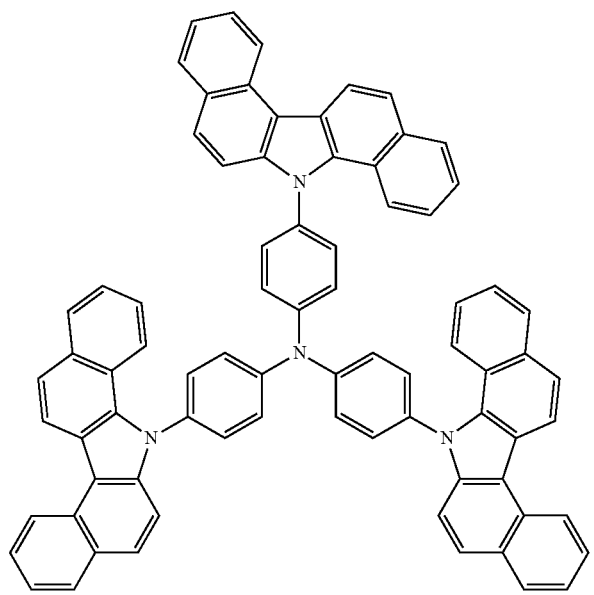
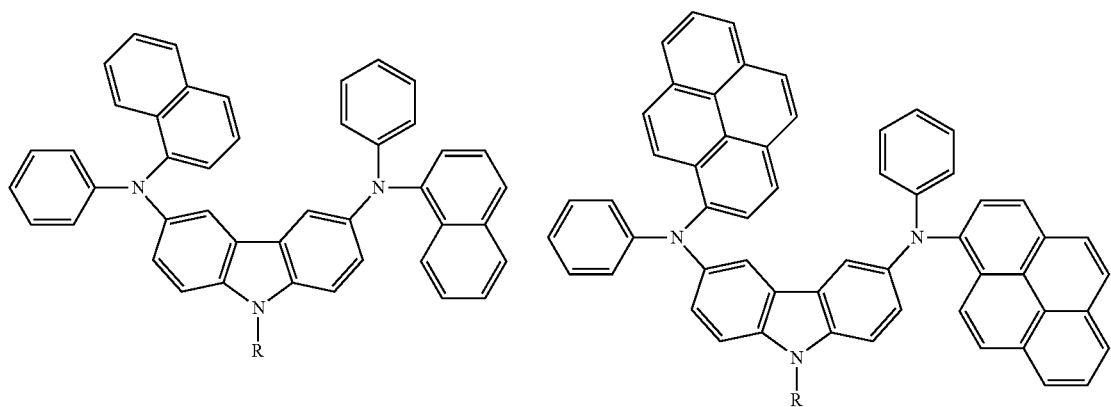

-continued
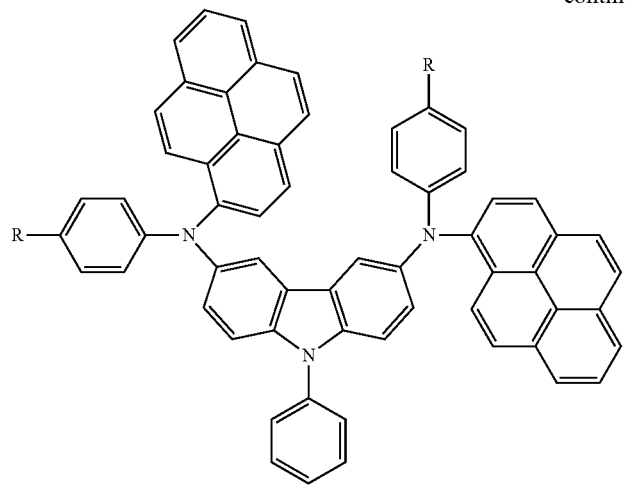
R = alkyl, aryl, alkoxy, aryloxy
9,9'-dialkylfluorene
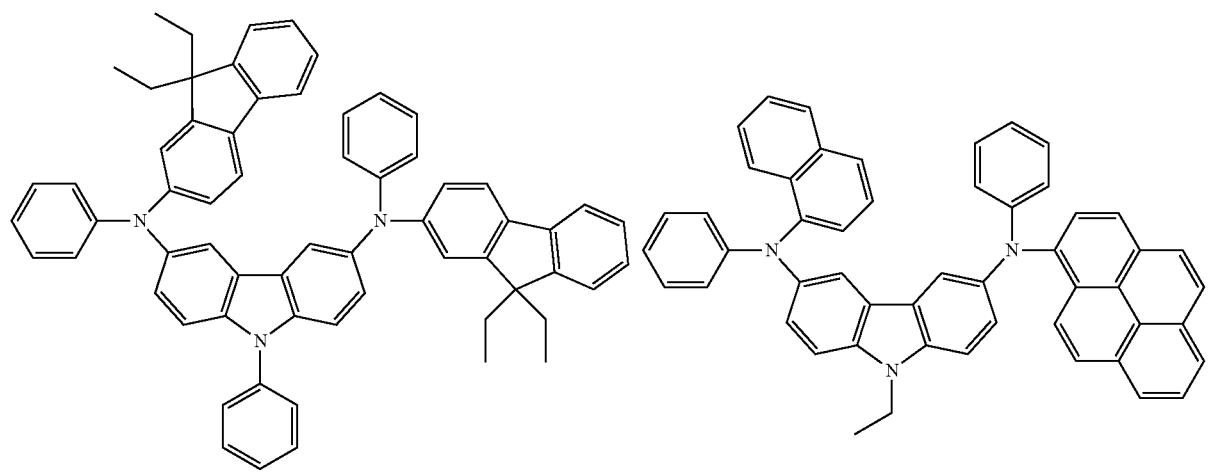
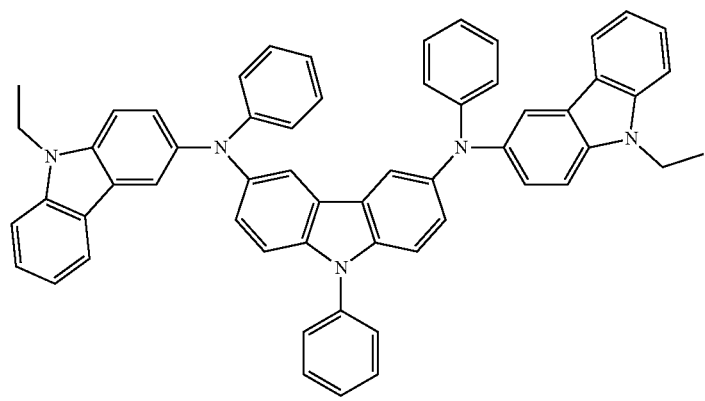

-continued
57
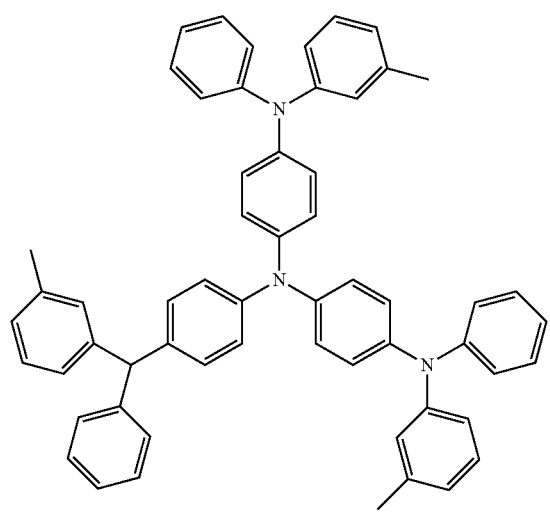
58
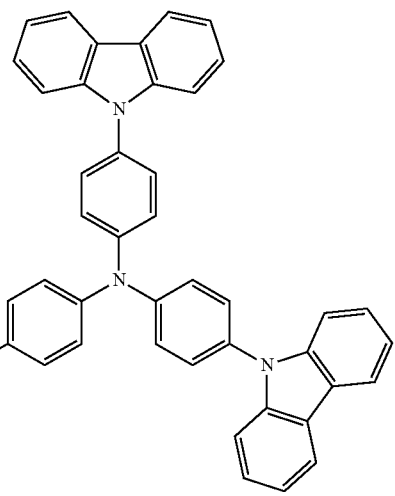
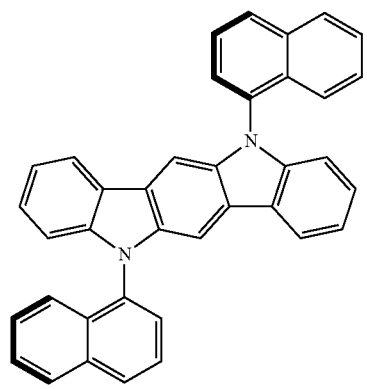
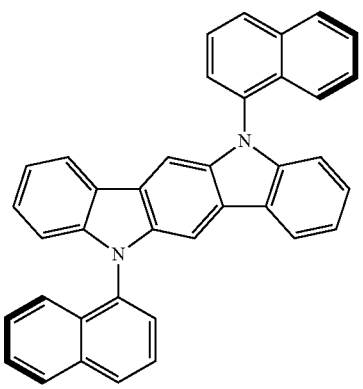
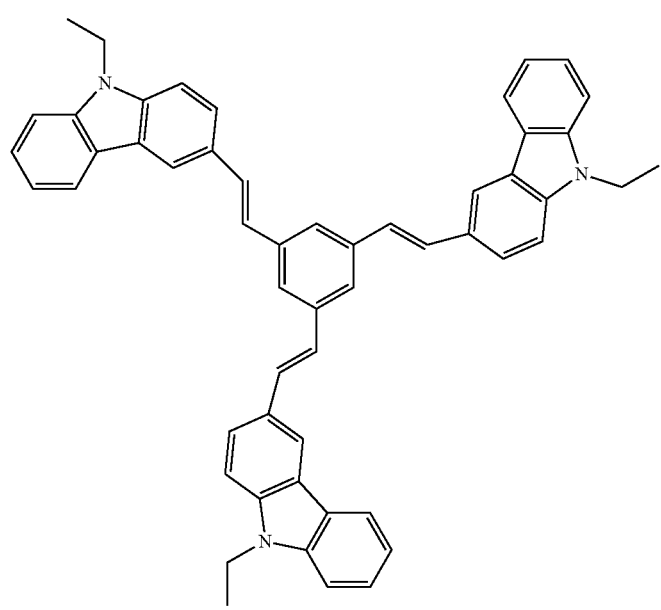

-continued
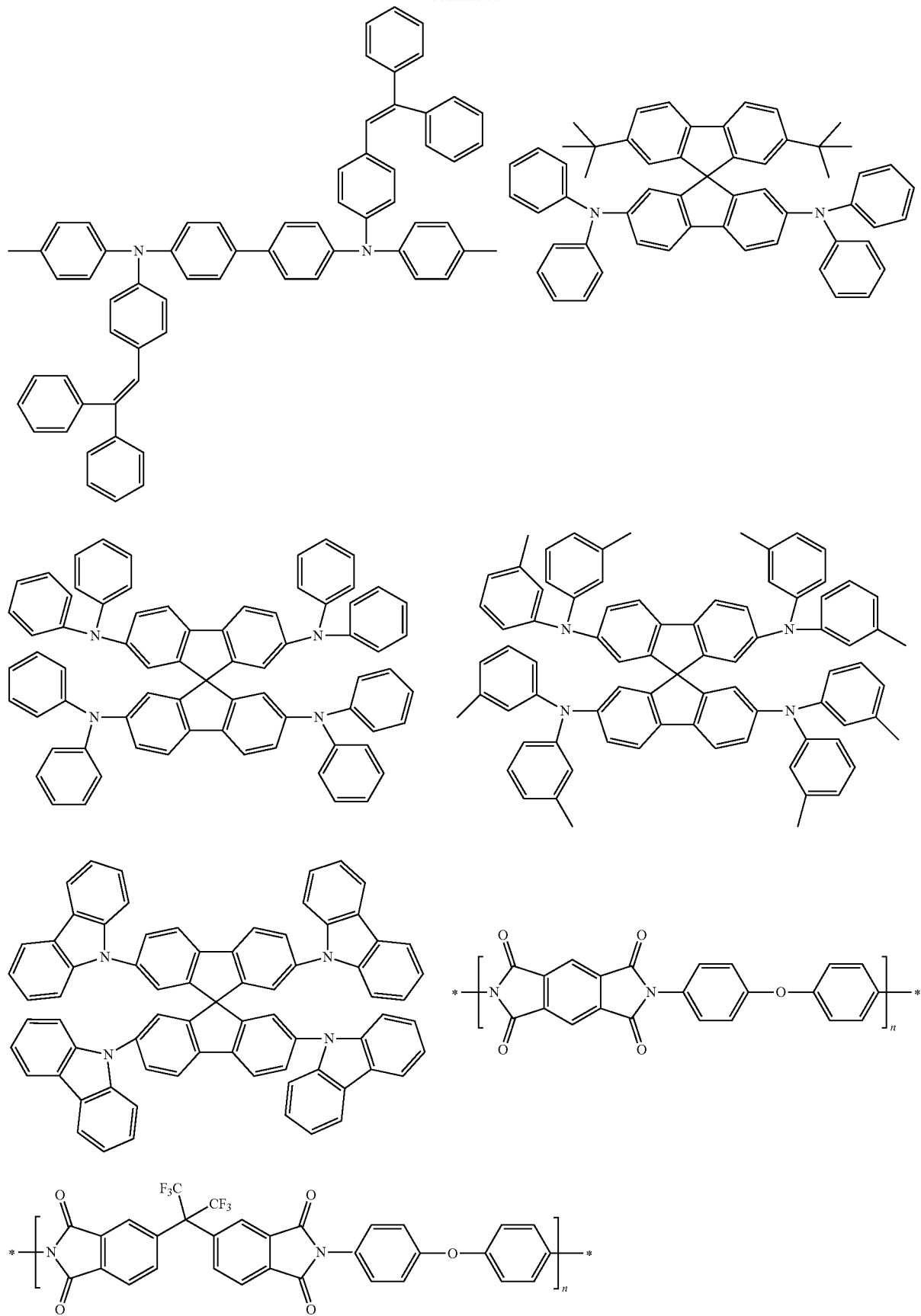

-continued
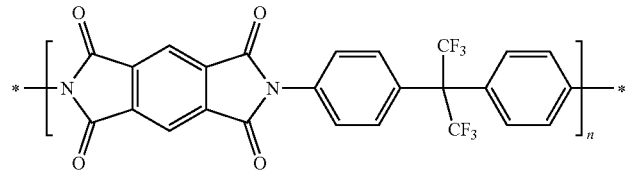
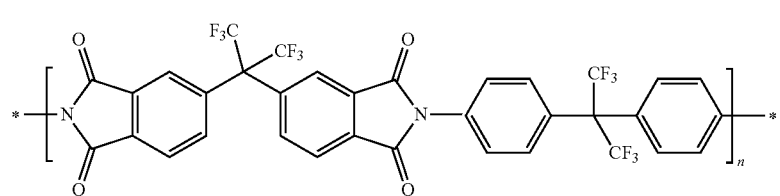
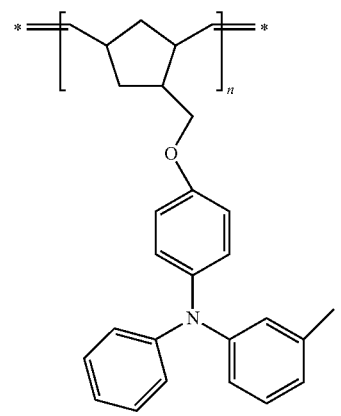
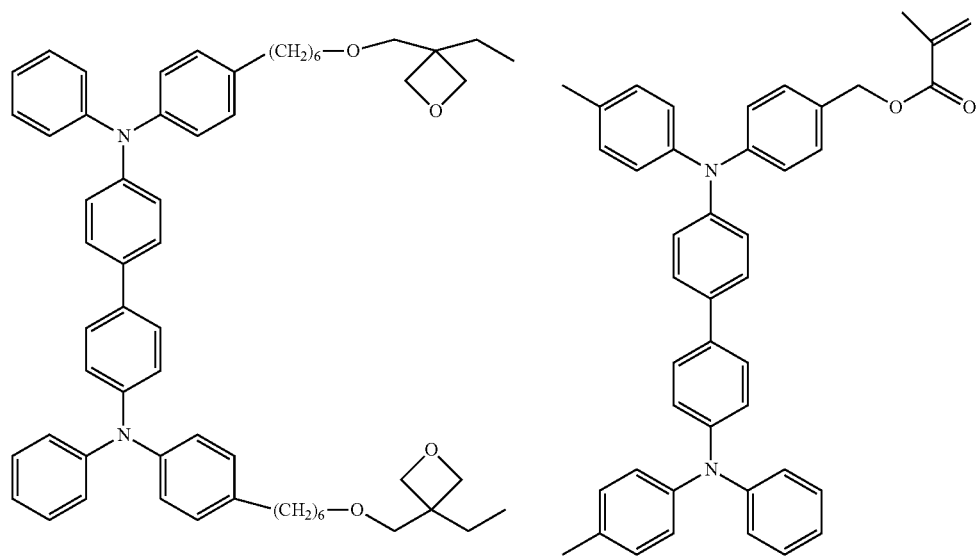

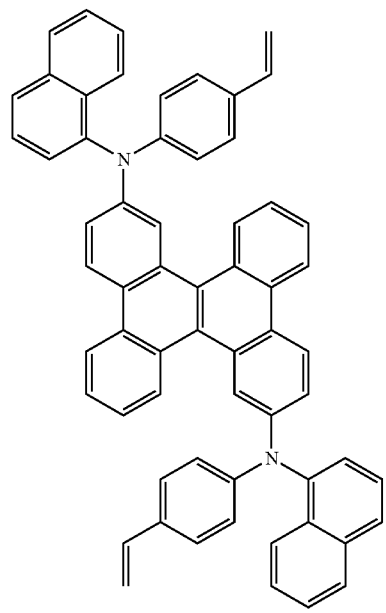
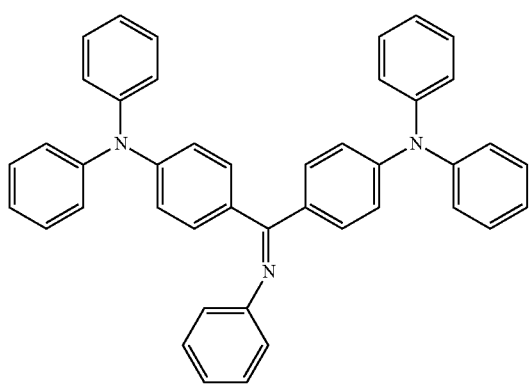
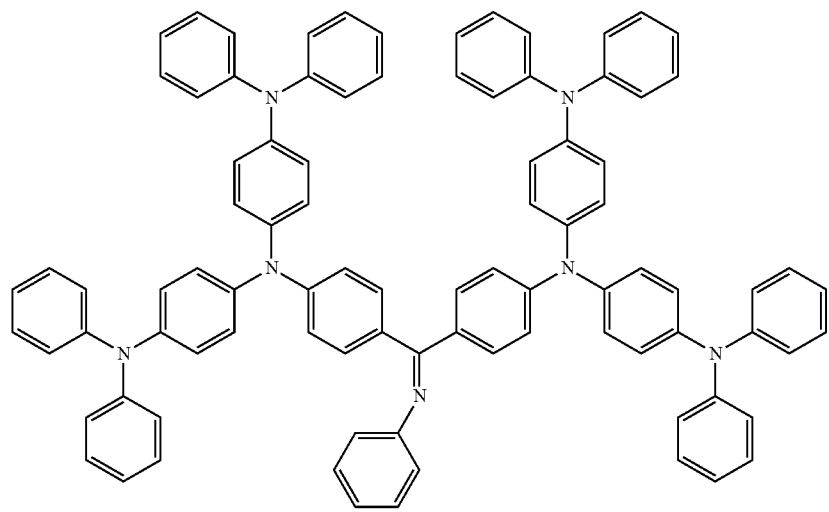

-continued
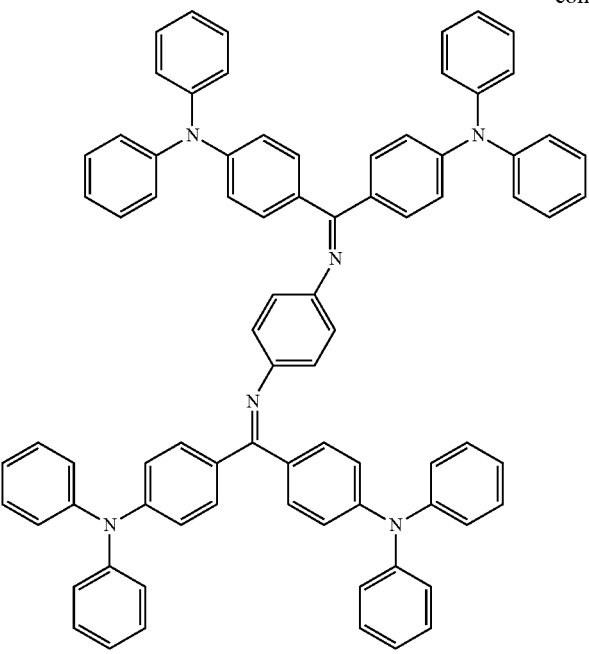
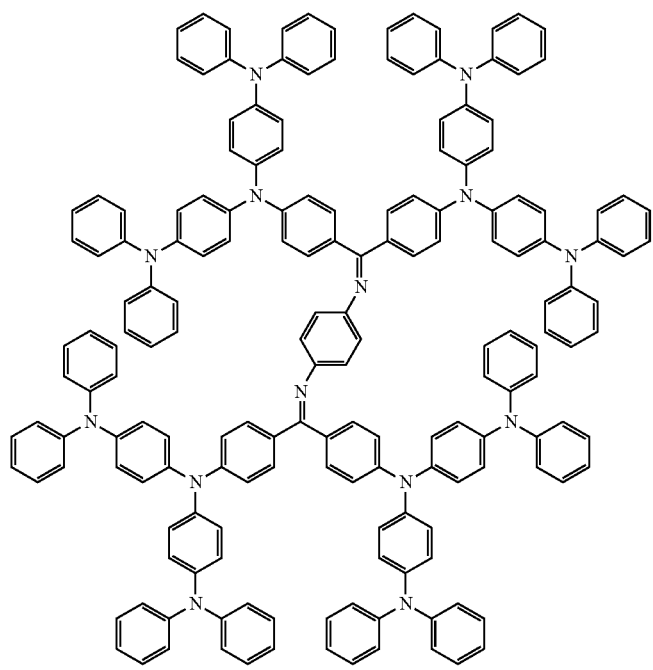

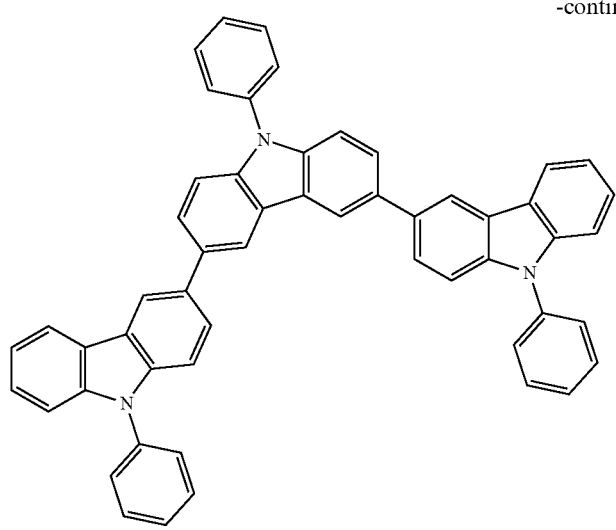
Next, examples of preferred compounds for use as an electron blocking material are mentioned below.
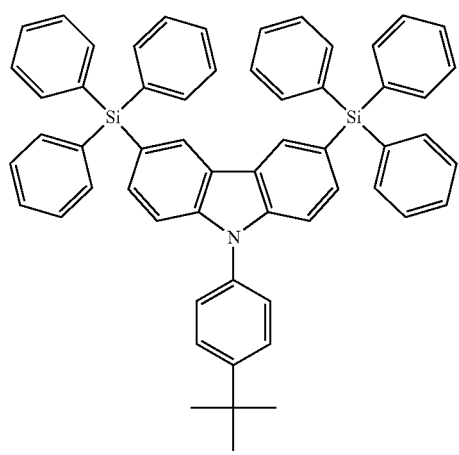
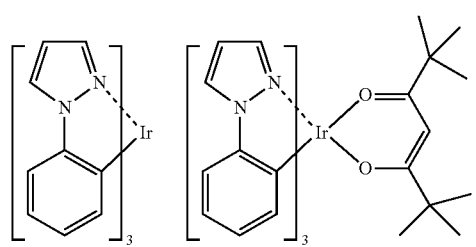
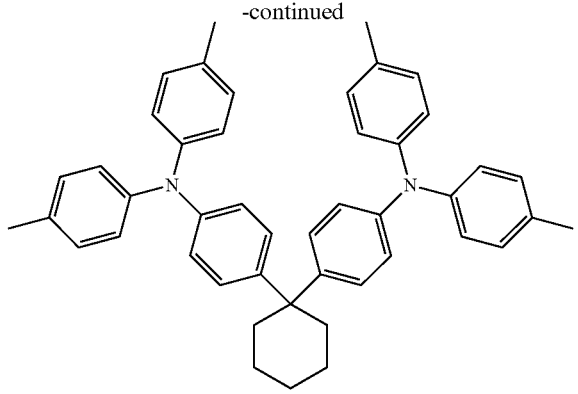
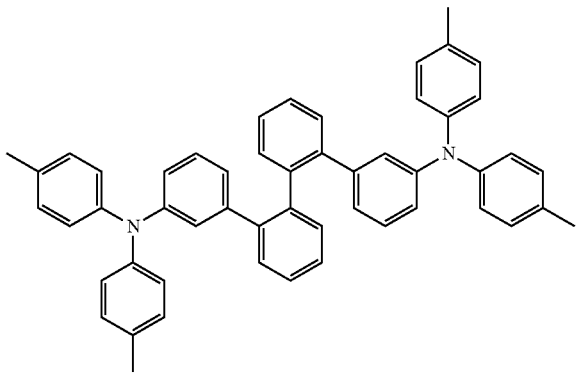

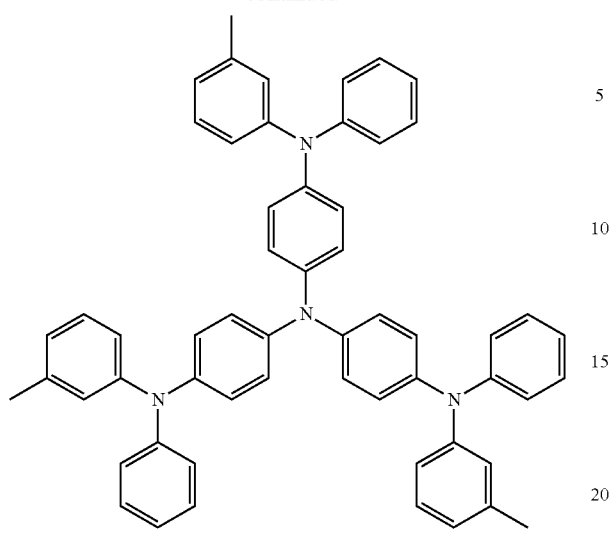
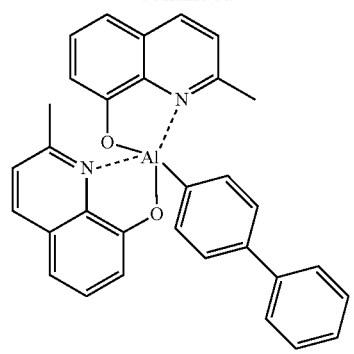
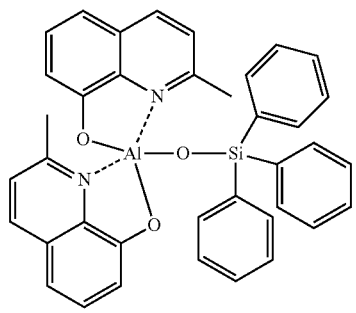
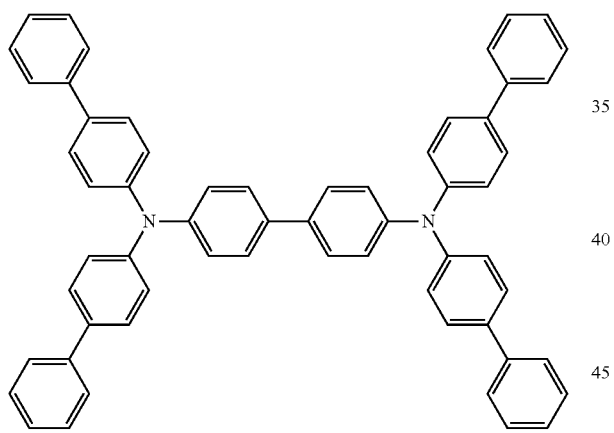
Next, examples of preferred compounds for use as a hole blocking material are mentioned below.
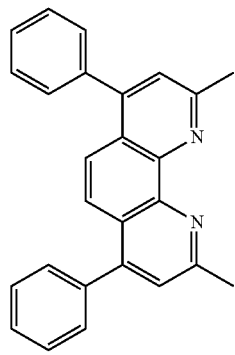
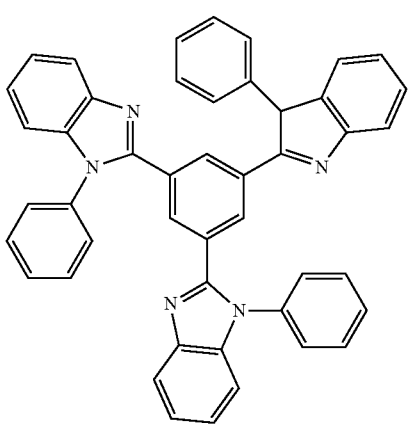

71
-continued
72
-continued
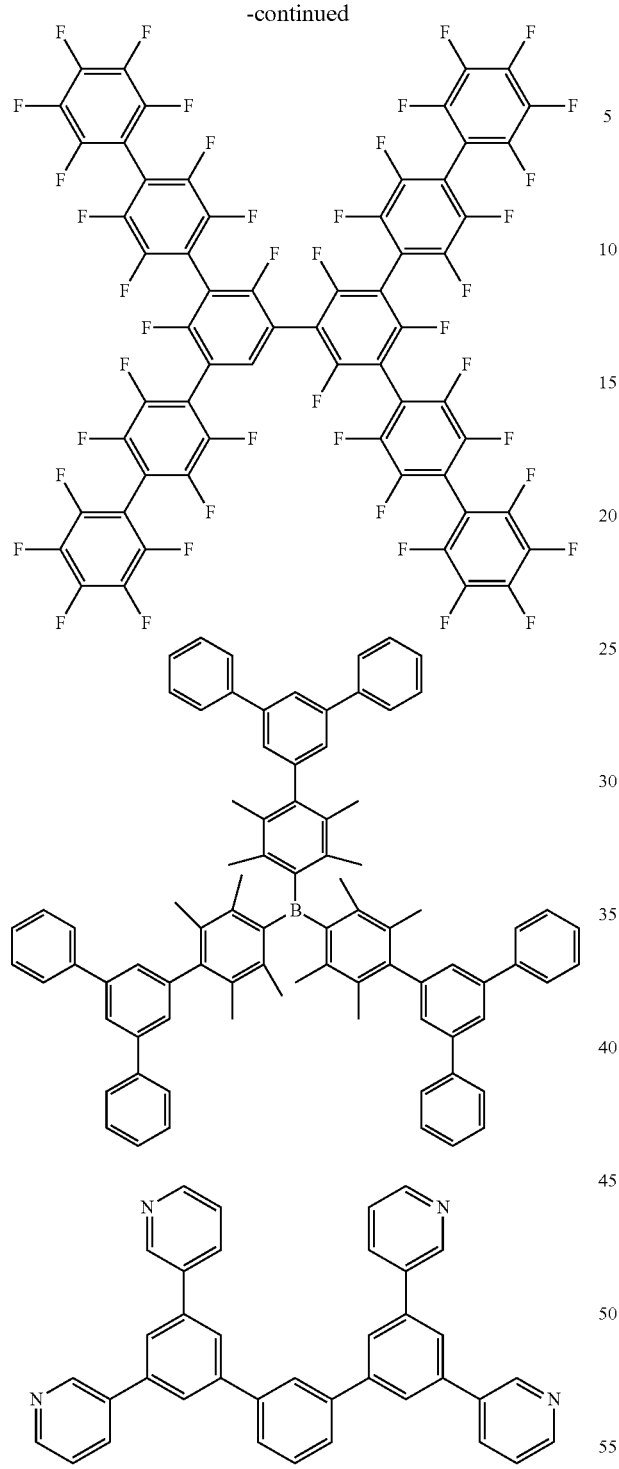
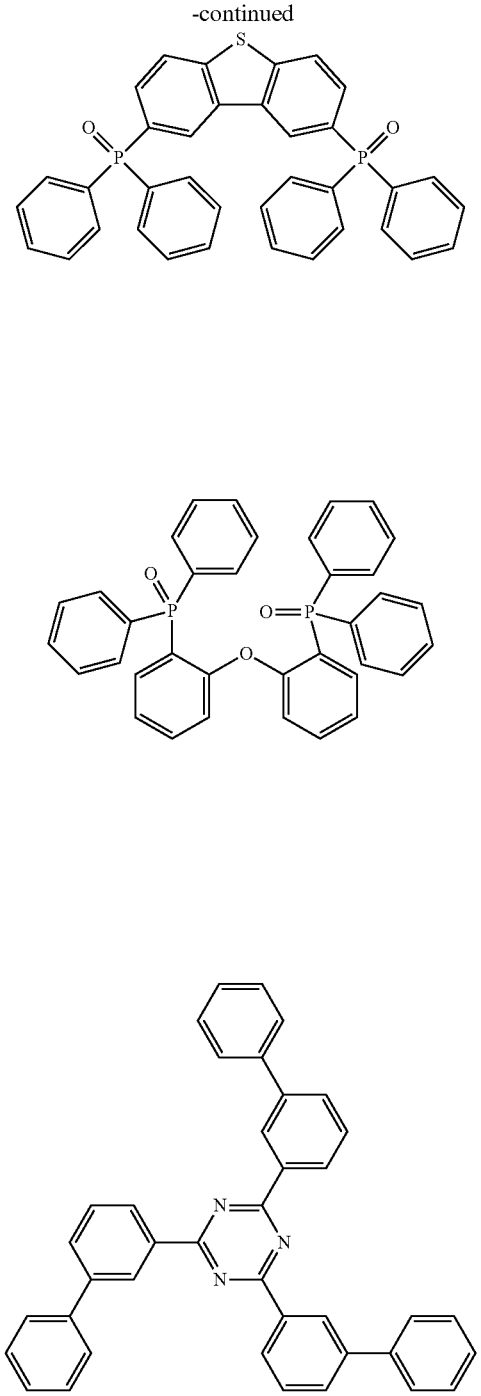
Next, examples of preferred compounds for use as an electron transport material are mentioned below.
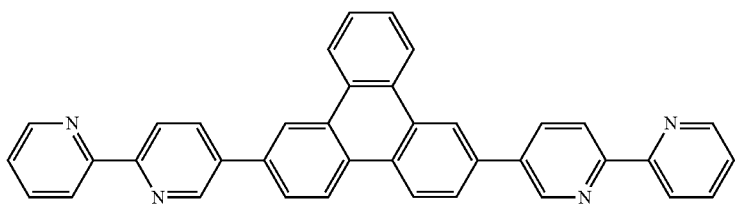

-continued
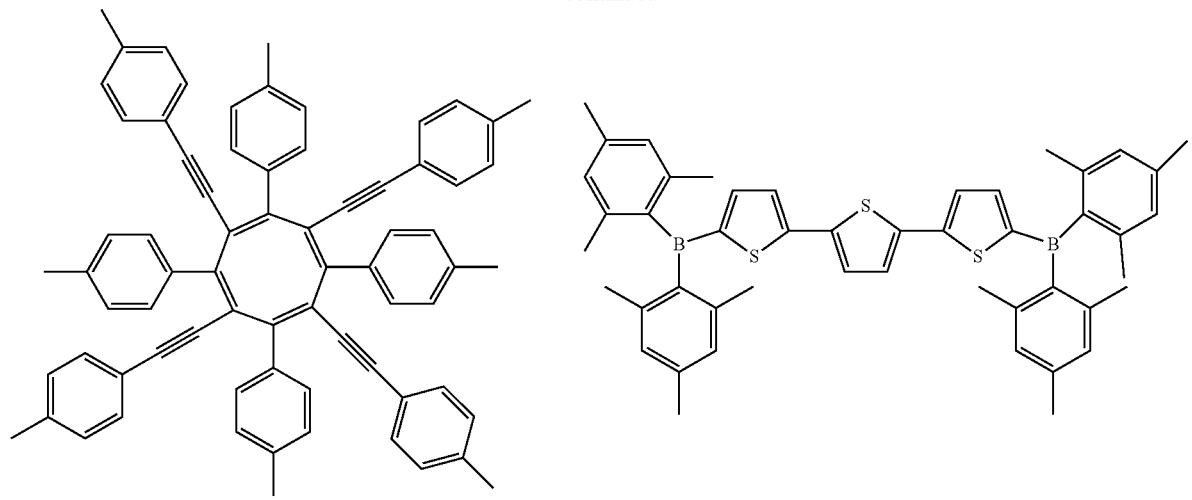
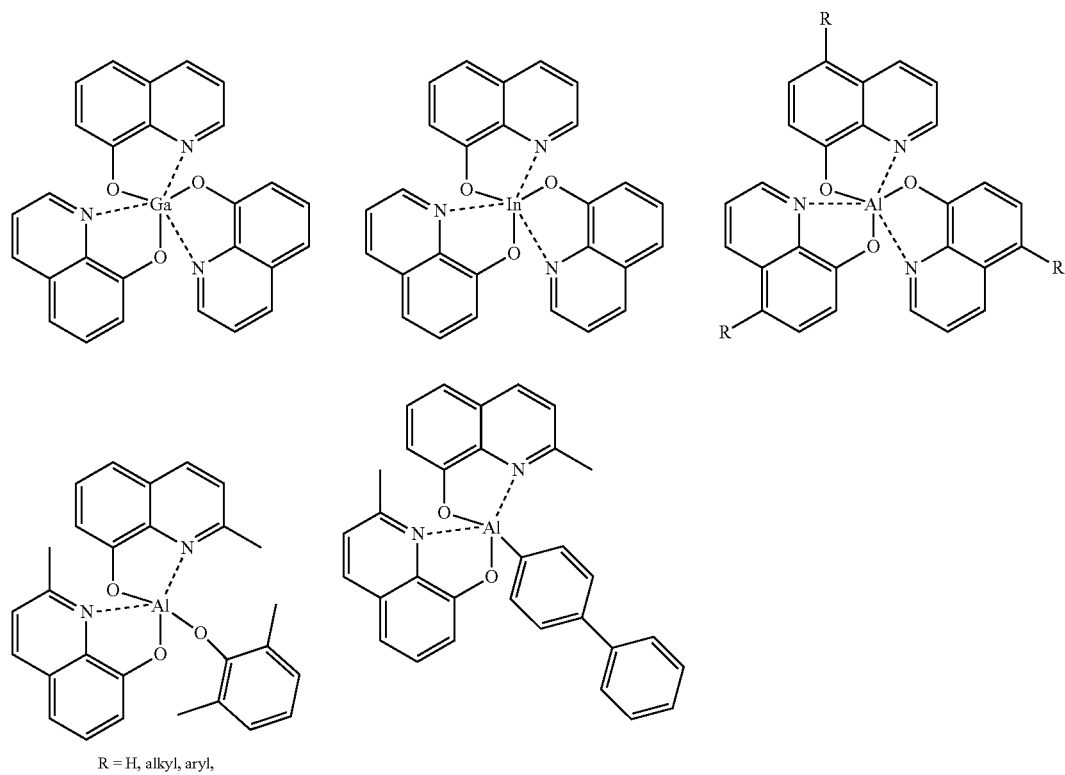
R = H, alkyl, aryl, heteroaryl
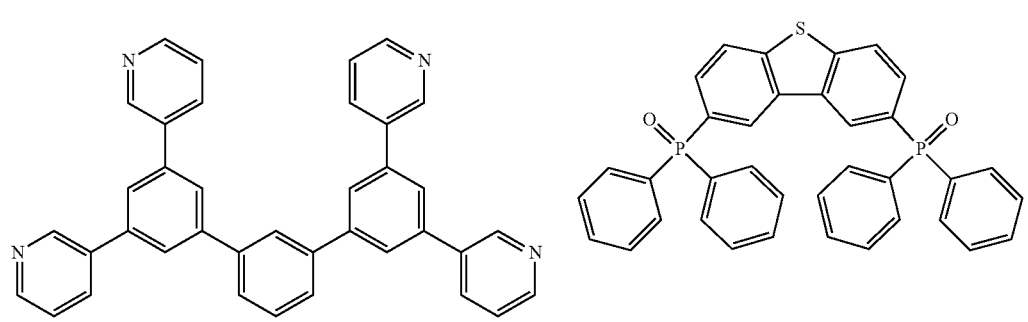

75
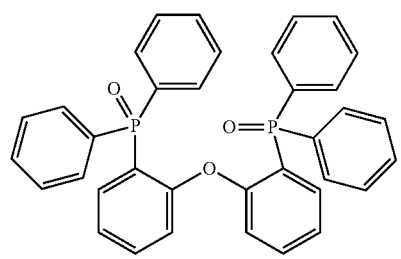
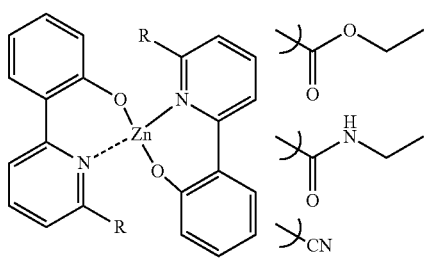
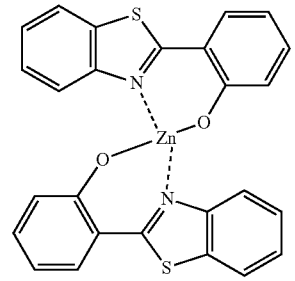
-continued
R = H
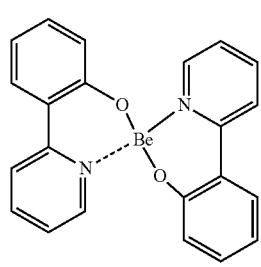
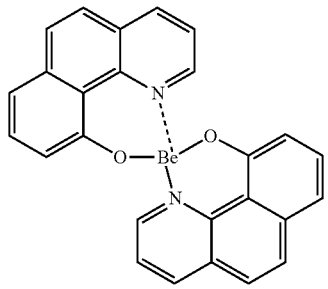
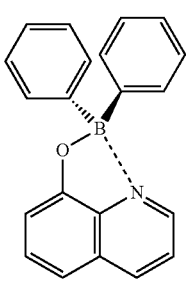
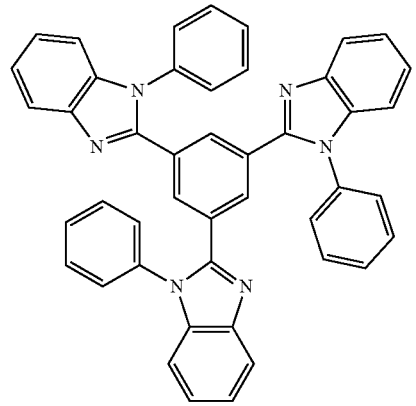
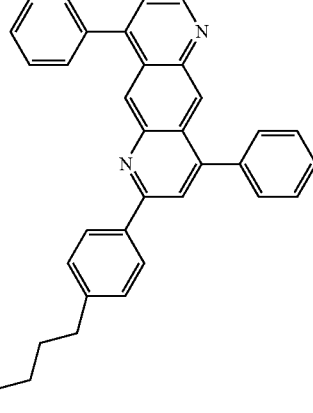
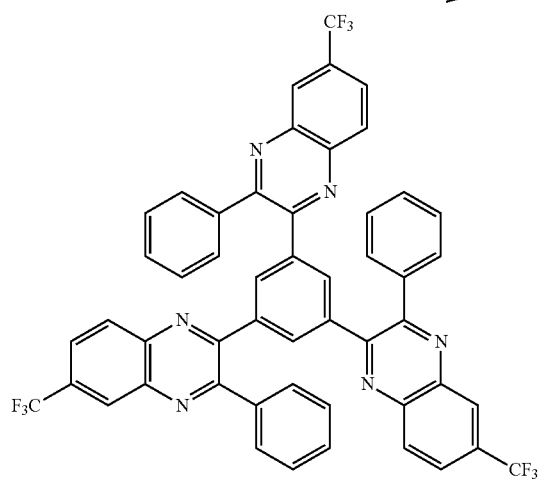
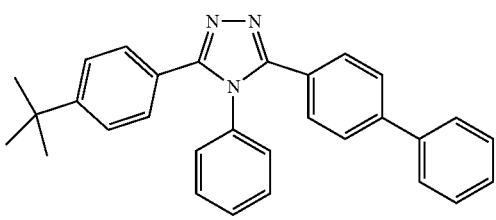
76

77
-continued
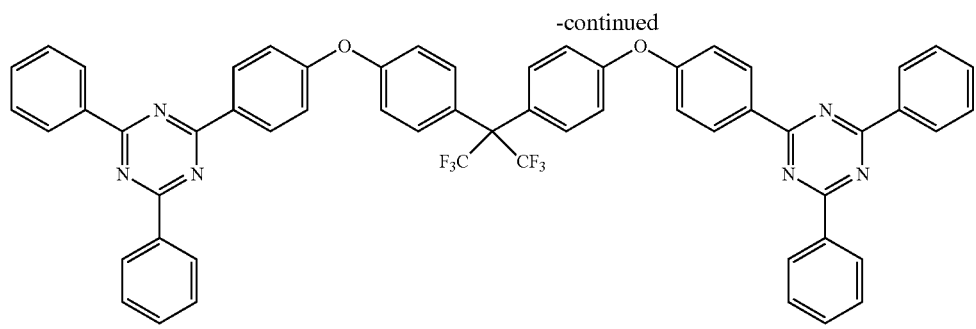
78
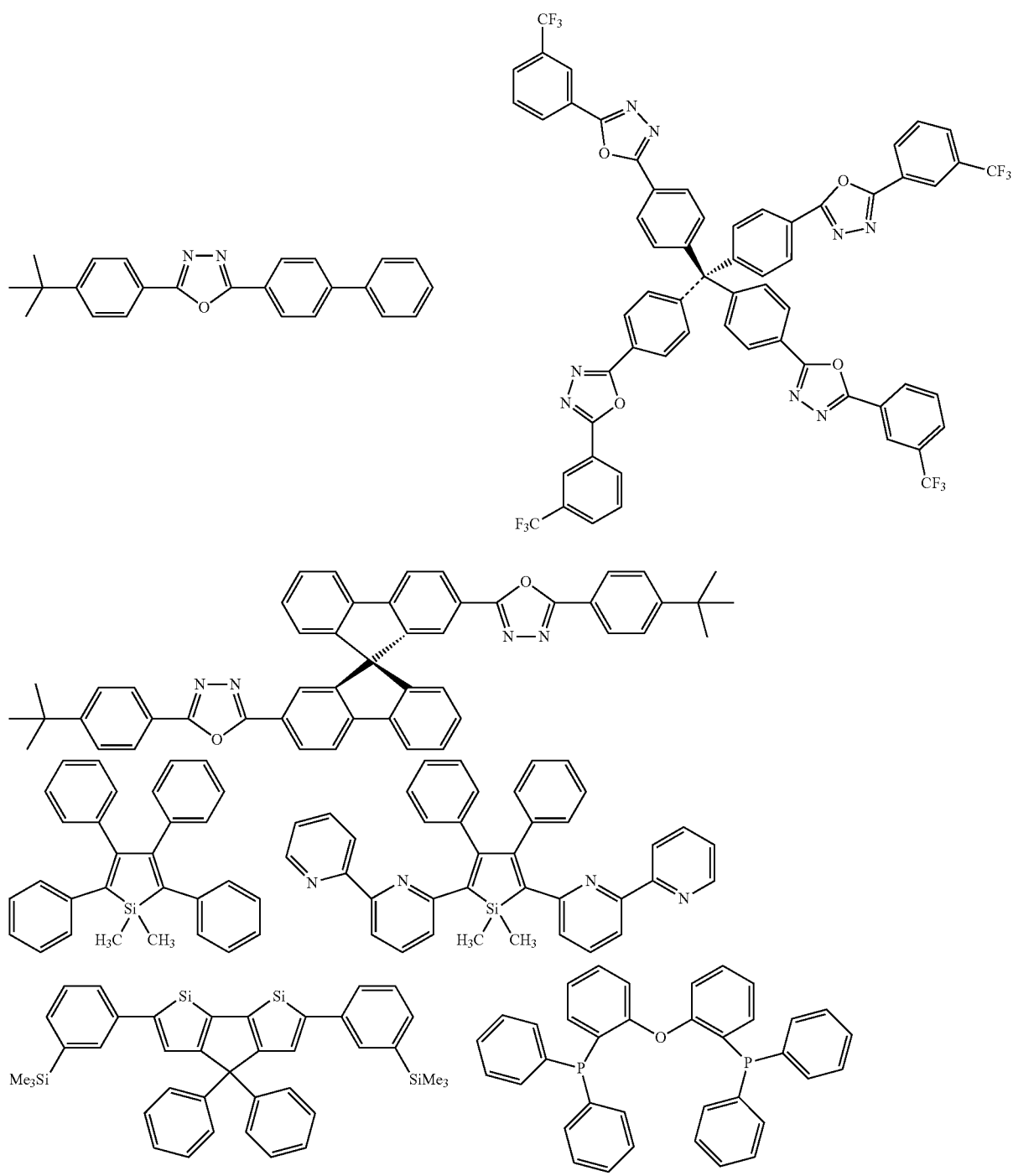

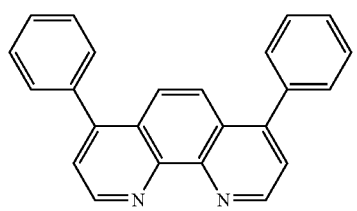 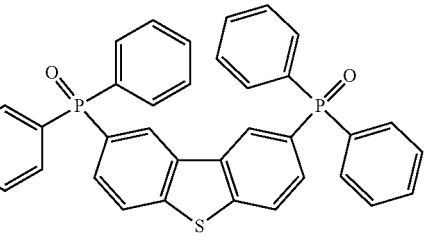

Next, examples of preferred compounds for use as an electron injection material are mentioned below.

Lif, CsF,

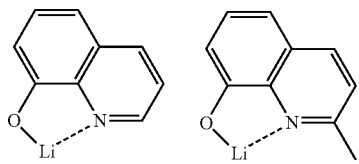

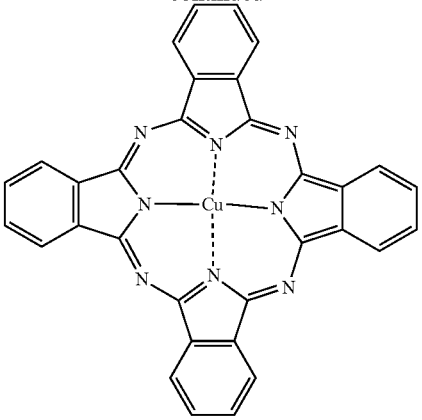

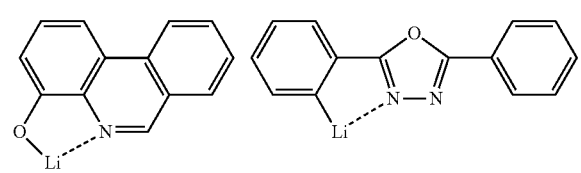

Further, examples of preferred compounds for use as additional materials are mentioned below. For example, these are considered to be added as a stabilization material.

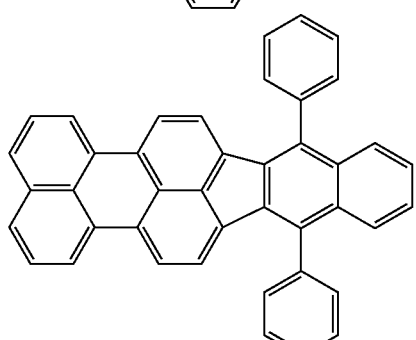

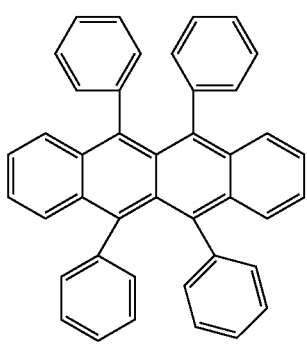

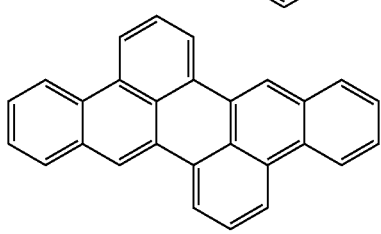

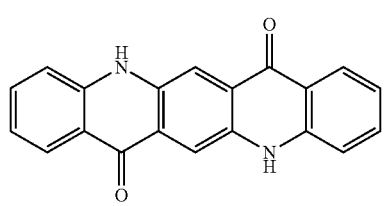

The organic electroluminescent device emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with an ordinary organic compound such as the compounds of the present invention at room temperature since the excited triplet energy thereof is unstable and is converted into heat or the like, that is, the lifetime is short and the compound may immediately deactivate. The excited triplet energy of an ordinary organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the present invention using the compound of the general formula (1) and the compound of the general formula (2), an organic light-emitting device having a high light emission efficiency can be provided. The organic light-emitting device such as the organic electroluminescent device of the present invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

[Composition and Film]

The present invention also provides a composition containing the compound represented by the general formula (1) and the compound represented by the general formula (2). The composition may be in a solution state, or may also be in a solid state. In the case where the composition is in a solution state, the compounds are dissolved in a solvent capable of dissolving both the compound represented by the general formula (1) and the compound represented by the general formula (2). For example, toluene can be used for the solvent.

The present invention also provides a film containing the compound represented by the general formula (1) and the compound represented by the general formula (2). In the film, the compound represented by the general formula (1) and the compound represented by the general formula (2) can be mixed, or the film can have a configuration where a layer containing the compound represented by the general formula (1) and a layer containing the compound represented by the general formula (2) are layered. The film containing the compound represented by the general formula (1) and the compound represented by the general formula (2) is useful as a film for organic light-emitting devices, but can be used in other use applications.

EXAMPLES

The features of the present invention will be described more specifically with reference to Examples given below. The materials, processes, procedures and the like shown below may be appropriately modified unless they deviate from the substance of the invention. Accordingly, the scope of the invention is not construed as being limited to the specific examples shown below.

Hereinunder, the light emission characteristics were evaluated using a UV-visible light-near IR spectrophotometer (available from Perkin Elmer, Lambda 950-PKA), a fluorescence spectrophotometer (available from Horiba, Ltd., FluoroMax-4), a multichannel spectrometer (available from Hamamatsu Photonics K.K., PMA-12C10027-01), a photoexcitation absolute luminescent quantum yield meter (available from Hamamatsu Photonics K.K., C9920PMA-11), a fluorescence lifetime meter (available from Hamamatsu Photonics K.K., C11367-25), and a streak camera (available from Hamamatsu Photonics K.K., U8167-1). In the present Examples, fluorescence having an emission lifetime of 100 ns or less is judged as instantaneous fluorescence, and fluorescence having an emission lifetime of 0.1 s or more is judged as delayed fluorescence.

(Synthesis Example 1) Synthesis of Compound 1

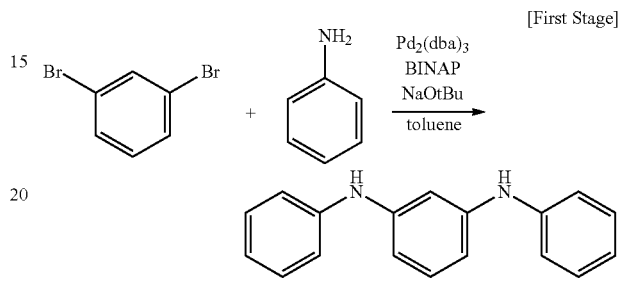

[First Stage]

In a nitrogen stream atmosphere, a flask containing 1,3-dibromobenzene (25.0 g, 106 mmol), aniline (20.3 ml, 223 mmol), tris(dibenzylideneacetone)dipalladium(0) (Pd$_2$(dba)$_3$) (971 mg, 1.06 mmol), 2,2'-bis(diphenylphosphino)-1,1'-binaphthyl (BINAP: 1.98 g, 3.18 mmol), NaOtBu (25.5 g, 265 mmol) and toluene (400 ml) was heated up to 110° C. and stirred for 18 hours. The reaction liquid was cooled to room temperature, and filtered through silica gel (eluent: toluene), and the solvent was removed through evaporation under reduced pressure to give a crude product. The resultant crude product was dissolved in toluene, an appropriate amount thereof was removed by distillation under reduced pressure, and hexane was added thereto for reprecipitation to give a white solid of $N^1,N^3$-diphenylbenzene-1,3-diamine (16.5 g, yield 60%).

$^1$H-NMR (400 MHz, CDCl$_3$): δ=5.63 (s, 2H), 6.60 (dd, 2H), 6.74 (t, 1H), 6.90 (t, 2H), 7.06 (d, 4H), 7.12 (t, 1H), 7.24 (dt, 4H).

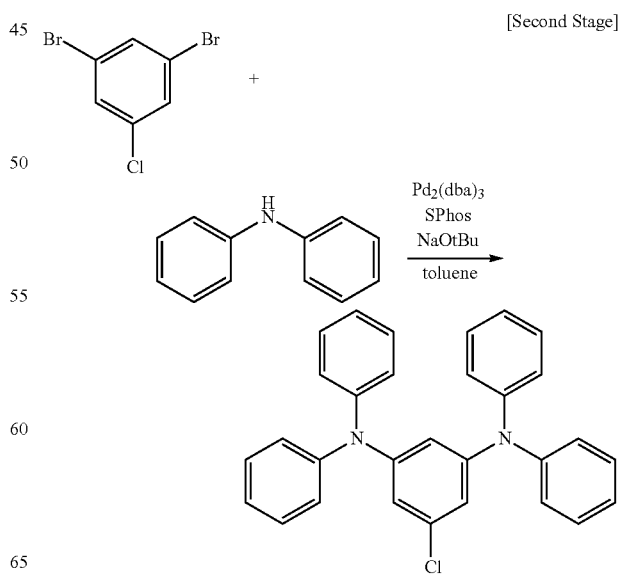

[Second Stage]

In a nitrogen stream atmosphere, a flask containing 1,3-dibromo-5-chlorobenzene (8.11 g, 30 mmol), diphenylamine (10.1 g, 60 mmol), Pd$_2$(dba)$_3$ (550 mg, 0.6 mmol), 2-dicyclohexylphenylphosphino-2',6'-dimethoxydiphenyl (SPhos: 0.493 g, 1.2 mmol), NaOtBu (8.60 g, 90 mmol) and toluene (300 ml) was heated up to 80° C. and stirred for 15 hours. The reaction liquid was cooled to room temperature, and filtered through silica gel (eluent: toluene), and the solvent was removed through evaporation under reduced pressure to give a crude product. The resultant crude product was dissolved in toluene, and evaporated under reduced pressure to give a saturated solution, then hexane was added thereto for reprecipitation to give a white solid of 5-chloro-N$^1$,N$^1$,N$^3$,N$^3$-tetraphenylbenzene-1,3-diamine (5.66 g, yield 43%).

$^1$H-NMR (400 MHz, CDCl$_3$): δ=6.56 (d, 2H), 6.64 (t, 1H), 7.00 (t, 4H), 7.05 (d, 8H), 7.21 (dd, 8H).

[Third Stage]

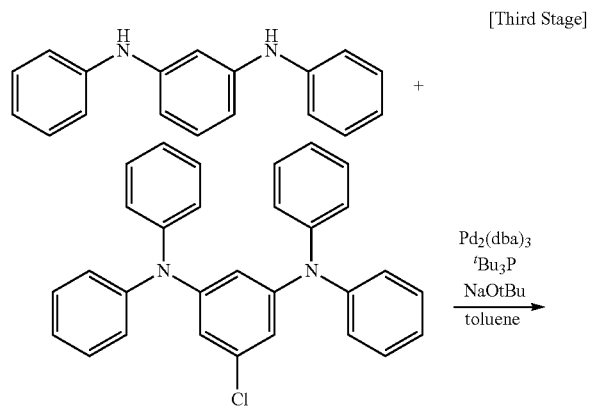

Pd$_2$(dba)$_3$
$^t$Bu$_3$P
NaOtBu
toluene

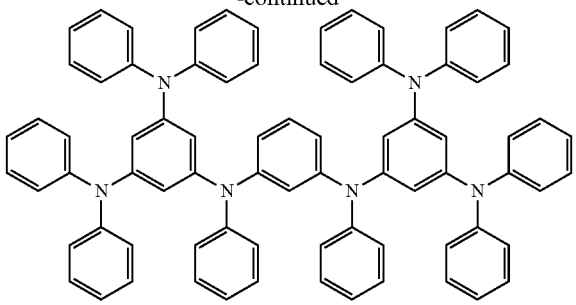

In a nitrogen stream atmosphere, a flask containing N$^1$,N$^3$-diphenylbenzene-1,3-diamine (1.34 g, 5.1 mmol) produced in the first stage, 5-chloro-N$^1$,N$^1$,N$^3$,N$^3$-tetraphenylbenzene-1,3-diamine (4.80 g, 11 mmol) produced in the second stage, Pd$_2$(dba)$_3$ (0.140 g, 0.15 mmol), tri-tert-butyl phosphine (60.7 mg, 0.30 mmol), NaOtBu (1.47 g, 15 mmol) and toluene (200 ml) was heated up to 110° C. and stirred for 8 hours. The reaction liquid was cooled to room temperature, and filtered through silica gel (eluent: toluene), and the solvent was removed through evaporation under reduced pressure to give a crude product. The resultant crude product was washed with hexane and methanol in that order to give a white solid of N$^1$,N$^{1'}$-(1,3-phenylene)bis(N$^1$,N$^3$,N$^3$,N$^5$,N$^5$-pentaphenylbenzene-1,3,5-triamine (4.80 g, yield 87%).

$^1$H-NMR (400 MHz, CDCl$_3$): δ=6.38 (d, 4H), 6.41 (t, 2H), 6.58 (dd, 2H), 6.70 (t, 1H), 6.88-6.90 (m, 14H), 6.85 (t, 1H), 6.99 (d, 16H), 7.08-7.15 (m, 20H).

[Fourth Stage]

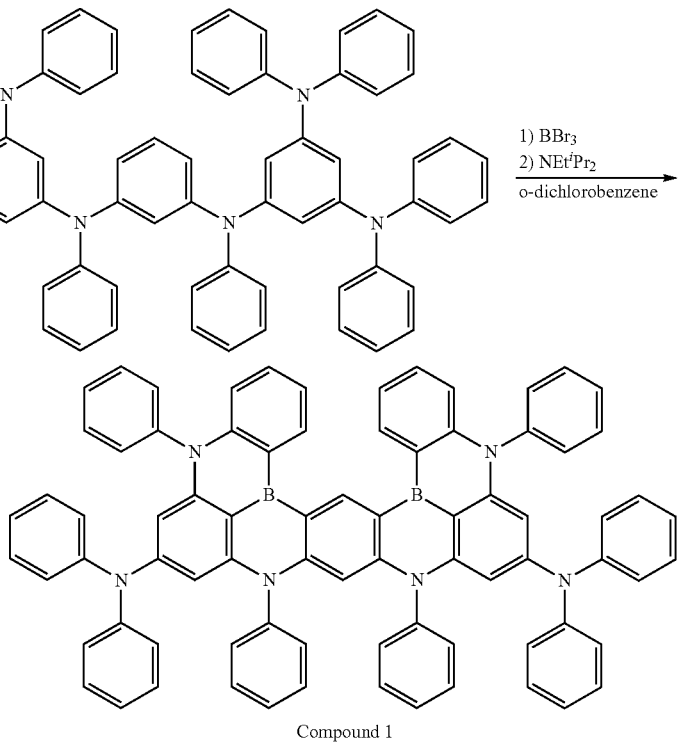

Compound 1

In a nitrogen atmosphere at room temperature, boron tribromide (1.13 ml, 12 mmol) was added to a flask containing N$^1$,N$^{1'}$-(1,3-phenylene)bis(N$^1$,N$^3$,N$^3$,N$^5$,N$^5$-pentaphenylbenzene-1,3,5-triamine (3.24 g, 3.0 mmol) and ortho-dichlorobenzene (400 ml). After the dropping, this was heated up to 180° C. and stirred for 20 hours. Subsequently, this was again cooled down to room temperature, and N,N-diisopropylethylamine (7.70 ml, 45 mmol) was added and stirred until heat generation ceased. Subsequently, at 60° C. under reduced pressure, the reaction solution was evaporated to give a crude product. The resultant crude product was washed with acetonitrile, methanol and toluene in that order, then purified through silica gel column chromatography (eluent: toluene), and the crude product was recrystallized twice with o-dichlorobenzene, and then purified through sublimation under a reduced pressure of 1×10$^{-4}$ mmHg at 440° C. to give 1.17 g of the compound 1.
$^1$H-NMR (400 MHz, CDCl$_3$): δ=5.72 (s, 2H), 5.74 (s, 2H), 5.86 (s, 1H), 6.83 (d, 2H), 6.88-6.93 (m, 12H), 7.05 (t, 8H), 7.12-7.19 (m, 6H), 7.24-7.26 (m, 4H), 7.05 (d, 4H), 7.12 (dd, 8H), 7.12-7.19 (m, 6H), 7.32 (d, 4H), 7.38 (dd, 2H), 7.42 (t, 2H), 7.46 (dd, 2H), 7.47 (dd, 4H), 9.30 (d, 2H), 10.5 (s, 1H).

$^{13}$C-NMR (101 MHz, CDCl$_3$): 99.5 (2C+2C), 103.4 (1C), 116.8 (2C), 120.0 (2C), 123.1 (4C), 125.3 (8C), 127.1 (2C), 127.6 (2C), 128.5 (8C), 129.6 (4C), 129.8 (4C), 130.2 (4C+2C), 130.3 (4C), 135.0 (2C), 142.1 (2C), 142.5 (2C), 143.3 (1C), 146.8 (4C), 147.9 (2C+2C), 148.0 (2C), 150.1 (2C), 151.1 (2C).

(Synthesis Example 2) Synthesis of Compound 2-38

[First Stage and Second Stage]

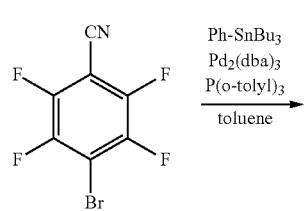
a

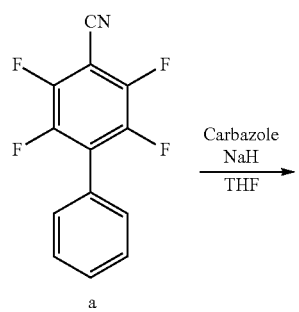

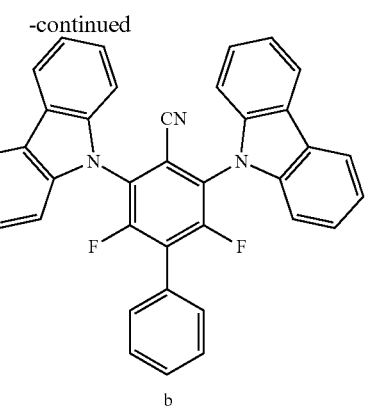
b

In a nitrogen stream atmosphere, tri(o-tolyl) phosphine (0.525 g, 1.72 mmol) and tris(dibenzylideneacetone)palladium(0) (1.57 g, 1.72 mmol) were added to a toluene solution (50 mL) of tributyltin chloride (5.06 g, 4.45 mL, 13.78 mmol) and 4-bromo-2,3,5,6-tetrafluorobenzonitrile (2.92 g, 11.50 mmol), heated up to 100° C., and stirred for 21 hours. The mixture was restored to room temperature, then quenched by adding water thereto, extracted with ethyl acetate, and filtered through Celite. Next, the organic layer was washed with saturated saline water, and dried with anhydrous magnesium sulfate. This was concentrated under reduced pressure, and the resultant mixture was purified through silica gel column chromatography (dichloromethane/hexane=1:2) to give a white solid of the compound (a) (2.42 g, 9.63 mmol, yield 83.7%).

$^1$H-NMR (500 MHz, CDCl$_3$, δ):7.56-7.51 (m, 3H), 7.48-7.45 (m, 2H)

ASAP Mass Spectrometry: Theoretical 251.0, Found 251.1

In a nitrogen stream atmosphere, 9H-carbazole (0.397 g, 2.38 mmol) was added to a tetrahydrofuran solution (10 mL) of sodium hydride (60% mineral oil dispersion, 0.125 g, 3.14 mmol), and stirred at room temperature for 1 hour. The mixture was cooled to −50° C., and the compound (a) (0.3 g, 1.19 mmol) was added thereto, then the cooling bath was removed, and with gradually restoring to room temperature, this was stirred for 22 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1:2) to give a yellow solid of the compound (b) (0.486 g, 0.89 mmol, yield 74.8%).

$^1$H-NMR (500 MHz, CDCl$_3$) δ: 8.16 (d, J=7.5 Hz, 4H), 7.62-7.59 (m, 2H), 7.54-7.49 (m, 7H), 7.38 (dt, J=7.5 Hz, 1.0 Hz, 4H), 7.30 (d, J=7.5 Hz, 4H)

ASAP Mass Spectrometry: Theoretical 545.2, Found 545.2

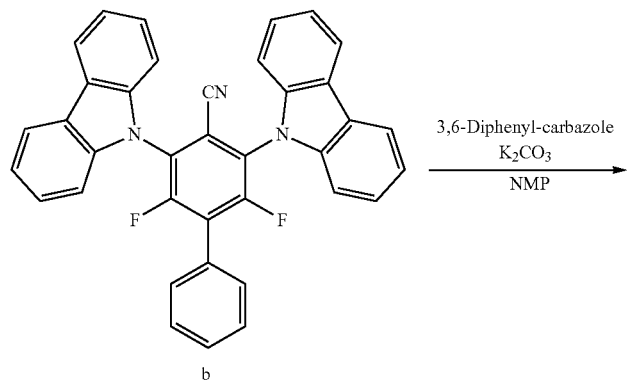

In a nitrogen stream atmosphere, the compound b (0.45 g, 0.825 mmol) was added to a 1-methyl-2-pyrrolidone solution (10 mL) of 3,6-diphenylcarbazole (0.66 g, 2.06 mmol) and potassium carbonate (0.43 g, 3.11 mmol), and stirred at 100° C. for 48 hours. The mixture was restored to room temperature, quenched by adding water thereto, extracted with ethyl acetate, and the organic layer was washed with saturated saline water and dried with anhydrous magnesium sulfate. This was concentrated under reduced pressure, and the resultant mixture was purified through silica gel column chromatography (chloroform/hexane=1:1) to give a yellow solid of the compound 2-38 (0.575 g, 0.502 mmol, yield 60.9%).

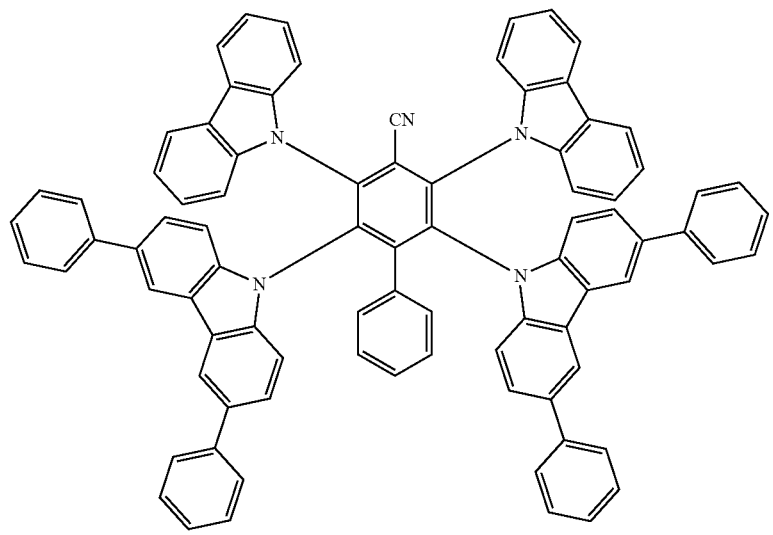

$^1$H-NMR (500 MHz, CDCl$_3$): δ=7.81 (d, J=1.5 Hz, 4H), 7.72-7.70 (m, 4H), 7.54-7.52 (m, 8H), 7.43 (t, J=7.5 Hz, 8H), 7.32 (t, J=7.5 Hz, 4H), 7.29-7.06 (m, 20H), 6.86-6.83 (m, 2H), 6.61-6.58 (m, 1H), 6.56-6.52 (m, 2H)

ASAP Mass Spectrometry: Theoretical 1143.4, Found 1143.4

(Synthesis Example 3) Synthesis of Compound 2-117

[First Stage]

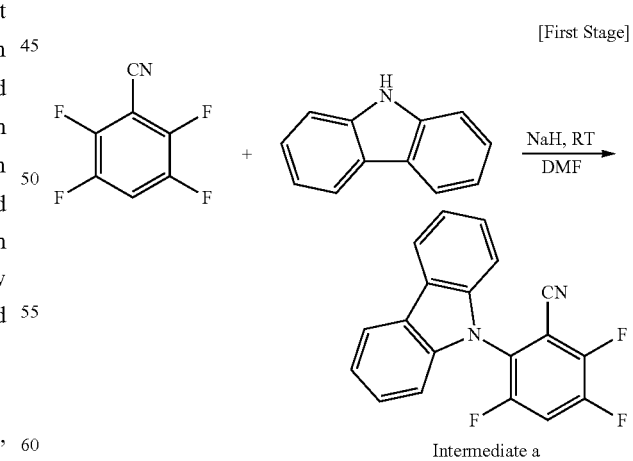

In a nitrogen atmosphere, 9H-carbazole (167 mg, 1 mmol) was dissolved in dry N,N-dimethylformamide (30 mL), then NaH (40 mg, 1 mmol) was added thereto at 0° C., and stirred at room temperature for 30 minutes. Subsequently, tetrafluorobenzonitrile (175 mg, 1 mmol) was added and stirred at room temperature for 16 hours. This was quenched with water, the precipitate was separated by filtration, and the crude product was purified through silica gel column chromatography to give the intermediate a (yield 193 mg, 60%).

$^1$H NMR (500 MHz, CDCl$_3$, 298 K, relative to Me$_4$Si): δ=8.16 (d, 2H, 7.5 Hz), 7.53-7.58 (m, 1H), 7.48 (t, 2H, 7.0 Hz), 7.38 (t, 2H, 7.5 Hz), 7.11 (d, 2H, 8.0 Hz); $^{13}$C NMR (126 MHz, CDCl$_3$): δ=155.8, 155.7, 153.8, 153.7, 150.9, 150.8, 150.7, 150.1, 150.0, 149.9, 148.8, 148.7, 148.6, 148.0, 147.9, 147.8, 140.0, 126.6, 124.4, 124.3, 124.3, 124.2, 124.2, 121.6, 120.8, 112.2, 112.0, 111.9, 111.8, 109.4, 109.3, 109.2, 109.2, 105.5, 105.4;

$^{19}$F NMR (471 MHz, CDCl$_3$): δ=−114.32 (m, 1H), −128.05 (m, 1H), −130.54 (m, 1H); MS (APCI) calcd. for C$_{19}$H$_9$F$_3$N$_2$: m/z=322.08; found: 322.17 [M]$^+$.

$^1$H NMR (500 MHz, Acetone-d$_6$, 298 K, relative to Me$_4$Si): δ=9.07 (s, 1H), 8.36 (s, 2H), 8.29 (d, 4H, 10.0 Hz), 7.95-8.00 (m, 10H), 7.55-7.70 (m, 18H), 7.30-7.45 (m, 20H), 7.18 (t, 2H, 7.0 Hz). $^{13}$C NMR (126 MHz, Acetone-d$_6$): δ=143.1, 143.1, 142.1, 142.0, 141.6, 141.5, 141.0, 140.7, 140.2, 140.0, 136.2, 135.9, 135.8, 130.6, 130.5, 128.8, 128.8, 128.7, 128.5, 128.4, 127.6, 126.8, 126.7, 126.7, 126.5, 126.42, 125.8, 122.9, 122.0, 120.5, 120.4, 120.4, 113.4, 112.9, 112.7, 112.7.

MS (APCI) calcd. for C$_{91}$H$_{57}$N$_5$: m/z=1220.5; found: 1221.0 [M]$^+$.

Elemental analysis calcd. (%) for C$_{91}$H$_{57}$N5: C 89.55, H 4.71, N 5.74; found: C 89.51, H 4.65, N 5.72.

(Preliminary Measurement) Measurement of Compound 1 and Compound 2-38

[Second Stage]

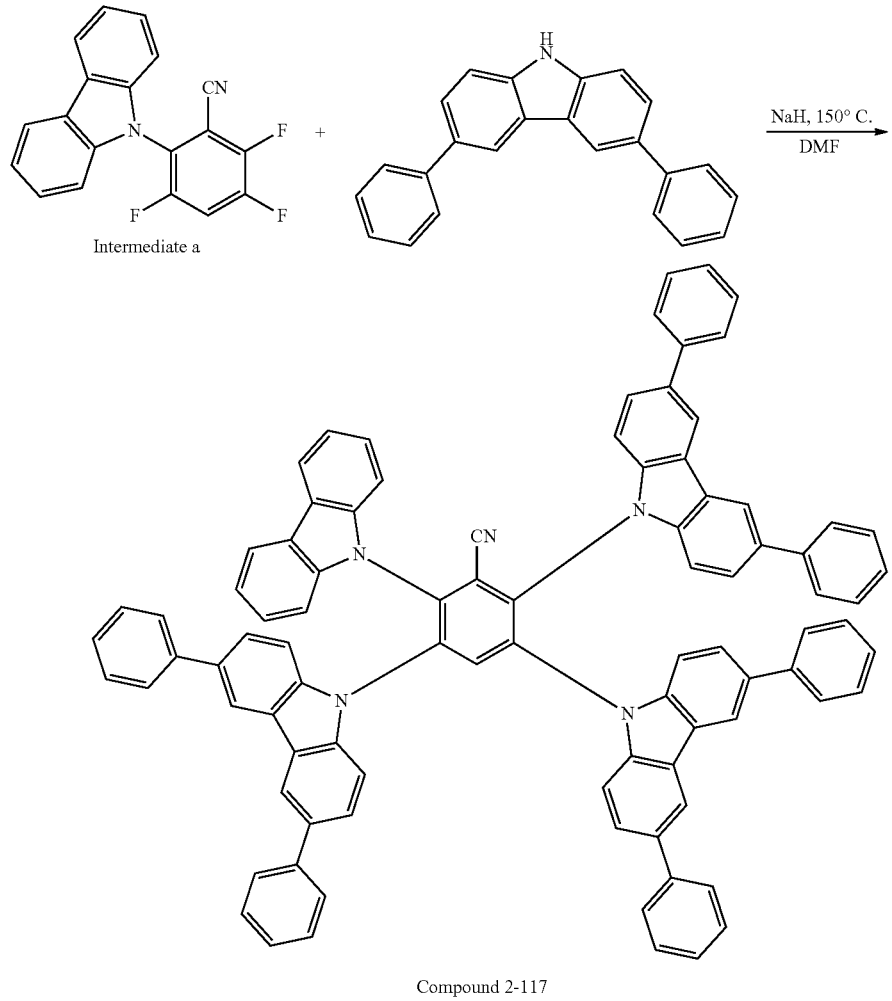

Compound 2-117

In a nitrogen atmosphere, 3,6-diphenyl-9H-carbazole (957 mg, 3 mmol) was dissolved in dry N,N-dimethylformamide (30 mL), then NaH (120 mg, 3 mmol) was added thereto at 0° C., and stirred at room temperature for 30 minutes. Subsequently, 2-(9H-carbazol-9-yl)-3,5,6-trifluorobenzonitrile (322 mg, 1 mmol) was added, and heated at 150° C. for 16 hours. This was quenched with water and the precipitate was separated by filtration, and the crude product was purified through column chromatography to give the compound 2-117 (yield 976 mg, 80%).

A toluene solution of the compound 1 and a toluene solution of the compound 2-38 were prepared, each having a concentration of $10^{-5}$ mol/L.

The toluene solution of the compound 1 and the toluene solution of the compound 2-38 were subjected to spectrometry at 300 K, and the results are shown in FIG. 2. The upper stage of FIG. 2 shows an absorption spectrum of the toluene solution of the compound 1 and an emission spectrum of the toluene solution of the compound 2-38 irradiated with excitation light having a wavelength of 360 nm. Overlapping of the two was confirmed in a region at around 450 nm. An emission spectrum of the toluene solution of the compound 1, irradiated with excitation light having a wavelength of 360 nm, is shown as a broken line in the lower stage of FIG. 2.

The lowest excited singlet energy level ($E_{S1}$) and the lowest excited triplet energy level ($E_{T1}$) of the compound 2-38 was measured according to the following process.

(1) Lowest Excited Singlet Energy Level ($E_{S1}$)

A tangent line was drawn to the rising on the short wavelength side of the emission spectrum of the toluene solution of the compound 2-38, and the wavelength value λedge [nm] at the intersection between the tangent line and the horizontal axis was read. The wavelength value was converted into an energy value according to the following conversion expression to calculate $E_{S1}$. $E_{S1}$ was 2.79 eV.

Conversion Expression: $E_{S1}$ [eV]=1239.85/λedge (2) Lowest Excited Triplet Energy Level ($E_{T1}$)

The toluene solution of the compound 2-38 was cooled to 77 [K] and irradiated with excitation light (337 nm), and using a streak camera, the phosphorescence intensity thereof was measured. Emission data from 1 millisecond after irradiation with the excitation light to 10 milliseconds after the irradiation were integrated to give a phosphorescent spectrum on a vertical axis indicating an emission intensity and a horizontal axis indicating a wavelength. A tangent line was drawn to the rising of the phosphorescent spectrum on the short wavelength side, and the wavelength value kedge [nm] at the intersection between the tangent line and the horizontal axis was read. The wavelength value was converted into an energy value according to the following conversion expression to calculate $E_{T1}$.

Conversion Expression: $E_{T1}$ [eV]=1239.85/λedge

The tangent line to the rising of the phosphorescent spectrum on the short wavelength side was drawn as follows. While moving on the spectral curve from the short wavelength side of the phosphorescent spectrum toward the maximum value on the shortest wavelength side among the maximum values of the spectrum, a tangent line at each point on the curve toward the long wavelength side was taken into consideration. With rising thereof (that is, with increase in the vertical axis), the inclination of the tangent line increases. The tangent line drawn at the point at which the inclination value has a maximum value was referred to as the tangent line to the rising on the short wavelength side of the phosphorescent spectrum.

The maximum point having a peak intensity of 10% or less of the maximum peak intensity of the spectrum was not included in the maximum value on the above-mentioned shortest wavelength side, and the tangent line drawn at the point which is closest to the maximum value on the shortest wavelength side and at which the inclination value has a maximum value was referred to as the tangent line to the rising on the short wavelength side of the phosphorescent spectrum.

(3) Measurement Results

The lowest excited singlet energy level ($E_{S1}$) of the compound 2-38 was 2.79 eV, and the lowest excited triplet energy level ($E_{T1}$) thereof was 2.66 eV Calculation of $E_{S1}$-$E_{T1}$ gave $\Delta E_{ST}$ of 0.13 eV.

Example 1

Preparation and analysis of thin film containing compound 1 and compound 2-38

Under a vacuum degree of $5\times10^{-4}$ Pa or less, the compound 1, the compound 2-38 and mCBP [3,3'-di(9H-carbazol-9-yl)-1,1'-biphenyl] were co-deposited on a quartz substrate from different evaporation sources to form thereon a thin film having a thickness of 50 nm (compound 1, 1% by weight; compound 2-38, 25% by weight; mCBP, 74% by weight). This thin film is referred to as a thin film of Example 1.

The emission spectrum of the thin film of Example 1, irradiated with excitation light having a wavelength of 360 nm, is shown as a full line in the lower stage of FIG. 2 (FWHM, 20 nm). This was confirmed to be conformable with the emission spectrum of the compound 1. The photoluminescence quantum yield of the thin film of Example 1 is 75%, and the delayed component was 30%. Here, the fluorescence having an emission lifetime of less than 1 μm was judged to be instantaneous fluorescence, and the fluorescence having an emission lifetime of 0.1 μs or more was judged to be delayed fluorescence, and the proportion of the delayed component was determined.

Example 2

Preparation and analysis of organic electroluminescent device containing compound 1 and compound 2-38

On a glass substrate having, as formed thereon, an anode of indium tin oxide (ITO) having a thickness of 50 nm, thin films were laminated according to a vacuum evaporation method under a vacuum degree of $2\times10^{-5}$ Pa.

First, on ITO, HATCN was vapor-deposited to have a thickness of 10 nm to form a hole injection layer, and then TrisPCz was vapor-deposited thereon to have a thickness of 30 nm to form a hole transport layer. Subsequently, mCBP was vapor-deposited to have a thickness of 5 nm to form an electron blocking layer. Next, the compound 1, the compound 2-38 and mCBP were co-deposited from different evaporation sources to form a light-emitting layer having a thickness of 50 nm (compound 1, 1% by weight; compound 2-38, 25% by weight; mCBP, 74% by weight). On this, SF3-TRZ was vapor-deposited to have a thickness of 10 nm to form a hole blocking layer, and further on this, SF3-TRZ: LiQ (weight ratio 7:3) was vapor-deposited to have a thickness of 20 nm to be an electron transport layer. Further, LiQ was formed thereon to have a thickness of 2 nm, and then aluminum (Al) was formed to have a thickness of 100 nm to be a cathode, thereby producing an organic electroluminescent device of Example 2.

Example 3

Preparation and measurement of organic electroluminescent device containing compound 8 and compound 2-117

On a glass substrate having, as formed thereon, an anode of indium tin oxide (ITO) having a thickness of 50 nm, thin films were laminated according to a vacuum evaporation method under a vacuum degree of $2\times10^{-5}$ Pa.

First, on ITO, HATCN was vapor-deposited to have a thickness of 10 nm to form a hole injection layer, and then TrisPCz was vapor-deposited thereon to have a thickness of 30 nm to form a hole transport layer. Subsequently, mCBP was vapor-deposited to have a thickness of 5 nm to form an electron blocking layer. Next, the compound 8, the compound 2-117 and mCBP were co-deposited from different evaporation sources to form a light-emitting layer having a thickness of 30 nm (compound 8, 0.5% by weight; compound 2-117, 15% by weight; mCBP, 84.5% by weight). On this, SF3-TRZ was vapor-deposited to have a thickness of 10 nm to form a hole blocking layer, and further on this, SF3-TRZ:LiQ (weight ratio 7:3) was vapor-deposited to have a thickness of 20 nm to be an electron transport layer. Further, LiQ was formed thereon to have a thickness of 2 nm, and then aluminum (Al) was formed to have a thickness of 100 nm to be a cathode, thereby producing an organic electroluminescent device of Example 3.

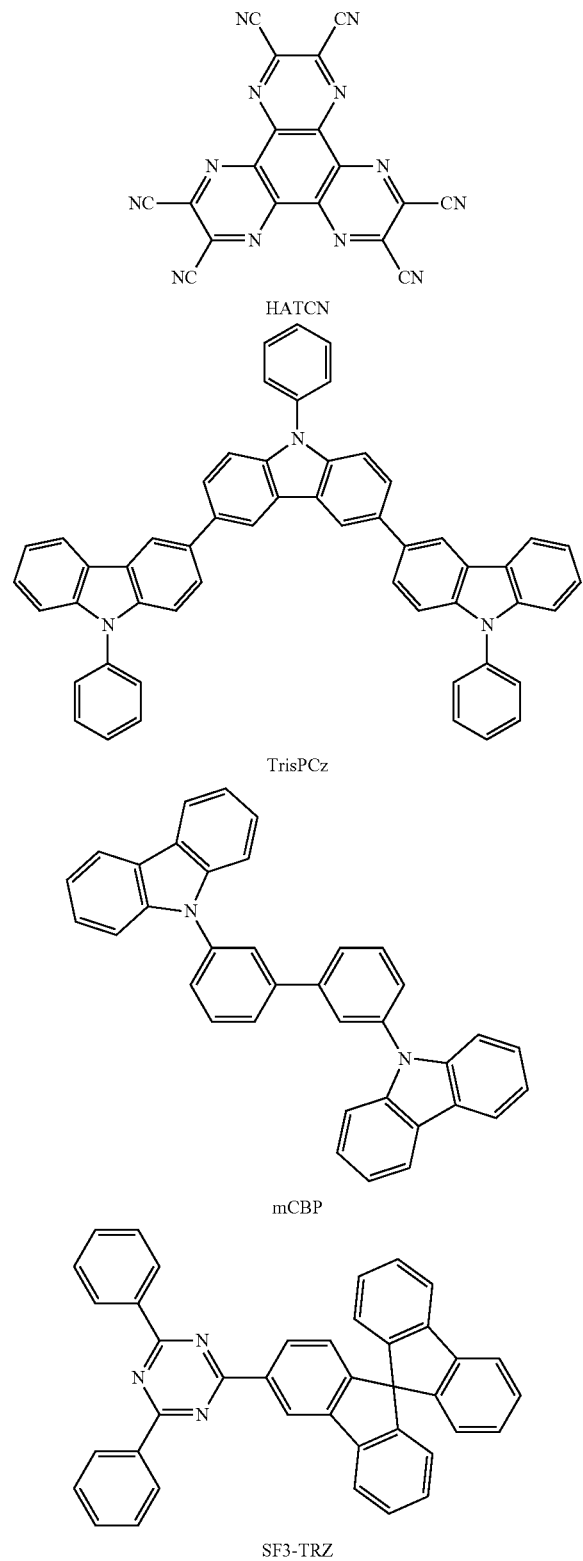

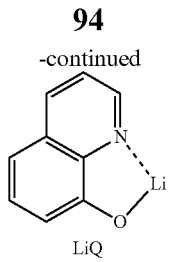

LiQ

The emission from the organic electroluminescent device of Example 2 was good blue emission such that, in the CIE-XYZ chromaticity coordinate system, the chromaticity coordinate x is 0.151 and y is 0.256. In the fluorescent spectrum of the organic electroluminescent device of Example 2, the emission maximum wavelength was the same as that in the fluorescent spectrum of the compound 1, which confirmed that the emission was from the compound 1. FIG. 3 shows transient decay curves of the device of Example 2, a comparative organic electroluminescent device (comparative device 1) differing from the device only in that the light-emitting layer was formed of the compound 1 (1% by weight) and mCBP (99% by weight), and a comparative organic electroluminescent device (comparative device 2) differing from the same only in that the light-emitting layer was formed of the compound 2-38 (25% by weight) and mCBP (75% by weight). Between the comparative device 1 and the device of Example 2, the proportion of the delayed component increased in the latter, which confirmed energy transfer from the compound 2-38 to the compound 1.

The external quantum efficiency of the organic electroluminescent device of Example 2 was more than 20% at 1000 nit (1.8 lm/W) and was high. On the other hand, the external quantum efficiency of the comparative organic electroluminescent device (comparative device 1) that differs only in that the light-emitting layer is formed of the compound 1 (1% by weight) and mCBP (99% by weight) was 8%, from which it is known that the organic electroluminescent device of Example 2 achieved a significant increase in the quantum efficiency. The time taken until the emission intensity of the organic electroluminescent device of Example 2 reached 95% at the start of the measurement (LT95) was about 100 hours at 750 nit (1.35 lm/W), which confirmed that the device has a long lifetime.

The organic electroluminescent device of Example 3 had an emission maximum wavelength of 469 nm, and an external quantum efficiency of at most 22.5%. Example 3 also confirmed that the organic electroluminescent device of the present invention has a high light emission efficiency.

INDUSTRIAL APPLICABILITY

The organic light-emitting device of the present invention has a high light emission efficiency. In addition, according to the present invention, a high-efficiency organic light-emitting device capable of emitting good blue light can be provided. Consequently, the industrial applicability of the present invention is great.

REFERENCE SIGNS LIST

1 Substrate
2 Anode
3 Hole Injection Layer
4 Hole Transport Layer
5 Light-Emitting Layer
6 Electron Transport Layer
7 Cathode

The invention claimed is:

1. An organic light-emitting device containing both a compound having one or more structures represented by the following general formula (1), and a compound represented by the following general formula (2a):

General Formula (1)

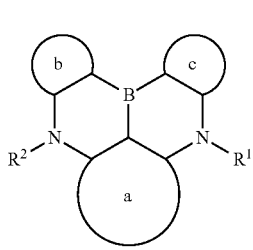

wherein ring a, ring b and ring c each independently represent a benzene ring that may be condensed with any other ring to form an aryl ring or a heteroaryl ring, and at least one hydrogen atom in these rings may be substituted; $R^1$ and $R^2$ each independently represent a substituted or unsubstituted aryl group, or a substituted or unsubstituted heteroaryl group bonding via the benzene ring; $R^1$ may bond to the carbon atom neighboring to the bonding position (atom) to N in ring a and/or ring c via —O—, —S—, —C(—$R^{c1}$)$_2$— or a single bond; $R^2$ may bond to the carbon atom neighboring to the bonding position (atom) to N in ring a and/or ring b via —O—, —S—, —C(—$R^{c2}$)$_2$— or a single bond; $R^{c1}$ and $R^{c2}$ each independently represent a hydrogen atom or an alkyl group;

General Formula (2a)

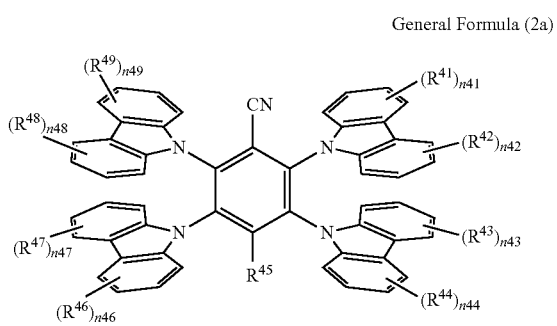

wherein $R^{41}$ to $R^{44}$, and $R^{46}$ to $R^{49}$ in general formula (2a) each independently represent a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group, but all four substituted or unsubstituted carbazol-9-yl groups bonding to benzonitrile in general formula (2a) are not the same; n41 to n44, and n46 to n49 each independently represent an integer of any of 0 to 4; and $R^{45}$ represents a hydrogen atom, a substituted or unsubstituted aryl group, a substituted or unsubstituted carbazol-9-yl group, or a cyano group.

2. The organic light-emitting device according to claim 1, wherein the compound having one or more structures represented by the general formula (1) is a compound having two structures represented by the general formula (1).

3. The organic light-emitting device according to claim 2, wherein the compound represented by the general formula (1) is a compound represented by the following general formula (1a):

General Formula (1a)

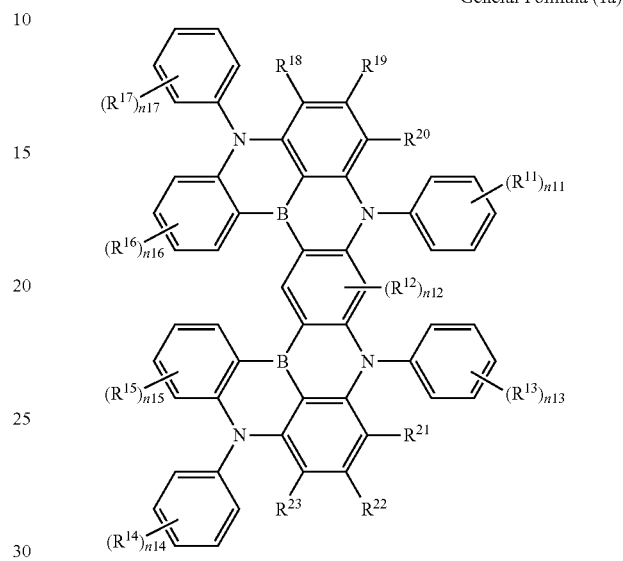

wherein $R^{11}$ to $R^{17}$ each independently represent a substituent, $R^{18}$ to $R^{23}$ each independently represent a hydrogen atom or a substituent, n11, n13, n14 and n17 each independently represent an integer of any of 0 to 5, n12 represents an integer of any of 0 to 2, n15 and n16 each independently represent an integer of any of 0 to 4.

4. The organic light-emitting device according to claim 3, wherein $R^{19}$ and $R^{22}$ each independently represent a substituent.

5. The organic light-emitting device according to claim 1, containing the compound represented by the general formula (1) in the light-emitting layer.

6. The organic light-emitting device according to claim 1, containing the compound represented by the general formula (1) and the compound represented by the general formula (2) in the same layer.

7. A composition containing both a compound represented by the following general formula (1) and a compound represented by the following general formula (2a):

General Formula (1)

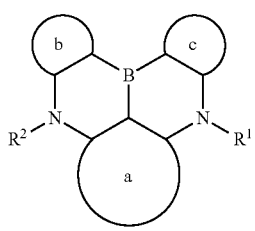

wherein ring a, ring b and ring c each independently represent a benzene ring that may be condensed with any other ring to form an aryl ring or a heteroaryl ring, and at least one hydrogen atom in these rings may be substituted; $R^1$ and $R^2$ each independently represent a substituted or unsubstituted aryl group, or a substituted or unsubstituted heteroaryl group bonding via the benzene ring; $R^1$ may bond to the carbon atom neighboring to the bonding position (atom) to N in ring a and/or ring c via —O—, —S—, —C(—$R^{c1}$)$_2$— or a single bond; $R^2$ may bond to the carbon atom neighboring to the bonding position (atom) to N in ring a and/or ring b via —O—, —S—, —C(—$R^{c2}$)$_2$— or a single bond; $R^{c1}$ and $R^{c2}$ each independently represent a hydrogen atom or an alkyl group;

General Formula (2a)

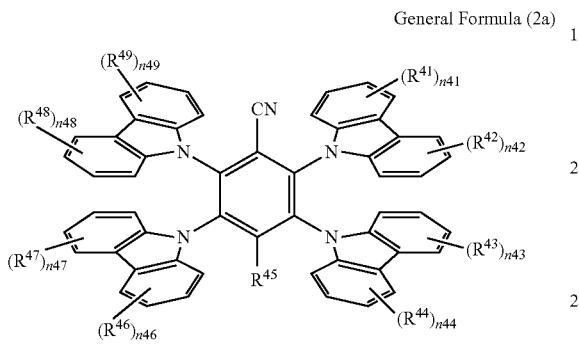

wherein $R^{41}$ to $R^{44}$, and $R^{46}$ to $R^{49}$ in general formula (2a) each independently represent a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group, but all four substituted or unsubstituted carbazol-9-yl groups bonding to benzonitrile in general formula (2a) are not the same; n41 to n44, and n46 to n49 each independently represent an integer of any of 0 to 4; and $R^{45}$ represents a hydrogen atom, a substituted or unsubstituted aryl group, a substituted or unsubstituted carbazol-9-yl group, or a cyano group.

8. A film containing both a compound represented by the following general formula (1) and a compound represented by the following general formula (2a):

General Formula (1)

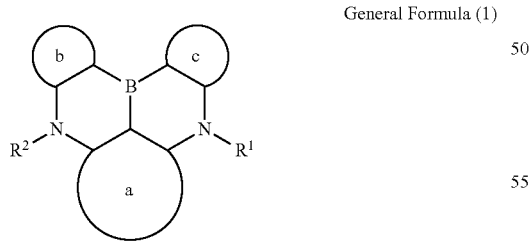

wherein ring a, ring b and ring c each independently represent a benzene ring that may be condensed with any other ring to form an aryl ring or a heteroaryl ring, and at least one hydrogen atom in these rings may be substituted; $R^1$ and $R^2$ each independently represent a substituted or unsubstituted aryl group, or a substituted or unsubstituted heteroaryl group bonding via the benzene ring; $R^1$ may bond to the carbon atom neighboring to the bonding position (atom) to N in ring a and/or ring c via —O—, —S—, —C(—$R^{c1}$)$_2$— or a single bond; $R^2$ may bond to the carbon atom neighboring to the bonding position (atom) to N in ring a and/or ring b via —O—, —S—, —C(—$R^{c2}$)$_2$— or a single bond; $R^{c1}$ and $R^{c2}$ each independently represent a hydrogen atom or an alkyl group;

General Formula (2a)

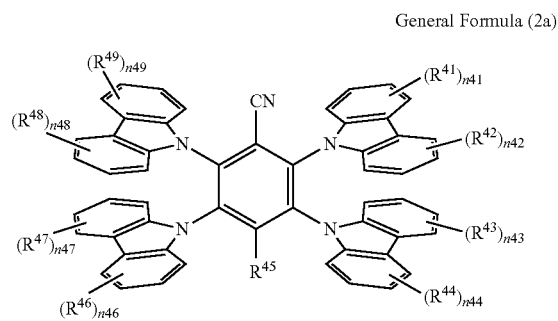

wherein $R^{41}$ to $R^{44}$, and $R^{46}$ to $R^{49}$ in general formula (2a) each independently represent a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group, but all four substituted or unsubstituted carbazol-9-yl groups bonding to benzonitrile in general formula (2a) are not the same; n41 to n44, and n46 to n49 each independently represent an integer of any of 0 to 4; and $R^{45}$ represents a hydrogen atom, a substituted or unsubstituted aryl group, a substituted or unsubstituted carbazol-9-yl group, or a cyano group.

\* \* \* \* \*